(12) United States Patent
Brown et al.

(10) Patent No.: US 10,549,274 B2
(45) Date of Patent: Feb. 4, 2020

(54) ELECTRICAL DEVICE WITH DETACHABLE COMPONENTS

(71) Applicant: Oxford Nanopore Technologies Ltd., Oxford (GB)

(72) Inventors: Clive Gavin Brown, Cambridge (GB); Jason Robert Hyde, Oxford (GB); Mark David Jackson, Oxford (GB); Paul Raymond Mackett, Oxford (GB); Jonathan Edward McKendry, Oxford (GB); Richard Kenneth John Wiltshire, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 369 days.

(21) Appl. No.: 15/519,659

(22) PCT Filed: Oct. 15, 2015

(86) PCT No.: PCT/GB2015/053066
§ 371 (c)(1),
(2) Date: Apr. 17, 2017

(87) PCT Pub. No.: WO2016/059417
PCT Pub. Date: Apr. 21, 2016

(65) Prior Publication Data
US 2017/0326550 A1    Nov. 16, 2017

(30) Foreign Application Priority Data

Oct. 17, 2014  (GB) .................................. 1418512.8
May 8, 2015   (GB) .................................. 1507904.9
May 13, 2015  (GB) .................................. 1508158.1

(51) Int. Cl.
*B01L 99/00*     (2010.01)
*B01L 3/00*      (2006.01)

(52) U.S. Cl.
CPC ..... *B01L 3/502715* (2013.01); *B01L 3/50857* (2013.01); *B01L 2200/04* (2013.01);
(Continued)

(58) Field of Classification Search
CPC .......... B01L 3/502715; B01L 3/50857; B01L 2200/12; B01L 2200/025; B01L 2200/04;
(Continued)

(56) References Cited

U.S. PATENT DOCUMENTS 3,799,743 A    3/1974  Alexander et al.
4,154,795 A    5/1979  Thorne
(Continued)

FOREIGN PATENT DOCUMENTS

CN    1303147 A      7/2001
CN    101490277 A    7/2009
(Continued)

OTHER PUBLICATIONS

[No Author Listed] Avanti Polar Lipids, Inc. Avanti Polar Lipids-Preparations of Liposomes. Www.avantilipids.com 5 pages. Jul. 1, 2014.
(Continued)

*Primary Examiner* — J. Christopher Ball
(74) *Attorney, Agent, or Firm* — Wolf, Greenfield & Sacks, P.C.

(57) ABSTRACT

A detachable electrical device can be formed from a kit comprising a pair of component parts adapted for connection to each other, wherein the connected components of the device may be subsequently disconnected, comprising: an array of electrical connectors, each electrical connector comprising an electrically conductive liquid; and an array of electrodes; wherein the arrays can be brought into contact with each other so as to provide a plurality of electrical connections between the electrically conductive liquid of the
(Continued)

array of electrical connectors and the electrodes of the array of electrodes, and wherein the electrical connections may be subsequently broken by detaching the electrically conductive liquid from the electrodes of the array.

22 Claims, 36 Drawing Sheets

(52) U.S. Cl.
CPC ... *B01L 2200/12* (2013.01); *B01L 2300/0645* (2013.01); *B01L 2300/161* (2013.01)

(58) Field of Classification Search
CPC ....... B01L 2300/161; B01L 2300/0819; B01L 2300/0645; B01L 2300/0636; H01R 13/02; H01R 3/08; G01N 33/48721
See application file for complete search history.

(56) References Cited

U.S. PATENT DOCUMENTS

| | | |
|---|---|---|
| 5,234,566 A | 8/1993 | Osman et al. |
| 5,403,451 A | 4/1995 | Riviello et al. |
| 6,056,922 A | 5/2000 | Ikematsu |
| 6,300,141 B1 | 10/2001 | Segal et al. |
| 6,479,288 B1 | 11/2002 | Laffafian et al. |
| 6,503,452 B1 | 1/2003 | Boxer et al. |
| 6,699,697 B2 | 3/2004 | Klemic et al. |
| 6,863,833 B1 | 3/2005 | Bloom et al. |
| 6,913,697 B2 | 7/2005 | Lopez et al. |
| 6,916,488 B1 | 7/2005 | Meier et al. |
| 7,077,939 B2 | 7/2006 | Crooks et al. |
| 7,144,486 B1 | 12/2006 | Fritsch et al. |
| 7,169,272 B2 | 1/2007 | Fritsch et al. |
| 7,745,116 B2 | 6/2010 | Williams |
| 7,939,270 B2 | 5/2011 | Holden et al. |
| 8,124,191 B2 | 2/2012 | Ervin et al. |
| 8,461,854 B2 | 6/2013 | Chen et al. |
| 9,057,102 B2 | 6/2015 | Turner et al. |
| 9,546,400 B2 | 1/2017 | Turner et al. |
| 9,556,480 B2 | 1/2017 | Turner et al. |
| 9,678,056 B2 | 6/2017 | Turner et al. |
| 9,738,929 B2 | 8/2017 | Turner et al. |
| 9,927,398 B2 | 3/2018 | Reid et al. |
| 10,215,768 B2 | 2/2019 | Sanghera et al. |
| 10,338,056 B2 | 7/2019 | Hyde et al. |
| 10,416,117 B2 | 9/2019 | Reid et al. |
| 2002/0123048 A1 | 9/2002 | Gau |
| 2003/0015422 A1 | 1/2003 | Fritsch et al. |
| 2003/0075445 A1 | 4/2003 | Woudenberg et al. |
| 2003/0098248 A1 | 5/2003 | Vogel et al. |
| 2003/0111340 A1 | 6/2003 | Cheng et al. |
| 2003/0148401 A1 | 8/2003 | Agrawal et al. |
| 2003/0224523 A1 | 12/2003 | Thornberg et al. |
| 2004/0171169 A1 | 9/2004 | Kallury et al. |
| 2005/0014162 A1 | 1/2005 | Barth et al. |
| 2005/0230272 A1 | 10/2005 | Lee et al. |
| 2006/0079009 A1 | 4/2006 | Salmon et al. |
| 2006/0163063 A1 | 7/2006 | Picollet-Dahan et al. |
| 2006/0257941 A1 | 11/2006 | McDevitt et al. |
| 2007/0035308 A1 | 2/2007 | Ide |
| 2007/0161101 A1 | 7/2007 | Takeuchi |
| 2008/0254995 A1 | 10/2008 | Kim et al. |
| 2009/0167288 A1 | 7/2009 | Reid et al. |
| 2010/0147450 A1 | 6/2010 | Takeuchi et al. |
| 2010/0190253 A1 | 7/2010 | Tazaki et al. |
| 2010/0304980 A1 | 12/2010 | Takeuchi et al. |
| 2011/0120871 A1 | 5/2011 | Reid et al. |
| 2011/0121840 A1 | 5/2011 | Sanghera et al. |
| 2011/0214991 A1 | 9/2011 | Kim et al. |
| 2011/0287414 A1 | 11/2011 | Chen et al. |
| 2011/0318774 A1 | 12/2011 | Larsen |
| 2012/0010085 A1 | 1/2012 | Rava et al. |
| 2013/0071932 A1 | 3/2013 | Itchoda et al. |
| 2013/0140192 A1 | 6/2013 | Behrends et al. |
| 2013/0217106 A1 | 8/2013 | Jones et al. |
| 2014/0255921 A1 | 9/2014 | Moysey et al. |
| 2014/0296083 A1 | 10/2014 | Brown et al. |
| 2014/0329693 A1 | 11/2014 | Reid et al. |
| 2014/0335512 A1 | 11/2014 | Moysey et al. |
| 2014/0346059 A1 | 11/2014 | Akeson |
| 2015/0014160 A1 | 1/2015 | Hyde et al. |
| 2015/0065354 A1 | 3/2015 | Moysey et al. |
| 2015/0191709 A1 | 7/2015 | Heron et al. |
| 2015/0204763 A1 | 7/2015 | Stelzle et al. |
| 2015/0218629 A1 | 8/2015 | Heron et al. |
| 2015/0265994 A1 | 9/2015 | Hyde et al. |
| 2015/0268256 A1 | 9/2015 | Sanghera et al. |
| 2015/0300986 A1 | 10/2015 | Reid et al. |
| 2016/0040230 A1 | 2/2016 | Akeson |
| 2016/0257942 A1 | 9/2016 | Bruce et al. |
| 2017/0363577 A1 | 12/2017 | Reid et al. |
| 2018/0321188 A1 | 11/2018 | Reid et al. |
| 2019/0210021 A1 | 7/2019 | Waterman |
| 2019/0242913 A1 | 8/2019 | Sanghera et al. |

FOREIGN PATENT DOCUMENTS

| | | |
|---|---|---|
| CN | 203466320 U | 9/2013 |
| DE | 102010022929 A1 | 12/2011 |
| EP | 0532215 A2 | 3/1993 |
| EP | 1110084 A1 | 6/2001 |
| EP | 1120469 A2 | 8/2001 |
| EP | 1535667 A1 | 6/2005 |
| EP | 1669746 A1 | 6/2006 |
| EP | 1677102 | 7/2006 |
| EP | 1688742 | 8/2006 |
| EP | 1710578 | 10/2006 |
| EP | 1712909 A1 | 10/2006 |
| EP | 1779921 A1 | 5/2007 |
| EP | 2219032 A1 | 8/2010 |
| GB | 2237390 | 5/1991 |
| GB | 2446823 | 8/2008 |
| JP | S5-274882 A | 6/1977 |
| JP | 4014773 A2 | 1/1992 |
| JP | 4127066 A2 | 4/1992 |
| JP | 4-215052 | 8/1992 |
| JP | 7307172 A2 | 11/1995 |
| JP | 2004-158330 A2 | 6/2004 |
| JP | 2005-98718 | 4/2005 |
| JP | 2005-539242 | 12/2005 |
| JP | 2006-312141 | 11/2006 |
| JP | 2008-194573 | 8/2008 |
| JP | 2009-128206 A | 6/2009 |
| JP | 2010186677 A * | 8/2010 |
| JP | 2010186677 A2 | 8/2010 |
| WO | WO 94/25862 A1 | 11/1994 |
| WO | WO 97/16545 A1 | 5/1997 |
| WO | WO 98/58248 | 12/1998 |
| WO | WO 2000/013014 A1 | 3/2000 |
| WO | WO 2000/025121 A1 | 5/2000 |
| WO | WO 2000/028312 | 5/2000 |
| WO | WO 2002/024862 A2 | 3/2002 |
| WO | WO 2002/029402 A2 | 4/2002 |
| WO | WO 2002/082046 A2 | 10/2002 |
| WO | WO 2003/052420 A2 | 6/2003 |
| WO | WO 2005/040783 A1 | 5/2005 |
| WO | WO 2006/012571 A1 | 2/2006 |
| WO | WO 2006/076703 A2 | 7/2006 |
| WO | WO 2006/100484 | 9/2006 |
| WO | WO 2006/104639 | 10/2006 |
| WO | WO 2006/113550 | 10/2006 |
| WO | WO 2006/138160 A2 | 12/2006 |
| WO | WO 2007/028003 A2 | 3/2007 |
| WO | WO 2007/049576 A1 | 5/2007 |
| WO | WO 2007/116978 A1 | 10/2007 |
| WO | WO 2007/127327 | 11/2007 |
| WO | WO 2007/132002 A1 | 11/2007 |
| WO | WO 2008/012552 A1 | 1/2008 |
| WO | WO 2008/102120 | 8/2008 |
| WO | WO 2008/102121 | 8/2008 |
| WO | WO 2008/124107 A1 | 10/2008 |
| WO | WO 2008/156041 A1 | 12/2008 |

(56) References Cited

FOREIGN PATENT DOCUMENTS

| WO | WO 2009/024775 A1 | 2/2009 |
|---|---|---|
| WO | WO 2009/035647 A1 | 3/2009 |
| WO | WO 2009/077734 A2 | 6/2009 |
| WO | WO 2010/122293 | 10/2010 |
| WO | WO 2010/142954 A1 | 12/2010 |
| WO | WO 2011/118211 A1 | 9/2011 |
| WO | WO 2011/154114 A2 | 12/2011 |
| WO | WO 2013/057495 A2 | 4/2013 |
| WO | WO 2013/121224 A1 | 8/2013 |
| WO | WO 2014/064443 A2 | 5/2014 |
| WO | WO 2014/064444 A1 | 5/2014 |
| WO | WO 2014/019603 A1 | 7/2015 |

OTHER PUBLICATIONS

Aghdaei et al., Formation of artificial lipid bilayers using droplet dielectrophoresis. Lab Chip. Oct. 2008;8(10):1617-20. doi: 10.1039/b807374k. Epub Aug. 13, 2008.

Anrather et al., Supported membrane nanodevices. J Nanosci Nanotechnol. Jan.-Feb. 2004;4(1-2):1-22.

Baaken et al., Planar microelectrode-cavity array for high-resolution and parallel electrical recording of membrane ionic currents. Lab Chip. Jun. 2008;8(6):938-44. doi: 10.1039/b800431e. Epub Apr. 16, 2008.

Bezrukov et al., Counting polymers moving through a single ion channel. Nature. Jul. 28, 1994;370(6487):279-81.

Bruggemann et al., Microchip technology for automated and parallel patch-clamp recording. Small. Jul. 2006;2(7):840-6.

Cheng et al., Discrete membrane arrays. J Biotechnol. Sep. 2000;74(3):159-74.

Cheng et al., Single Ion Channel Sensitivity in Suspended Bilayers on Micromachined Supports. Langmuir. 2001;17(4):1240-1242.

Danelon et al., Cell membranes suspended across nanoaperture arrays. Langmuir. Jan. 3, 2006;22(1):22-5.

Estes et al., Electroformation of giant liposomes from spin-coated films of lipids. Colloids Surf B Biointerfaces. May 10, 2005;42(2):115-23.

Funakoshi et al., Lipid bilayer formation by contacting monolayers in a microfluidic device for membrane protein analysis. Anal Chem. Dec. 15, 2006;78(24):8169-74.

Garstecki et al., Formation of droplets and bubbles in a microfluidic T-junction-scaling and mechanism of break-up. Lab Chip. Mar. 2006;6(3):437-46. Epub Jan. 25, 2006. Erratum in: Lab Chip. May 2006;6(5):693.

Hasanzadeh et al., Room-temperature ionic liquid-based electrochemical nanobiosensors. Trends Anal Chem. Dec. 2012;41:58-74.

Heron et al., Simultaneous measurement of ionic current and fluorescence from single protein pores. J Am Chem Soc. Feb. 11, 2009;131(5):1652-3. doi: 10.1021/ja808128s.

Hirano et al., Lipid Bilayers at Gel/Gel Interface for Ion Channel Recordings. Surf. Sci. Nanotech. 2008;6:130-133.

Holden et al., Functional bionetworks from nanoliter water droplets. J Am Chem Soc. Jul. 11, 2007;129(27):8650-5. Epub Jun. 16, 2007.

Hovis et al., Patterning and Composition Arrays of Supported Lipid Bilayers by Microcontact Printing. Langmuir. 2001;17:3400-3405.

Hromada et al., Single molecule measurements within individual membrane-bound ion channels using a polymer-based bilayer lipid membrane chip. Lab Chip. Apr. 2008;8(4):602-8. doi:10.1039/b716388f. Epub Feb. 29, 2008.

Ide et al., A novel method for artificial lipid-bilayer formation. Biosens Bioelectron. Oct. 15, 2005;21(4):672-7. Epub Jan. 26, 2005.

Jeon et al., Long-term storable and shippable lipid bilayer membrane platform. Lab Chip. Oct. 2008;8(10):1742-4. doi: 10.1039/b807932c. Epub Aug. 22, 2008.

Jung et al., Detecting protein-ligand binding on supported bilayers by local pH modulation. J Am Chem Soc. Jan. 28, 2009;131(3):1006-14. doi: 10.1021/ja804542p.

Kam et al., Spatially Selective Manipulation of Supported Lipid Bilayers by Laminar Flow: Steps Toward Biomembrane Microfluidic. Langmuir. 2003;19(5):1624-1631.

Kasianowicz et al., Protonation dynamics of the alpha-toxin ion channel from spectral analysis of pH-dependent current fluctuations. Biophys J. Jul. 1995;69(1):94-105.

Kim et al., Liquid-slate field-effect transistors using electrowetting. Applied Physics Letters. 90:043507-1-043507-3.

Krantz Lab. Planar Lip Bilayer Electrohpysiology Equipment. Department of Molecular & Cell Biology, University of California, Berkeley. Oct. 6, 2007. Last accessed at mcb.berkeley.edu/labs/krantz/equipment/blm.html on Nov. 26, 2014.

Kung et al., Printing via Photolithography on Micropartitioned Fluid Lipid Membranes. Adv. Materials. 2000;12(10):731-734.

Langecker et al., Synthetic lipid membrane channels formed by designed DNA nanostructures. Science. Nov. 16, 2012;338(6109):932-6. doi: 10.1126/science.1225624.

Le Pioufle et al., Lipid bilayer microarray for parallel recording of transmembrane ion currents. Anal Chem. Jan. 1, 2008;80(1):328-32. Epub Nov. 15, 2007.

Lee et al., Ion channel switch array:A biosensor for detecting multiple pathogens. Industrial Biotechnology. May 2005;1(1):26-31. doi:10.1089/ind.2005.1.26.

Lee et al., Nanoarrays of tethered lipid bilayer rafts on poly(vinyl alcohol) hydrogels. Lab Chip. Jan. 7, 2009;9(1):132-9. doi: 10.1039/b809732a. Epub Oct. 22, 2008.

Lee et al., Polyelectrolyte Micropatterning Using Agarose Plane Stamp and a Substrate Having Microscale Features on Its Surface. Bull. Korean Chem. Soc., vol. 26(10):1539-1542 (2005).

Lewis et al., The Mesomorphic Phase Behavior of Lipid Bilayers. Structure Biological Membranes. 3rd Ed. Ed: Yeagle. CRC Press 2011. 19-89.

Li et al., Microfluidic system for planar patch clamp electrode arrays. Nano Lett. Apr. 2006;6(4):815-9.

Mach et al., Miniaturized planar lipid bilayer: increased stability, low electric noise and fast fluid perfusion. Anal Bioanal Chem. Feb. 2008;390(3):841-6. Epub Oct. 31, 2007.

Majd et al., Hydrogel stamping of arrays of supported lipid bilayers with various lipid compositions for the screening of drug-membrane and protein-membrane interactions. Angew Chem Int Ed Engl. Oct. 21, 2005;44(41):6697-700.

Malmstadt et al., Automated formation of lipid-bilayer membranes in a microfluidic device. Nano Lett. Sep. 2006;6(9):1961-5.

Mastrangeli et al., Challenges for Capillary Self-Assembly of Microsystems. IEEE Transactions. Jan. 2011;1(1):133-149.

Mastrangeli et al., Self-assembly from milli- to nanoscales:methods and applications. J Micro Microeng. 2009;19:083001.

Maurer et al., Reconstitution of ion channels in agarose-supported silicon orifices. Biosens Bioelectron. May 15, 2007;22(11):2577-84. Epub Nov. 13, 2006.

McAlduff et al., Freestanding lipid bilayers as substrates for electron cryomicroscopy of integral membrane proteins. J Microsc. Feb. 2002;205(Pt 2):113-7.

Montal et al., Formation of bimolecular membranes from lipid monolayers and a study of their electrical properties. Proc Natl Acad Sci U S A. Dec. 1972;69(12):3561-6.

Moran-Mirabal et al., Micrometer-sized supported lipid bilayer arrays for bacterial toxin binding studies through total internal reflection fluorescence microscopy. Biophys J. Jul. 2005;89(1):296-305. Epub Apr. 15, 2005.

Ogier et al., Suspended Planar Phospholipid Bilayers on Micromachined Supports, Langmuir, vol. 16:5696-5701 (2000).

Onoe et al., Three-Dimensional Micro-Self-Assembly Using Hydrophobic Interaction Controlled by Self-Assembled Monolayers. J Micro Systems. Aug. 2004;13(4):603-611.

Parthasarathy et al., Protein patterns at lipid bilayer junctions. Proc Natl Acad Sci U S A. Aug. 31, 2004;101(35):12798-803. Epub Aug. 20, 2004.

Peterman et al., Ion Channels and Lipid Bilayer Membranes Under High Potentials Using Microfabricaled Apertures, Biomedical Microdevices, vol. 4(3):231-236 (2002).

Polk et al., Ag/AgCl microelectrodes with improved stability for microfluidics. Sensors Actuators B. 2006;114:239-247.

(56) References Cited

OTHER PUBLICATIONS

Romer et al., Impedance analysis and single-channel recordings on nano-black lipid membranes based on porous alumina. Biophys J. Feb. 2004;86(2):955-65.
Sackmann, Supported membranes: scientific and practical applications. Science. Jan. 5, 1996;271(5245):43-8.
Sandison et al., Rapid fabrication of polymer microfluidic systems for the production of artificial lipid bilayers. J. Micromelh. Microeng. 2005;15:S139-S144.
Sandison et al., Air-exposure technique for the formation of artificial lipid bilayers in microsystems. Langmuir. Jul. 17, 2007;23(15):8277-84. Epub Jun. 22, 2007.
Sapra et al., Lipid-coated hydrogel shapes as components of electrical circuits and mechanical devices. Sci Rep. 2012;2:848. doi: 10.1038/srep00848. Epub Nov. 14, 2012.
Sarles et al., Bilayer formation between lipid-encased hydrogels contained in solid substrates. ACS Appl Mater Interfaces. Dec. 2010;2(12):3654-63. doi: 10.1021/am100826s. Epub Nov. 10, 2010.
Schindler et al., Branched bimolecular lipid membranes. Biophys J. Sep. 1976;16(9):1109-13.
Schmidt et al., A Chip-Based Biosensor for the Functional Analysis of Single Ion Channels. Angew Chem Int Ed Engl. Sep. 1, 2000;39(17):3137-3140.
Shim et al., Stochastic sensing on a modular chip containing a single-ion channel. Anal Chem. Mar. 15, 2007;79(6):2207-13. Epub Feb. 9, 2007.
Smith et al., Micropatterned fluid lipid bilayer arrays created using a continuous flow microspotter. Anal Chem. Nov. 1, 2008;80(21):7980-7. doi: 10.1021/ac800860u. Epub Oct. 8, 2008.
Soni et al., Synchronous optical and electrical detection of biomolecules traversing through solid-state nanopores. Rev Sci Instrum. Jan. 2010;81(1):014301. doi: 10.1063/1.3277116.
Sun et al., Microfluidic static droplet arrays with tuneable gradients in material composition. Lab Chip. Dec. 7, 2011;11(23):3949-52. doi: 10.1039/c11c20709a. Epub Oct. 12, 2011.
Suzuki et al., Highly reproducible method of planar lipid bilayer reconstitution in polymethyl methacrylate microfluidic chip. Langmuir. Feb. 14, 2006;22(4):1937-42.
Suzuki et al., Planar lipid bilayer reconstitution with a micro-fluidic system. Lab Chip. Oct. 2004;4(5):502-5. Epub Sep. 2, 2004.
Suzuki et al., Planar Lipid Membrane Array for Membrane Protein Chip. 17th IEEE International Conference on Micro Electro Mechanical Systems (MEMS), pp. 272-275 (2004).
Syms et al., Surface Tension-Powered Self-Assembly of Microstructures—The State of the Art. J Micro Systems. Aug. 2003;12(4):387-417.
Thorsen et al., Dynamic pattern formation in a vesicle-generating microfluidic device. Phys Rev Lett. Apr. 30, 2001;86(18):4163-6.
Urisu et al., Formation of high-resistance supported lipid bilayer on the surface of a silicon substrate with microelectrodes. Nanomedicine. Dec. 2005;1(4):317-22.
Vulto et al., Microfluidic channel fabrication in dry film resist for production and prototyping of hybrid chips. Lab Chip. Feb. 2005;5(2):158-62. Epub Dec. 3, 2004.
Wagterveld et al., Ultralow hysteresis superhydrophobic surfaces by excimer laser modification of SU-8. Langmuir. Dec. 19, 2006;22(26):10904-8.
Zagnoni et al., Bilayer lipid membranes from falling droplets. Anal Bioanal Chem. Mar. 2009;393(6-7):1601-5. doi:10.1007/s00216-008-2588-5. Epub Jan. 19, 2009.
Zagnoni et al., Controlled delivery of proteins into bilayer lipid membranes on chip. Lab Chip. Sep. 2007;7(9):1176-83. Epub Jun. 27, 2007.
Zagnoni et al., Microfluidic array platform for simultaneous lipid bilayer membrane formation. Biosens Bioelectron. Jan. 1, 2009;24(5):1235-40. doi: 10.1016/j.bios.2008.07.022. Epub Jul. 23, 2008.
Bouaidat et al., Surface-directed capillary system; theory, experiments and applications. Lab Chip. Aug. 2005;5(8):827-36. Epub Jul. 1, 2005.
Bull et al., Polymer Films on Electrodes. J. Electrochem Soc. May 1982;129(5):1009-1015.
Case 1:17-cv-00275-LPS Document 18. Notice of subsequent events relating to Oxford's motion to dismiss (D.I. 9). Oct. 18, 2017.
Case 1:17-cv-00275-LPS Document 19. Oxford Nanopore Technologies, Inc.'s response to Pacific Biosciences of California, Inc.'s notice of subsequent events. Oct. 24, 2017.
Case 1:17-cv-00275-RGA Document 10. Oxford's opening brief in support of its motion to dismiss PacBio's complaint for patent infringement. May 8, 2017.
Case 1:17-cv-00275-RGA Document 14. PacBio's response to Oxford's motion to dismiss. Jun. 5, 2017.
Case 1:17-cv-00275-RGA Document 16. Oxford's reply brief in support of its motion to dismiss PacBio's complaint for patent infringement. Jun. 26, 2017.
Case 1:17-cv-01353-LPS Document 13. First Amended Complaint for Patent Infringement. Nov. 30, 2017.
Case 1:17-cv-01353-LPS Document 15. Plaintiff's response to Oxford Nanopore Technologies, Inc.'s Motion to Dismiss and Request for Scheduling Conference. Nov. 30, 2017.
Case 1:17-cv-01353-RGA Document 10. Oxford's opening brief in support of its motion to partially dismiss Pacbio's complaint for patent infringement. Nov. 16, 2017.
Horn, Avoiding Evaporation. Ibidi. Application Note 12. Mar. 29, 2012, pp. 1-3.
Ikariyama et al., Polypyrrole electrode as a detector for electroinactive anions by flow injection analysis. Anal. Chem. 1986, 58, 8, 1803-1806.
United States District Court for the District of Delaware Order. *Pacific Biosciences of California, Inc. v. Oxford Nanopore Technologies, Inc.* Civil Action No. 17-275-RGA. Nov. 9, 2017.
U.S. Appl. No. 16/404,107, filed May 6, 2019, Hyde et al.
U.S. Appl. No. 15/905,440, filed Feb. 26, 2018, Reid et al.
PCT/GB2015/053066, dated Apr. 7, 2016, International Search Report and Written Opinion.
PCT/GB2015/053066, dated Apr. 27, 2017, International Preliminary Report on Patentability.

* cited by examiner

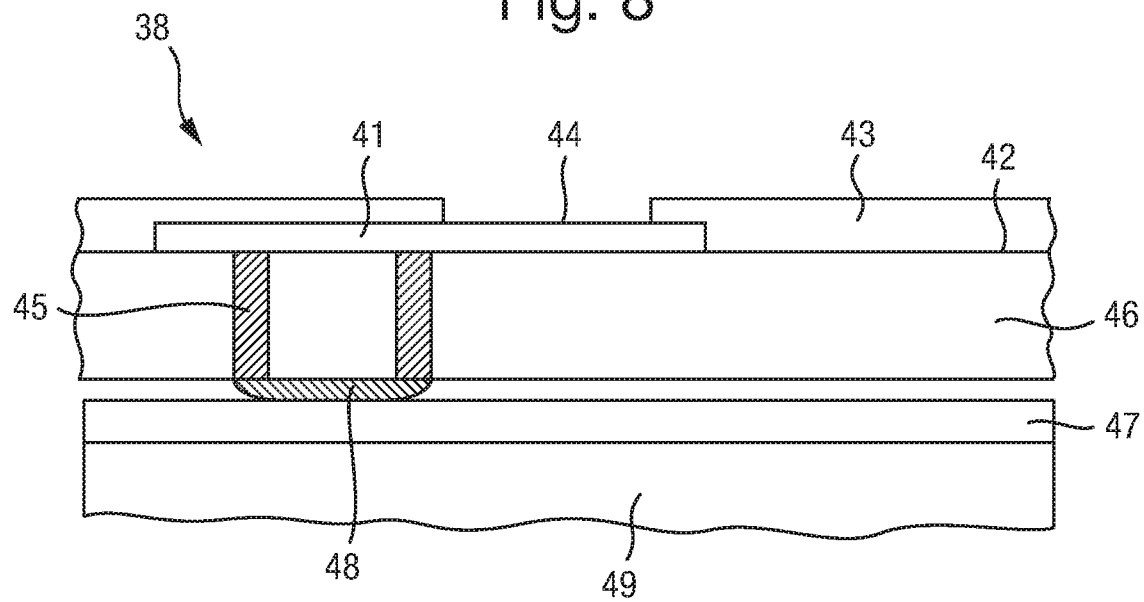
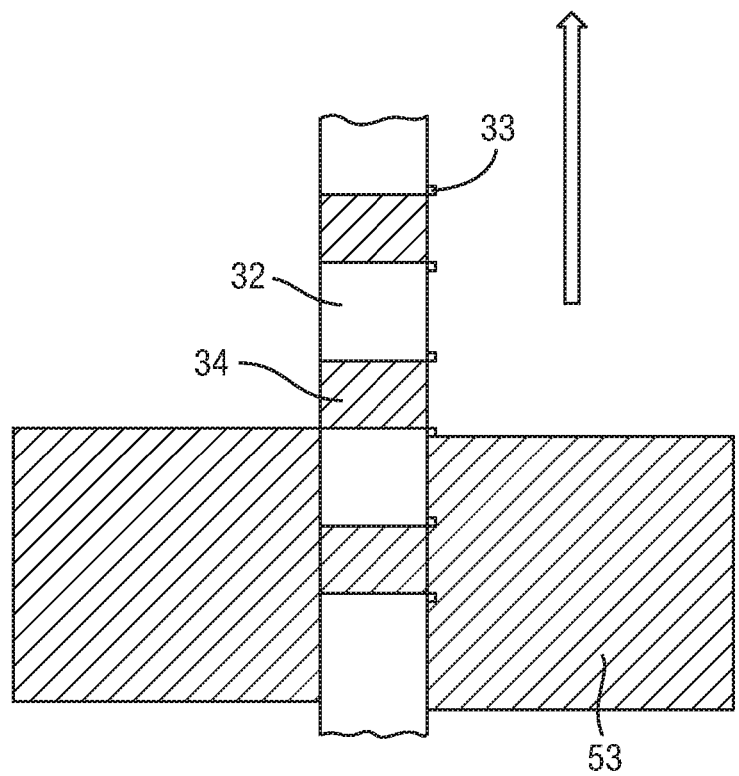

Fig. 9
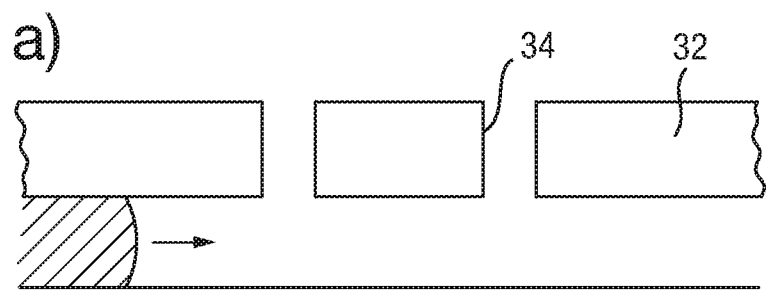
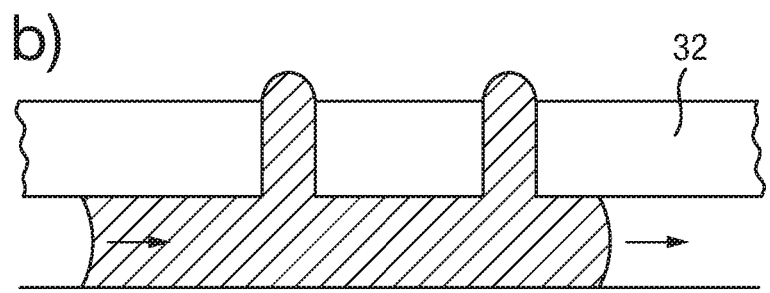
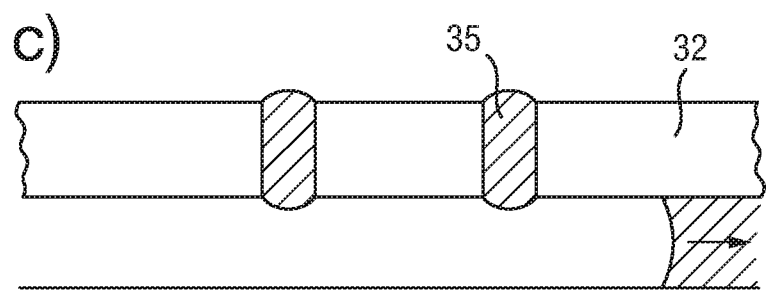

Fig. 26
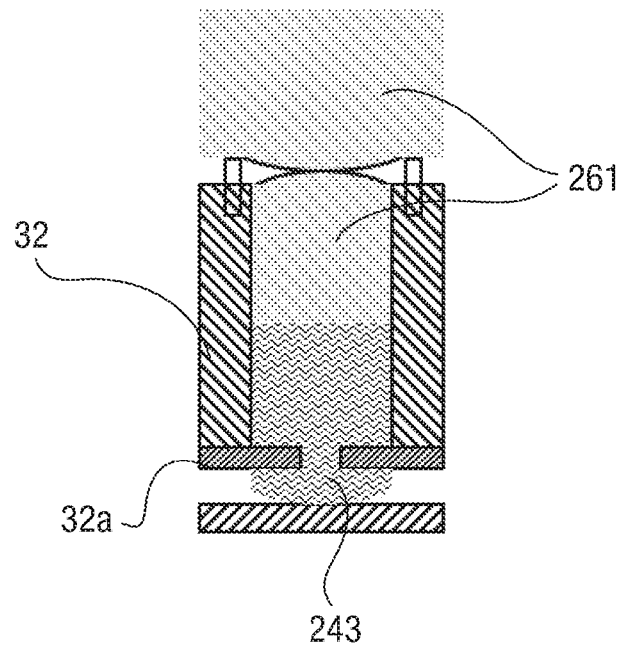
Fig. 27
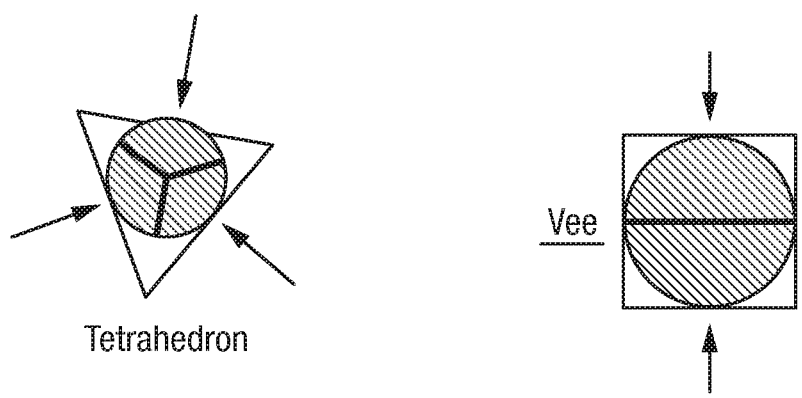
Tetrahedron
Vee
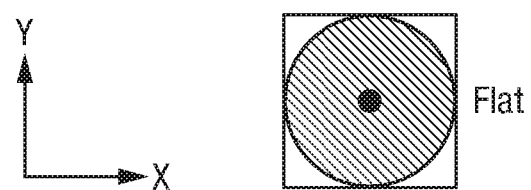
Flat

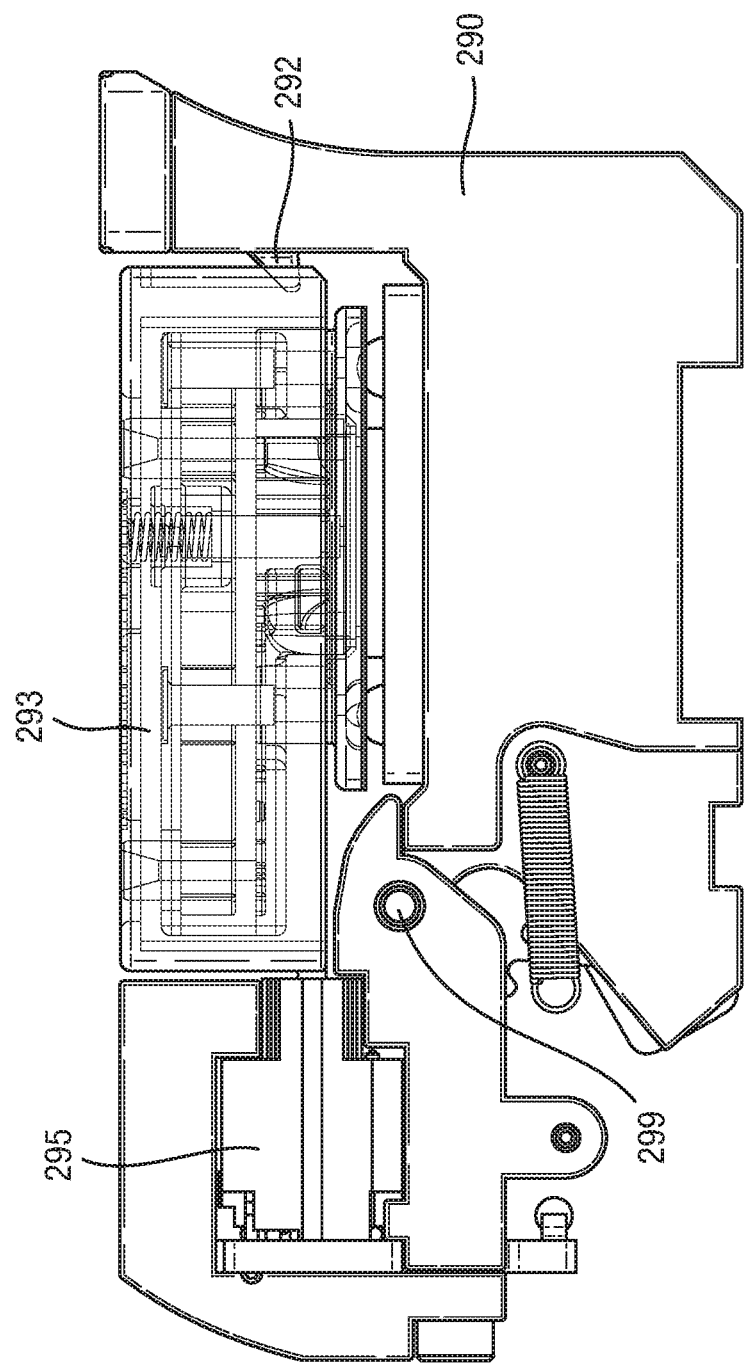

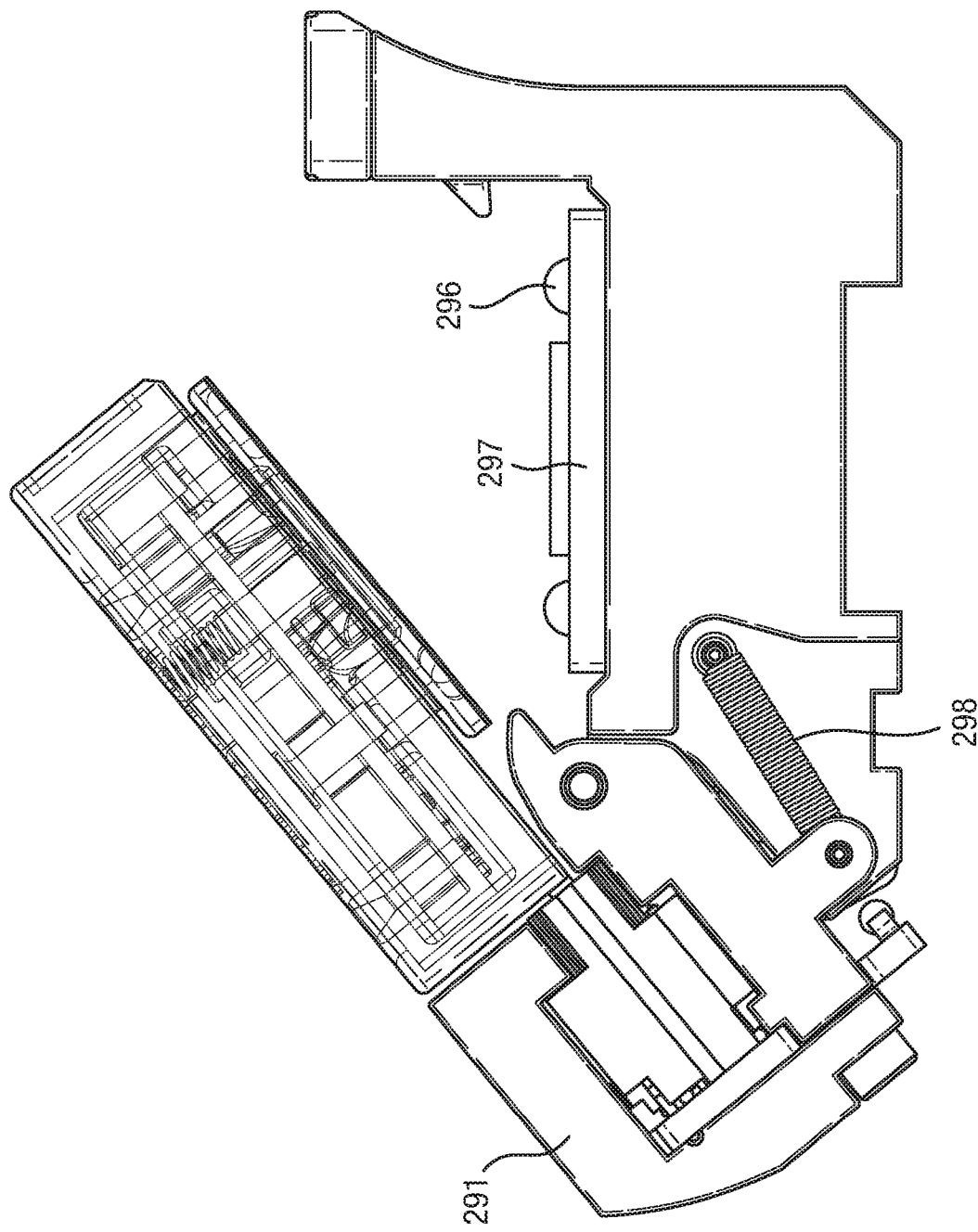

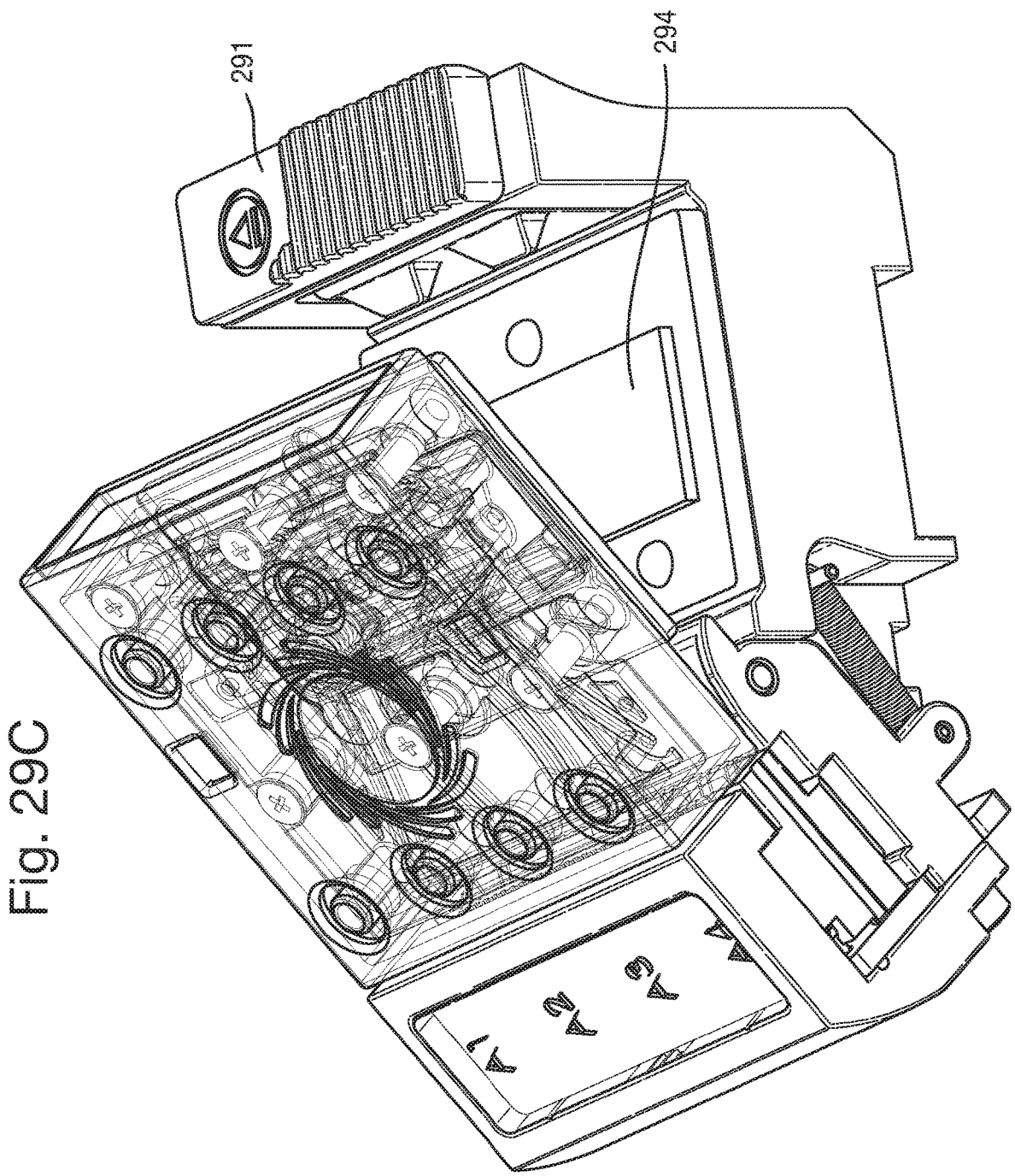

Fig. 29H
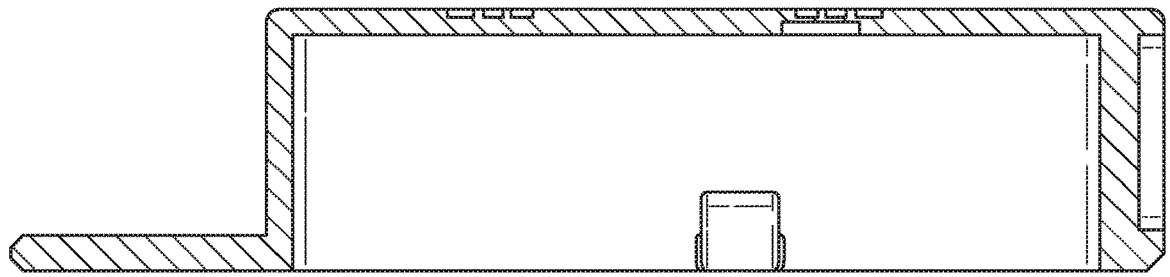
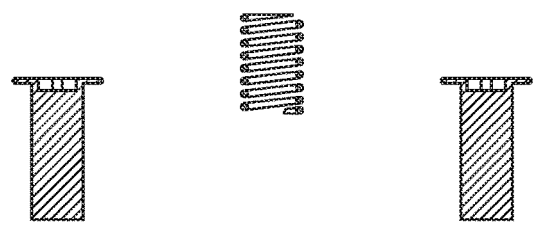
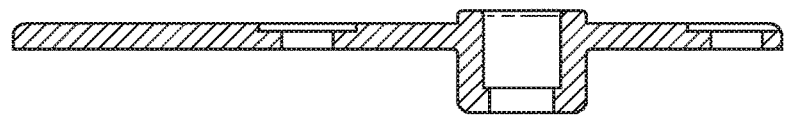
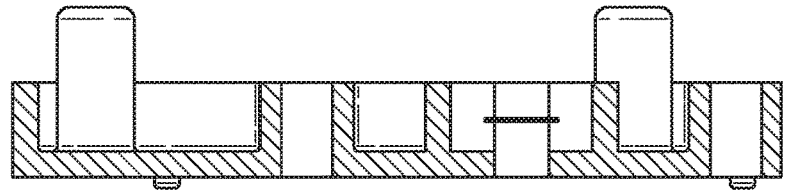
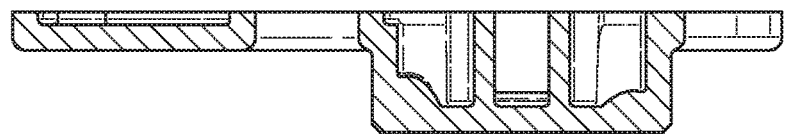
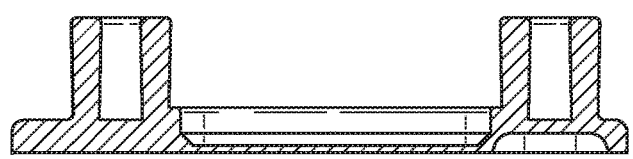

293  294

Fig. 37
(a)
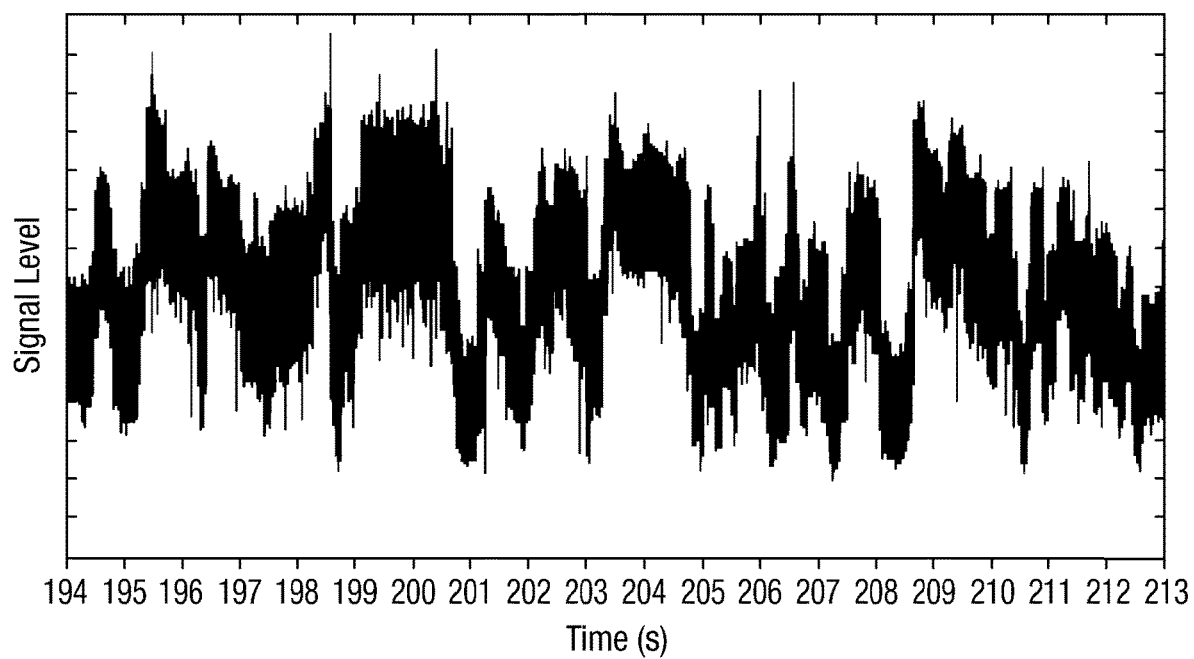
(b)
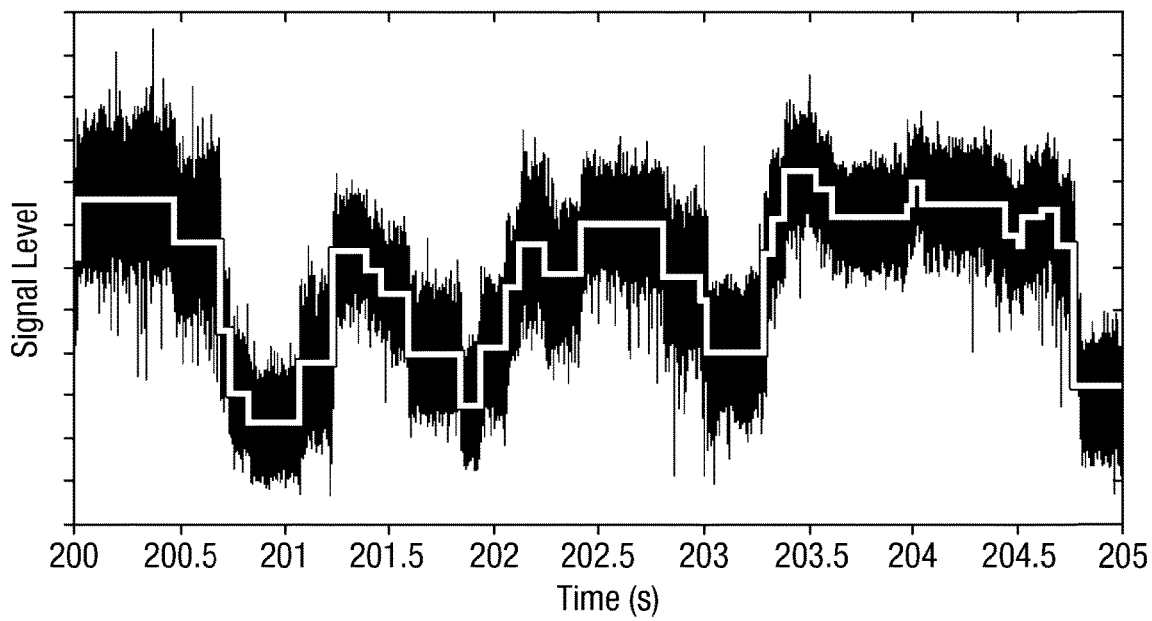

ELECTRICAL DEVICE WITH DETACHABLE COMPONENTS

This Application is a national stage filing under 35 U.S.C. § 371 of PCT International Application No. PCT/GB2015/053066, which has an international filing date of Oct. 15, 2015, and claims foreign priority benefits under 35 U.S.C. § 119(a)-(d) or 35 U.S.C. § 365(b) of British application number 1418512.8, filed Oct. 17, 2014; British application number 1507904.9, filed May 8, 2015; and British application number 1508158.1, filed May 13, 2015. The contents of the aforementioned applications are herein incorporated by reference in their entireties.

The present invention relates to an electrical device with detachable electrical components. The components can be connected to form an electrical connection between the components, and then separated to break the electrical connection and optionally allow the connection to be reformed by reconnecting the components.

A variety of ways of making an electrical connection are known. At small scales, such connections are often made by soldering, as this is a reliable way of ensuring a good connection between two connectors. However, when there is a need to make many connections within a small area, soldering the connections can become difficult. One way of overcoming this difficulty has been to use 'solder bump' or 'flip chip' technology, in which an array of connections on e.g. an integrated circuit are provided with bumps of solder that can subsequently be used to make the necessary connections with e.g. another electrode array.

An example of the usage of the 'solder bump' approach is provided by WO 2009/077734. That patent application discloses an apparatus for creating layers of amphiphilic molecules, and is now briefly discussed with reference to FIGS. 1 and 2.

FIG. 1 shows an apparatus 1 which may be used to form a layer of amphiphilic molecules. The apparatus 1 includes a body 2 having layered construction comprising a substrate 3 of non-conductive material supporting a further layer 4 also of non-conductive material. A recess 5 is formed in the further layer 4, in particular as an aperture which extends through the further layer 4 to the substrate 3. The apparatus 1 further includes a cover 6 which extends over the body 2. The cover 6 is hollow and defines a chamber 7 which is closed except for an inlet 8 and an outlet 9 each formed by openings through the cover 6. The lowermost wall of the chamber 7 is formed by the further layer 4.

In use aqueous solution 10 is introduced into the chamber 7 and a layer of amphiphilic molecules is formed across the recess 5 separating aqueous solution 10 in the recess 5 from the remaining volume of aqueous solution in the chamber 7. Use of a chamber 7 which is closed makes it very easy to flow aqueous solution 10 into and out of the chamber 7. This is done simply by flowing the aqueous solution 10 through the inlet 8 until the chamber 7 is full. During this process, gas (typically air) in the chamber 7 is displaced by the aqueous solution 10 and vented through the outlet 9.

The apparatus includes the following electrode arrangement to allow measurement of electrical signals across the layer of amphiphilic molecules. The substrate 3 has a first conductive layer 20 deposited on the upper surface of the substrate 3 and extending under the further layer 4 to the recess 5. The portion of the first conductive layer 20 underneath the recess 5 constitutes an electrode 21 which also forms the lowermost surface of the recess 5. The first conductive layer 20 extends outside the further layer 4 so that a portion of the first conductive layer 20 is exposed and constitutes a contact 22.

The further layer 4 has a second conductive layer 23 deposited thereon and extending under the cover 6 into the chamber 7, the portion of the second conductive layer 23 inside the chamber 7 constituting an electrode 24. The second conductive layer 23 extends outside the cover 6 so that a portion of the second conductive layer 23 is exposed and constitutes a contact 25. The electrodes 21 and 24 make electrical contact with aqueous solution in the recess 5 and chamber 7. This allows measurement of electrical signals across the layer of amphiphilic molecules by connection of an electrical circuit 26 to the contacts 22 and 25.

The solder bump approach is used in embodiments that have multiple recesses 5, because it is necessary to allow individual electrical connections to the bottom of each well. This is shown in FIG. 2. In FIG. 2, the single conductive layer 20 is replaced with individual conductive paths 28 which extend through the body 2 to a contact 29 on the opposite side of the body 2 from the electrode 21 at the bottom of the recess 5. This arrangement allows for the use of solder bump connections. In particular, deposited on each contact 29 are respective solder bumps 60 on which a circuit element 61 can be mounted so that the solder bumps 60 make electrical contact with a track 62 on the circuit element 61.

However, although the solder bump process allows for many electrical connections to be made reliably in close proximity, it suffers from the drawback that the electrical connections formed are permanent.

Methods for forming permanent electrical connections at small scales are known wherein for example component parts are aligned by self-assembly and subsequently joined mechanically. For example, see "Three Dimensional Micro-Self-Assembly Using Hydrophobic Interaction Controlled by Self-Assembled Monolayers" (Onoe et al., Journal of Microelectromechanical Systems, 2004, Vol. 13, No.4, pp 603-611); "Challenges for Capillary Self-Assembly of Microsystems" (Mastrangeli et al., IEEE Transactions on Components, Packaging, and Manufacturing Technology, 2011, Vol. 1, No. 1, pp 133-149); "Surface Tension-Powered Self-Assembly of Microstructures—The State-of-the-Art" (Syms et al., Journal of Microelectromechanical Systems, 2003, Vol. 12, No.4, pp 387-417); and "Self-assembly from milli- to nanoscales: methods and applications" (Mastrangeli et al., Journal of Micromechanics and Microengineering, 2009, Vol. 19, DOI: 10.1088/0960-1317/19/8/083001). However, such techniques often require extreme environments (whether in terms of chemical activation, or in terms of system variables such as temperature or pressure), which may not be suitable for electrical devices with sensitive components and also provide permanent electrical connections.

Therefore, it is an object of the present invention to at least partially overcome the problems discussed above.

According to a first aspect of the invention there is provided a kit comprising a pair of component parts adapted for connection to each other to provide a detachable electrical device, wherein the connected components of the device may be subsequently disconnected, comprising: an array of electrical connectors, each electrical connector comprising an electrically conductive liquid; and an array of electrodes; wherein the arrays can be brought into contact with each other so as to provide a plurality of electrical connections between the electrically conductive liquid of the array of electrical connectors and the electrodes of the array of electrodes, and wherein the electrical connections may be subsequently broken by detaching the electrically conductive liquid from the electrodes of the array. The device is an electrochemical device for measuring ion current flow between respective electrical connectors and electrodes of the array.

According to this aspect, it is possible to connect and disconnect the component parts in order to connect and disconnect the electrical connectors from the electrodes (or reconnect a different set of electrical connectors to the electrodes), whilst enabling a plurality of viable electrical connections to be made at very close pitches and small scale. This can help facilitate the renovation or maintenance of the various component parts of the overall device constructed from the kit, or can allow for some of the component parts to be used disposably, whilst allowing other parts (perhaps with higher value or manufacturing costs) to be repeatedly re-used.

In particular the device is suitable for use as an analytical device for performing an analysis wherein the device may be contaminated during use, or wherein one of the component parts has a limited measurement lifetime. The provision of detachable components avoids the need to replace the device in its entirety as it permits the disposal of one of the components, such as the component comprising the electrode connectors, whilst permitting reuse of the other component part, such as the component comprising the electrode array, which is more expensive to replace or which has not become contaminated.

The electrically conductive liquid may be an ionic liquid or an ionic solution. Using ionic liquids provides an advantage in terms of longevity of the electrical connectors, because ionic liquids typically have a low vapour pressure and so evaporate only very slowly.

The electrically conducting liquid is optionally a gel having the properties of a semi-solid or solid. The gel can be a polymer hydrogel comprising a network of polymer chains. The polymer may optionally be cross-linked. The use of a gel assists with extending the longevity of the connectors, mitigates against migration of the fluid from the connectors between electrodes and assists in maintaining the shape of the electrically conductive liquid thus increasing the reliability of the electrical connections. However non-gelled electrically conducting liquids may also be used.

The electrodes may be of any convenient diameter. The electrode diameter may typically be any diameter in the range of 50 µm to 500 µm.

An individual droplet of an electrically conductive liquid may be provided on each electrode of the array. For an electrode diameter of 100 µm, the droplet may typically have a height of 100 µm or less, optionally 50 µm or less, optionally 20 µm or less above the electrodes, optionally 10 µm or less, further optionally 5 µm or less. As such, the droplets can project from the surface, making it easier to form reliable electrical connections with the array of electrical connectors, even if the array of electrical connectors and the array of electrodes are not on perfectly planar surfaces. The optimal droplet size may depend upon whether the electrically conductive liquid is in the form of a gel as well as its properties.

The electrical connections may be formed by self-assembly, namely where the surface energy between the electrical connectors and either the electrodes of the array or the droplets provided on the surfaces of the electrodes of the array is such that the electrical connectors self-align and connect with the electrode surfaces or the droplets provided on the electrodes in order to minimise surface tension. This has the advantage that the liquid connectors do not have to be exactly aligned with the electrodes of the array in order to provide the connections. The number of electrical connectors is optionally equal to the number of electrodes of the array of electrodes. This is the most efficient use of electrodes, if the electrodes are fully aligned with the electrical connectors.

The array of electrical connectors and the array of electrodes can each have a pitch of 1 mm or less, optionally 500 µm or less, further optionally 200 µm or less. The number of electrodes of the array can be greater than 100, optionally greater than 1000, and further optionally greater than 10,000, further optionally greater than 100,000. That is, the connections can be made in high numbers and at very small scales and pitches. Due to the high number of connections per unit area, the surface tension between the arrays when connected can be sufficient to hold the component parts together and substantially prevent lateral movement of the arrays with respect to each other.

The array of electrical connectors and the array of electrodes are optionally respectively provided in first and second bodies. The electrodes are optionally provided at a surface of the second body. The plurality of electrical connections may be formed by bringing respective surfaces of the first and second bodies into contact or close proximity. In practice, the surfaces themselves may not actually contact, due to the contact between the electrical connectors and the electrodes (especially if the electrical connectors project away from the surface of the first body).

The respective surfaces of the first and second bodies are optionally planar. Planar surfaces allow for more connections to be formed more reliably across a large array.

The first and second bodies optionally comprise alignment means so as to substantially prevent lateral movement between the two surfaces when the electrical connections are formed. The alignment means can be provided on the surfaces of each respective body. The alignment means optionally permits contact of the array of electrical connectors and the array of electrodes such that they are offset from each other when contacted and wherein the number of resultant electrical connections between the arrays is less than the number of electrical connectors or electrodes of each respective array. As such, perfect alignment of the two arrays may not be achieved, but a plurality of electrical connections may still be made. The alignment means may be magnetic. This enables the subsequently assembled electrical device to be robust such that the plurality of electrical connections between the component parts are maintained in use.

However the surface tension between the array of electrical connectors and the array of electrodes may be sufficient alone to align the two bodies wherein the physical alignment relies on self-assembly.

The first body may be stored in the form of being connected to a 'blank' second body in order to protect the capillary channels at the surface of the first body and the electrically conductive liquid contained within or projecting therefrom. The surface of the blank second body may comprise an electrically insulating oil such as a silicone oil in order to electrically isolate the projecting portions of the electrically conducting liquid or the ends of the capillary channels. In order to provide the electrical device, the first body may be disconnected from the blank second body and connected to a second body comprising the array of electrodes. In the case where the liquid connector is aqueous based, such as a gel, provision of the surface of the first body in oil substantially prevents the evaporation of water from the portion of the electrical connector that projects from the capillary channel. Evaporation of water causes shrinkage of the projection which may result in a poor electrical connection or no electrical connection between the connector and the electrode of the array.

The first and/or second body optionally comprises a flow barrier to substantially prevent the flow of the electrically conducting liquid between the electrodes of the array of electrodes when the electrical connections are formed. The flow barrier optionally comprises the surface between electrodes being hydrophobic relative to the surface of the electrodes. The flow barrier also optionally comprises an electrically insulating fluid medium provided between the first and second bodies. The fluid medium can be provided on the surface of the second body and wherein said medium may be displaced from the surface of the electrodes of the array of electrodes by contact between the electrodes and the electrically conductive liquid of the electrical connectors. The fluid medium can be an oil such as a silicone oil. The flow barriers assist in achieving a one-to-one connection between individual electrical connectors and individual electrodes.

The second body optionally comprises an integrated circuit. The electrodes of the array of electrodes are optionally connected to the integrated circuit by connectors that extend from the electrodes into the second body.

The array of electrical connectors can be disposed in an array of capillaries. The capillaries can extend to a surface of the first body. The ends of each capillary provided at the surface of the first body can have a convex surface. The second array of electrical connectors can project from the array of capillaries. The extent of projection of the electrically conducting liquid depends upon the width of the capillaries, and typically the maximum extent of projection is approximately 50% of the capillary width. Thus for a capillary of a width of 100 µm, the projection may be 50 µm or less, and optionally 30 µm or less. The extent of projection will depend upon the width of the capillaries. For example, for a capillary width of 100 µm, gel projections of length greater than 100 µm have tendency to break. In general an optimum aspect ratio of capillary width to depth of projection for a gelled electrical connector is 1:1 or less. The aspect ratio may be between a value of 1:1 to 10:1. Providing the electrical connectors within capillaries assists with the formation of the connectors and also assists with keeping the connectors separate from each other. By having the electrical connectors extend away from the end of the capillaries, connections can be made more reliably across the entire array if the array is not entirely planar. The provision of the electrically conductive liquid as a gel within the capillaries is advantageous as it assists in maintaining the shape of the projecting liquid from the capillaries. The provision of gel droplets on the electrodes of the array confers similar advantages. The gel may be provided within the capillary channels and/or on the surface of the electrodes of the array in liquid form and subsequently solidified to provide a solid or semi-solid. However the electrically conducting liquid may also be in liquid form, with the portion of the liquid projecting from the capillary being held in position by surface tension. The first body or component part optionally comprises one more electrodes so as to provide a plurality of capillary ionic flow paths through the electrically conducting liquid between the one or more electrodes and electrodes of the array of electrodes, when connected to form an electrical circuit. A resistance between one of the one of more electrodes and a respective electrode of the array of electrodes, when the electrical connections are formed, are typically greater than 1 k$\Omega$, optionally greater than 1 M$\Omega$, further optionally greater than 100 M$\Omega$, further optionally greater than 200 M$\Omega$, and further optionally greater than 1 G$\Omega$. The resistance may be even greater, for example between 1 and 10 G$\Omega$ or more. The resistance may be provided by a resistor in an electrical circuit, namely a two terminal passive electrical component. The resistance may be provided by one or more very small apertures in a resistive membrane provided between an ionic liquid or solution. The aperture may be for example between 1 and 50 nm in width.

Liquid electrical connections are well suited for use in systems in accordance with the invention having a high resistance and very low current passages typically in the region of 1 µA to 0.1 pA. The current passage may be in the range of 10 to 1000 pA, such as in the range of 50 to 300 pA. Thus the use of metal contacts to provide electrical connections of low resistance between the first and second bodies is not required.

The device may be represented as an electrical circuit wherein various components of the circuit have an electrical resistance associated with them, such as the resistance of the high resistant resistor or membrane aperture, the resistance of the ionic solution or liquid, and the resistance at an electrode interface between the ionic solution or liquid. A constituent of the resistance at the interface between an electrical connector and an electrode to be connected is the contact resistance between the two. The contact resistance may vary depending upon for example, the area of contact between the two components to be connected and the extent of surface contamination of the electrode. In use, ion current flow takes place between electrodes that are polarised, namely under an applied potential difference. As such negative ions flow towards the positively charged electrode and vice-versa. The interface may be considered as a double layer which provides a capacitive element. The electrical circuit may be represented as an RC circuit having a capacitance associated with the resistance at the electrode solution/liquid interface. There is also an associated capacitance at the membrane comprising the aperture.

The resistance at the interface between the electrically conducting liquid and an electrode of the array of electrodes, when the electrical connections are formed, can be 1% or less, optionally 0.1% or less, further optionally 0.01% or less, and further optionally 0.001% or less than the total resistance between one of the one of more electrodes and an electrode of the array of the array of electrodes.

The one or more electrodes in the first body may be an electrode that is common to the plurality of ionic flow paths.

The first body optionally comprises a plurality of nanopores, wherein each nanopore is provided in an insulating substrate provided across the ionic flow path such that current is passed between the electrically conducting liquid and the one of more electrodes through the nanopores. As such the body containing the nanopores may be removable from the rest of the device. The insulating substrate may be a membrane comprising a layer of amphipathic molecules.

According to another aspect of the invention, there is provided a detachable electrical device assembled from a kit according to any embodiment of the previous aspect. The detachable electrical device may be for characterising an analyte.

One or more such devices may be provided in modular form within a housing to provide an analysis instrument. The analysis instrument or the device itself may further comprise one or more of, a processor to process the electrical signals from the array of electrodes, a display to display the results of the data processing, a data storage means to store data in relation to the measurements, a data transfer means to transfer data from the device for storage or analysis and a power supply.

According to another aspect of the invention, there is provided a method of connecting an electrical device, the method comprising: providing an array of electrical connectors wherein each electrical connector comprises an electrically conductive liquid; providing an array of electrodes; and bringing the first and second arrays into contact to form a plurality of electrical connections between respective electrodes of the array and the electrically conductive liquid. The method optionally further comprises separating the electrically conducting liquid from the electrodes of the array of electrodes in order to break the electrical connections.

According to another aspect of the invention, there is provided an array of electrical connectors for use in the kit of any of the embodiments of the first aspect, wherein each electrical connector comprises an electrically conductive liquid.

According to another aspect of the invention, there is an array of electrodes for use in the kit of any of the embodiments of the first aspect, wherein the surface between electrodes is hydrophobic compared to the electrodes.

The invention is discussed below, by way of example only, with reference to the following figures in which:

FIG. 8 is a schematic diagram of the construction of an electrode in an array of electrodes;

FIGS. 9a, 9b, 9c is a series of schematic diagrams indicating how an array of amphiphilic membranes may be formed;

FIG. 10 is a schematic diagram illustrating another method for forming an array of liquid electrical connectors;

FIG. 26 is another alternative process for forming connectors;

Figure 28:
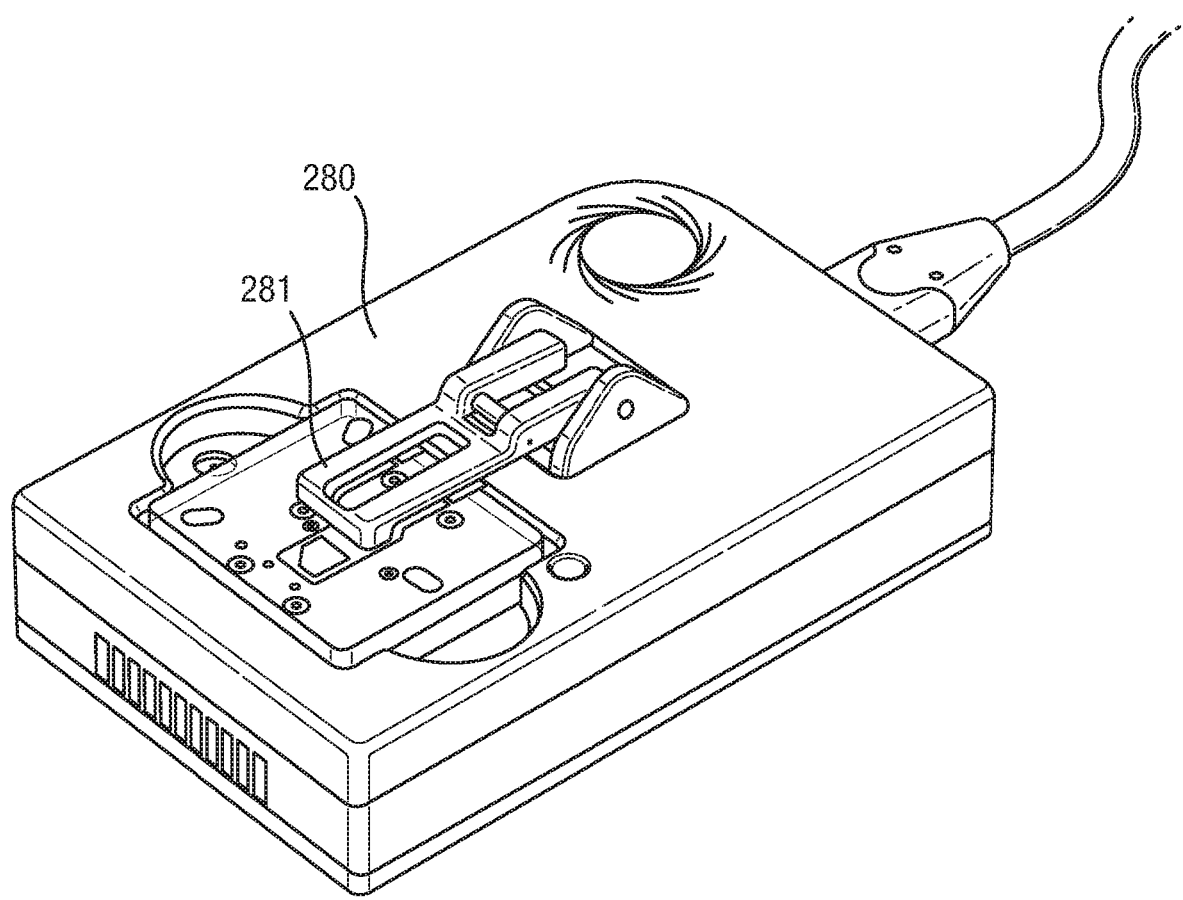
Figure 29D:
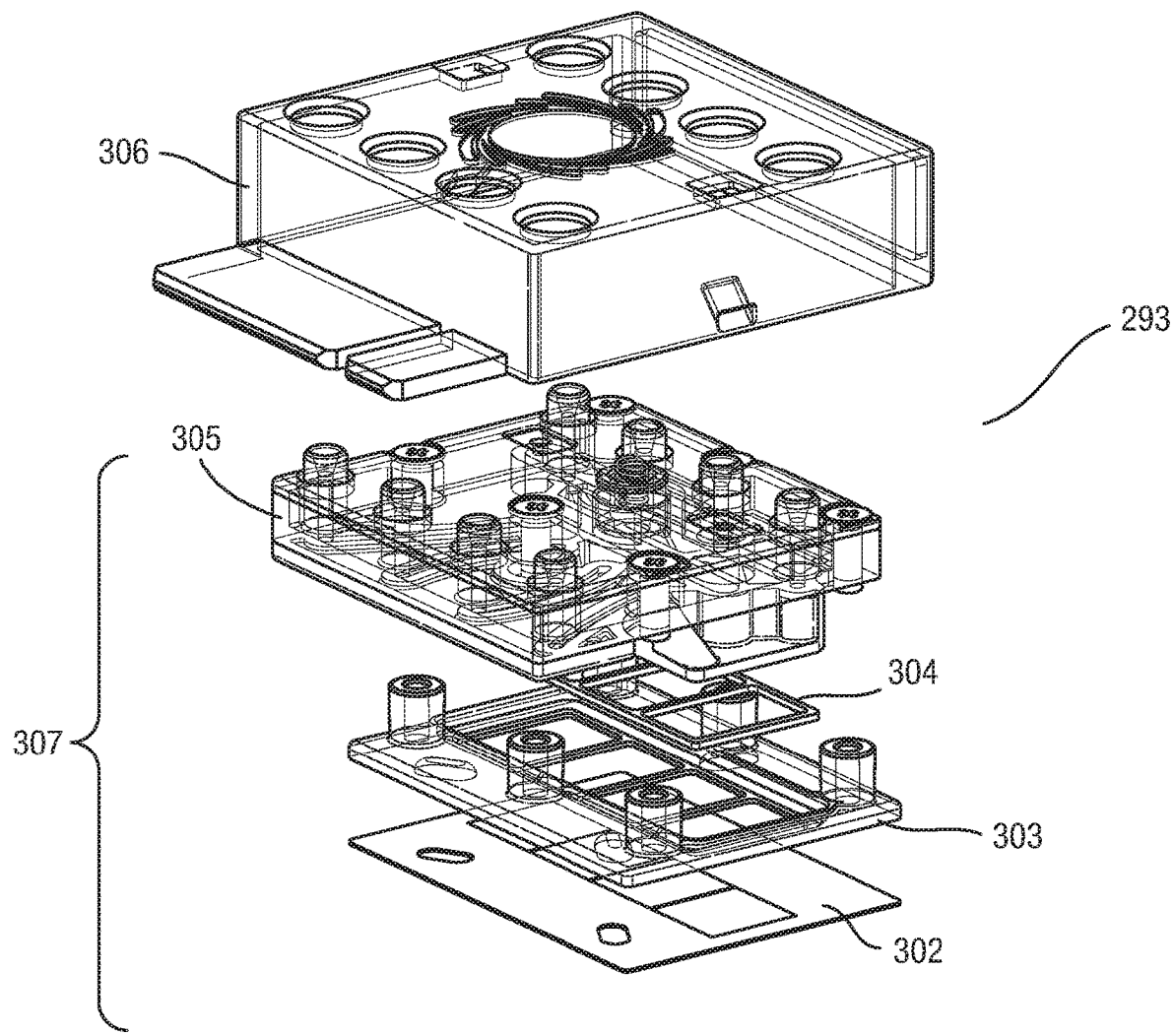
Figure 29E:
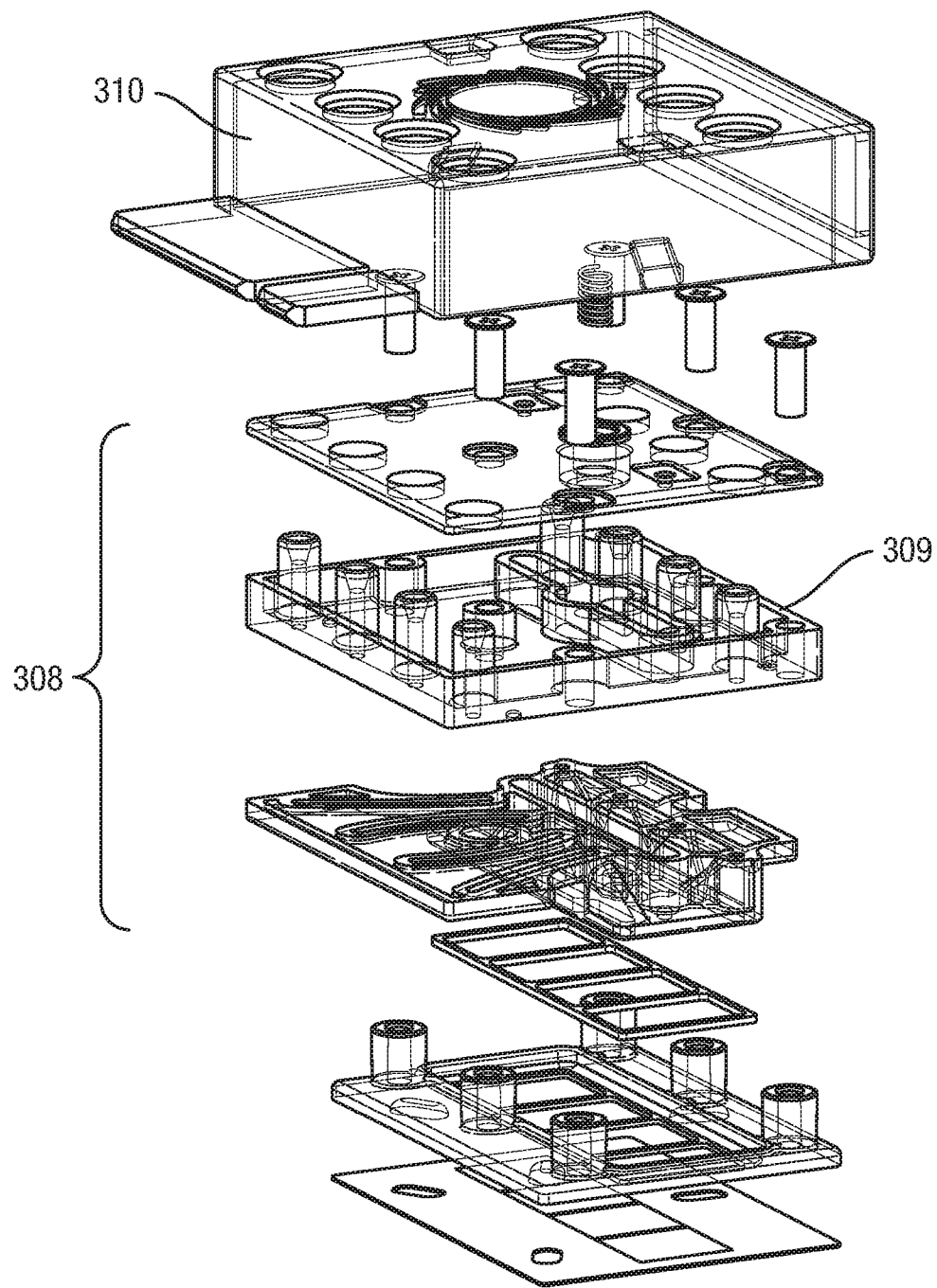
Figure 29F:
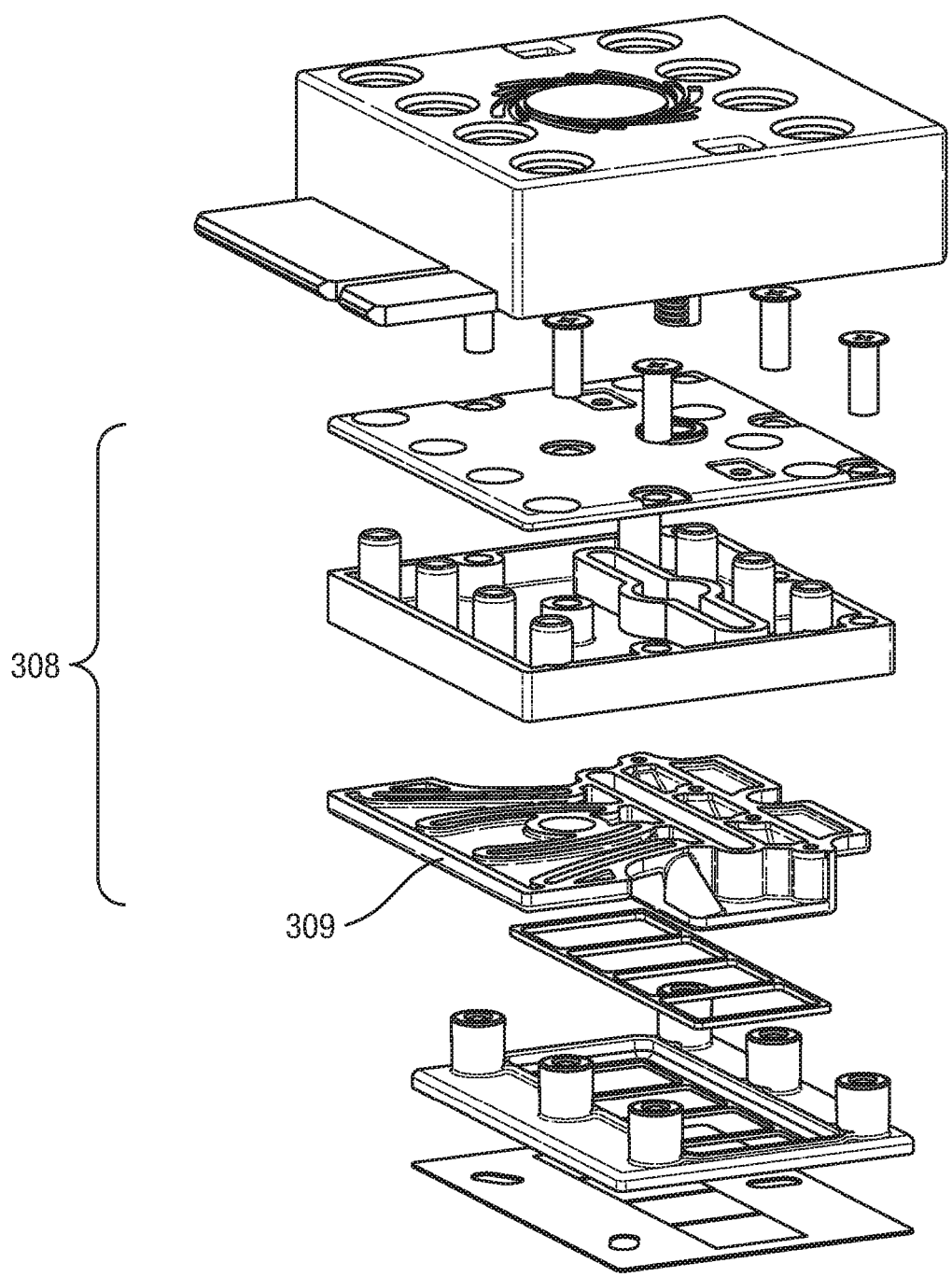
Figure 29G:
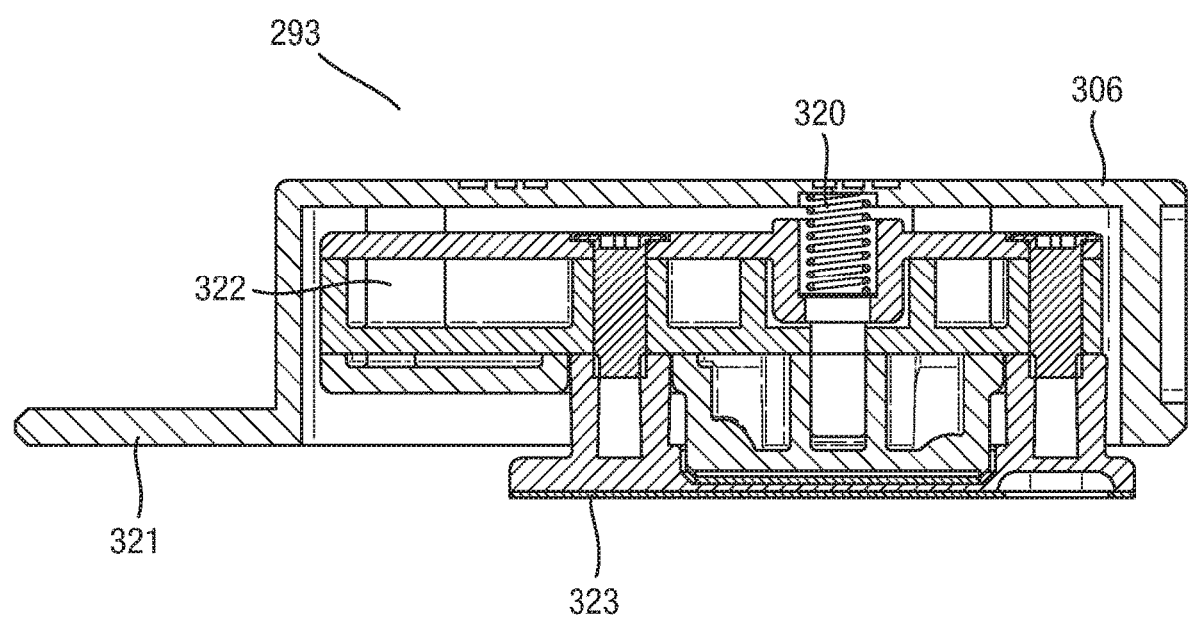
Figure 29I:
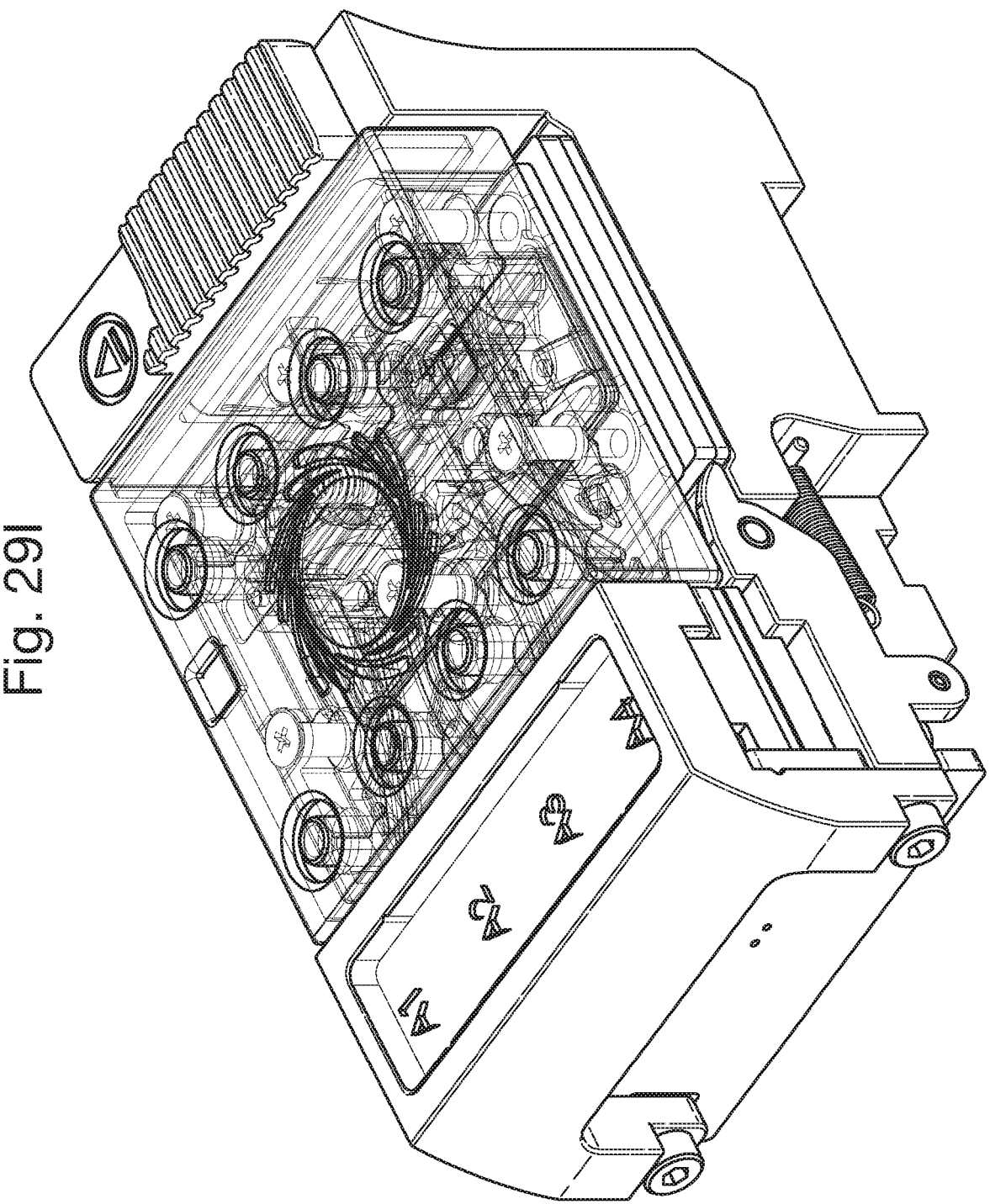
Figure 30A:
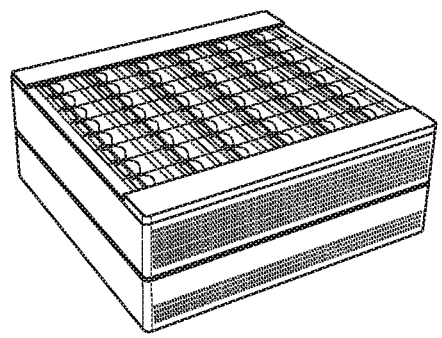
Figure 30B:
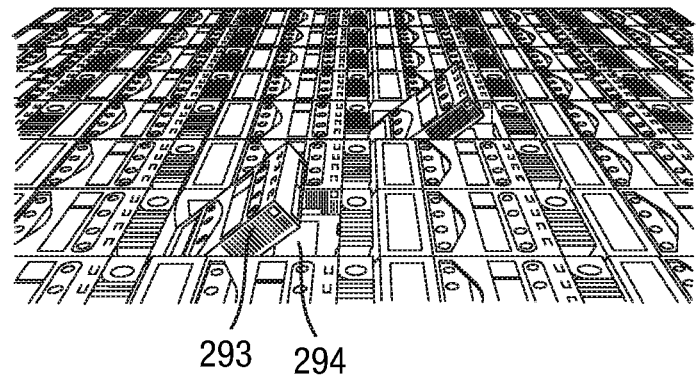
Figure 31A:
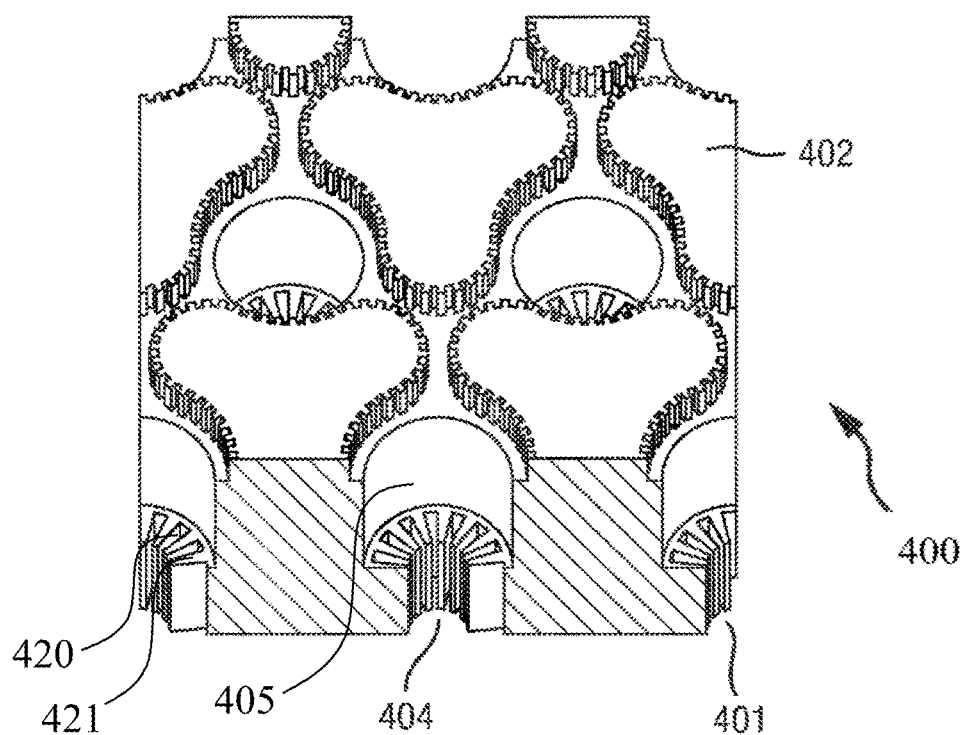
Figure 31B:
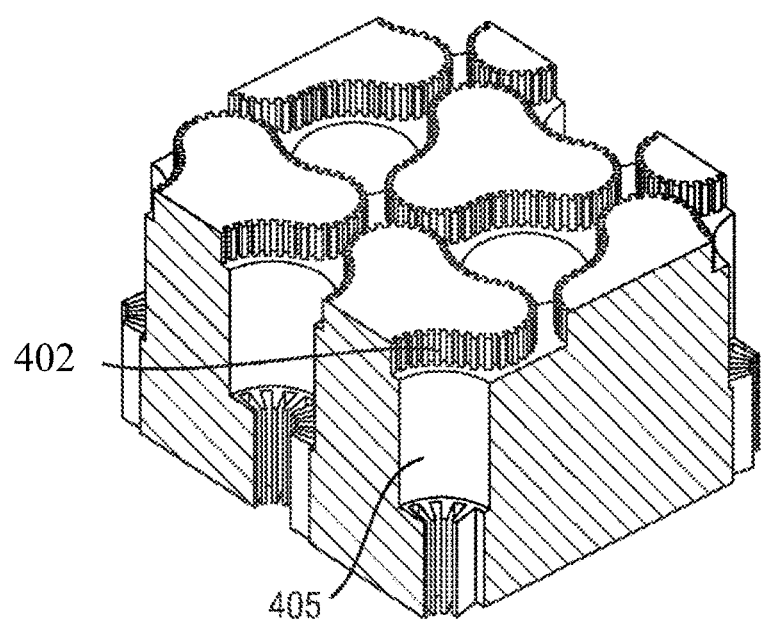
Figure 32:
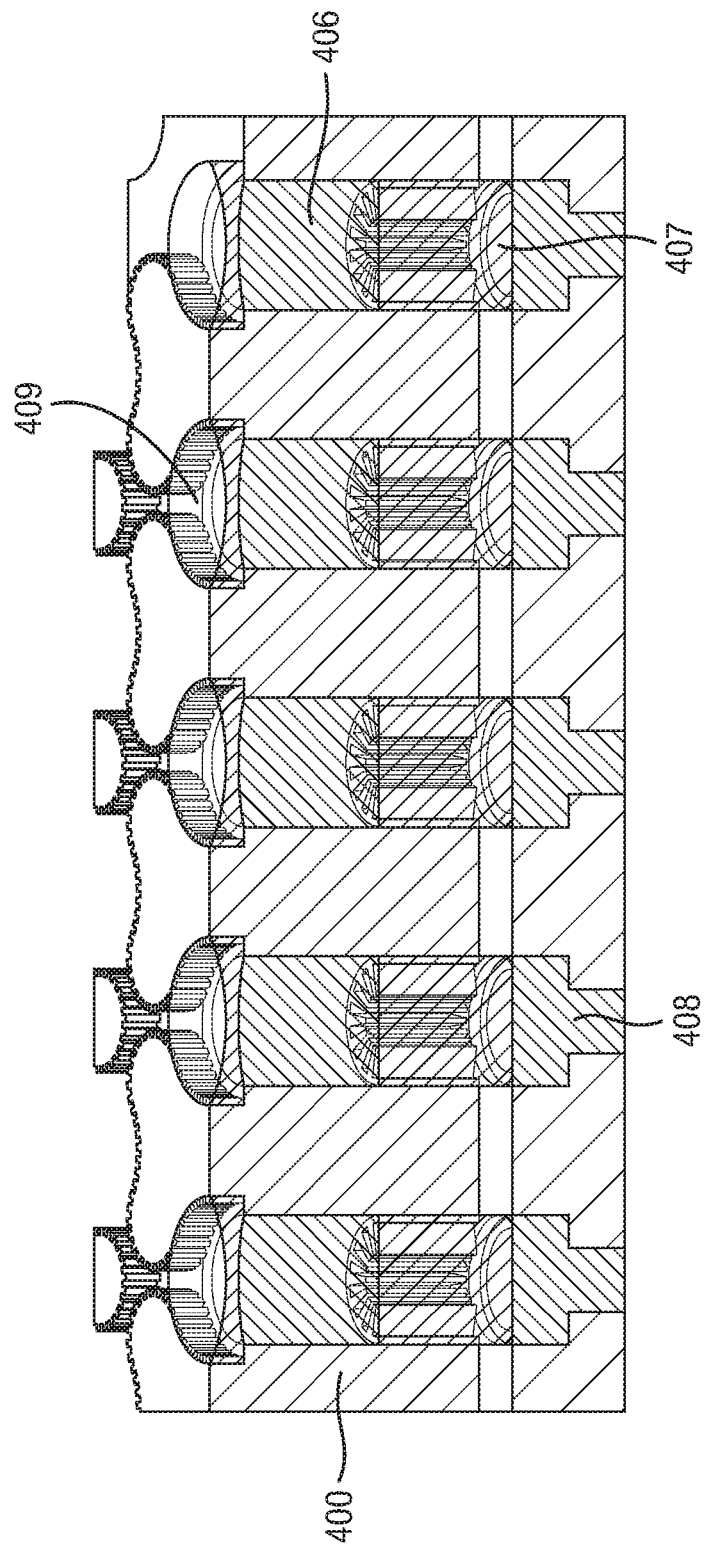
Figure 33B:
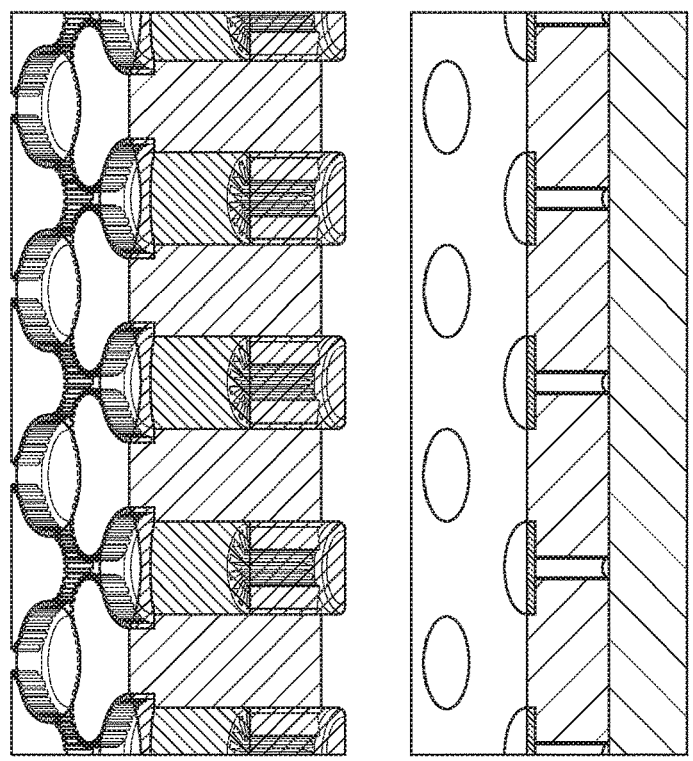
Figure 33A:
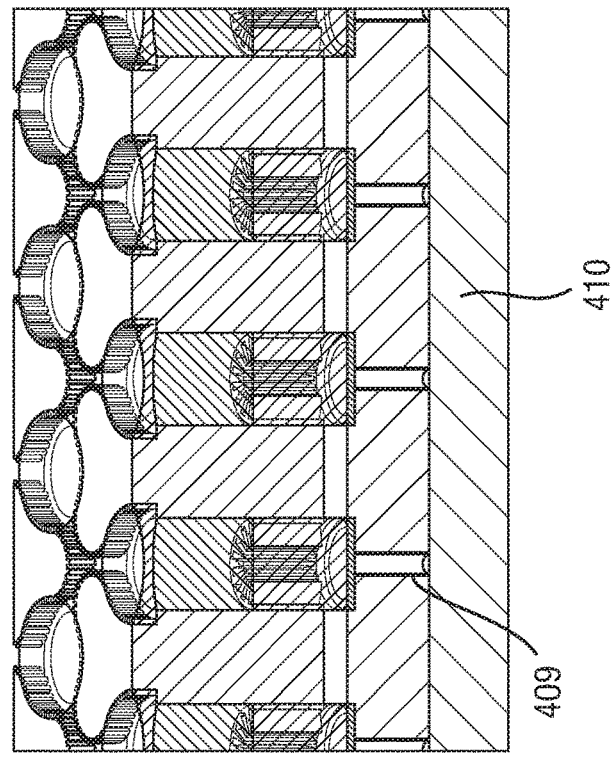
Figure 34:
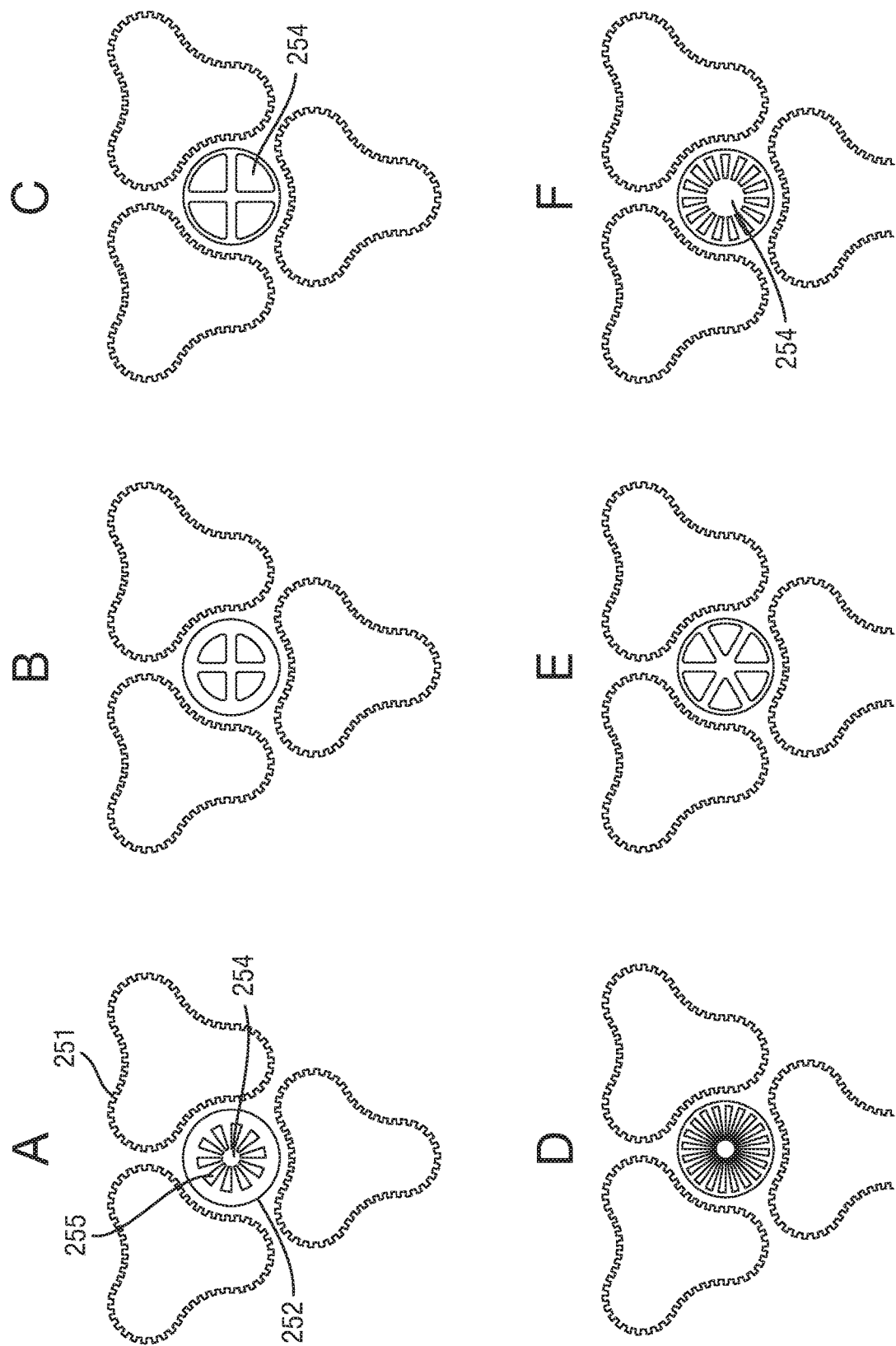
Figure 36:
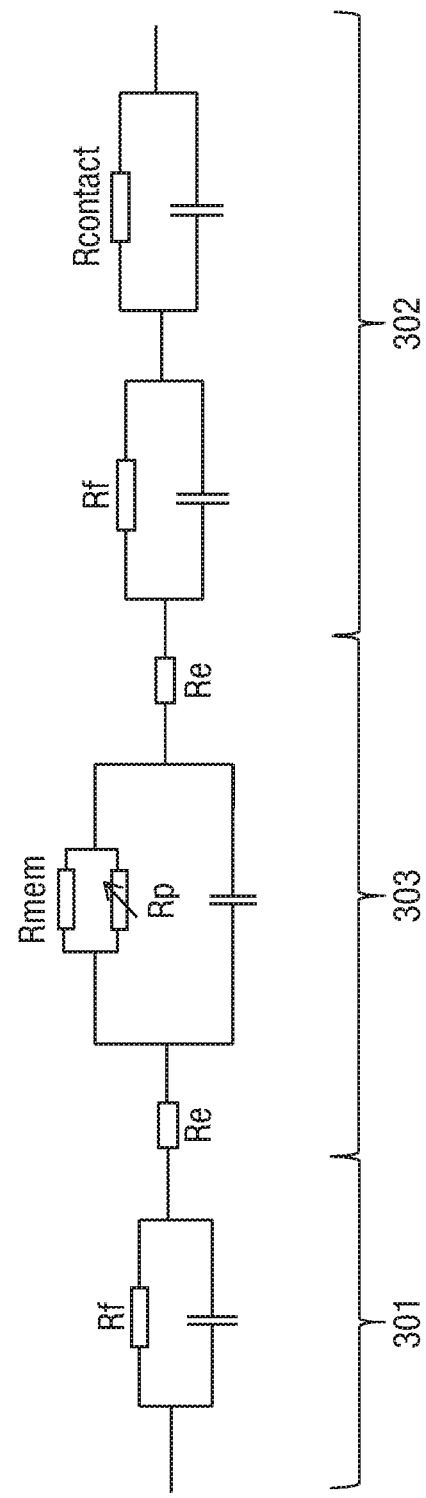

FIG. 27 schematically illustrates the degrees of freedom available to a sphere in different geometries;

FIG. 28 is a picture of an exemplary device comprising component parts;

FIGS. 29A-C are side and isometric views of a further exemplary embodiment device comprising means for aligning the component parts;

FIG. 29D shows an expanded view of detachable component;

FIGS. 29E and F show an expanded view of the flow cell component part of the detachable component of FIG. 29D;

FIGS. 29G and H show respective side and expanded views of the detachable component;

FIG. 29I shows the device with the fluidic pathways and sample entry ports visible;

FIG. 30a shows an analysis instrument comprising an array of detachable component modules;

FIG. 30b shows an expanded view of the modules;

FIGS. 31A and B show projected views of an exemplary body in which the liquid connectors are provided;

FIG. 32 shows an exemplary view of an array of electrical connectors connected to an array of electrodes;

FIGS. 33A and B show the electrical connectors and portion of the chip comprising the array of electrodes in respectively a connected and disconnected state;

FIGS. 34 A-F show exemplary alternative fin designs to that shown in FIGS. 31 A and B;

FIGS. 35A-D show a method of filling a capillary channel;

FIG. 36 shows a circuit diagram of a nanopore device; and

FIGS. 37a and b shows current vs time traces for ion current measurements of translocation of DNA through a nanopore.

The inventors have devised a way of providing an array of electrical connections between component parts of an electrical device in such a way that the component parts can be attached and detached, and optionally reattached thereafter, without requiring extreme conditions (whether chemical or environmental) to trigger the connection or disconnection. By using an array of electrical connectors comprising an electrically conductive liquid, an array of connections can be reliably made without requiring extreme conditions or pressure which could potentially damage a sensitive electrical device, or component part thereof. This is particularly the case with large arrays having a high surface area wherein the pressure required to connect the respective surface areas of the two bodies can be very high. In addition the device may have a number of fragile components such as a suspended amphiphilic layer having a thickness of molecular dimensions.

The ability to detach the array of component parts enables one of the parts, such as that comprising the array of electrical connectors, to be replaced and the other component part, such as that comprising the array of electrodes, to be retained. The array electrode may thereafter be used for connection to a new array of electrical connectors.

Figure 1:
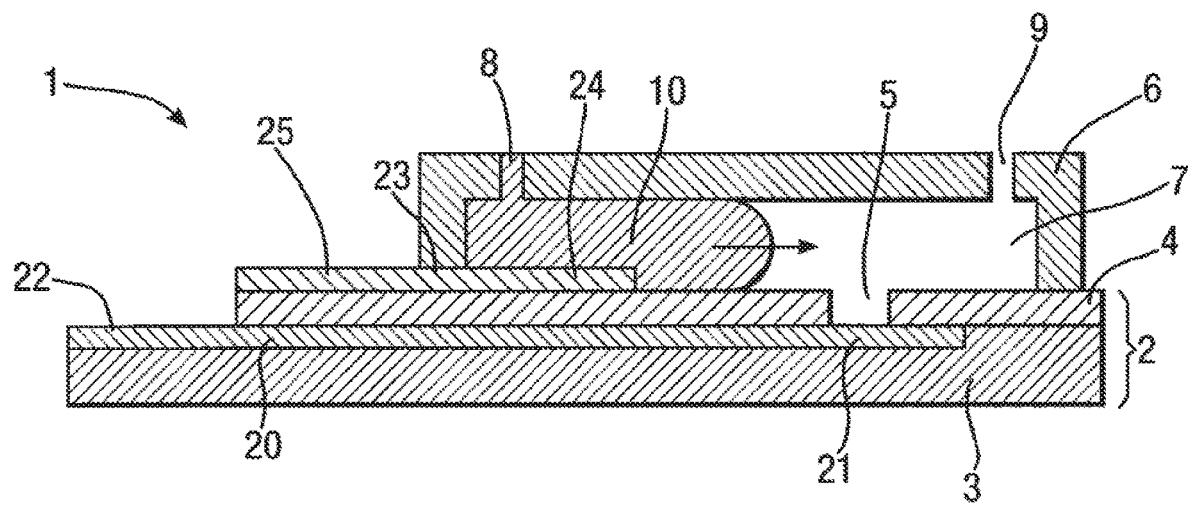
FIG. 1 is a cross sectional view of a prior art apparatus.
Figure 2:
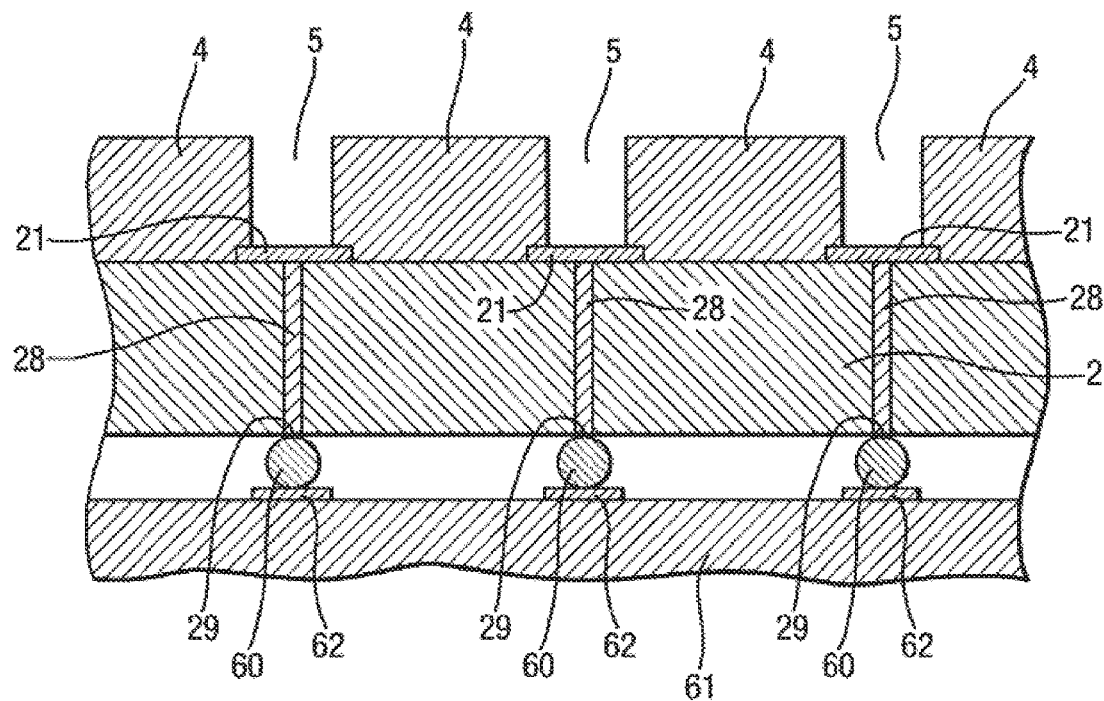
FIG. 2 is a cross sectional view of a prior art apparatus.
Figure 3:
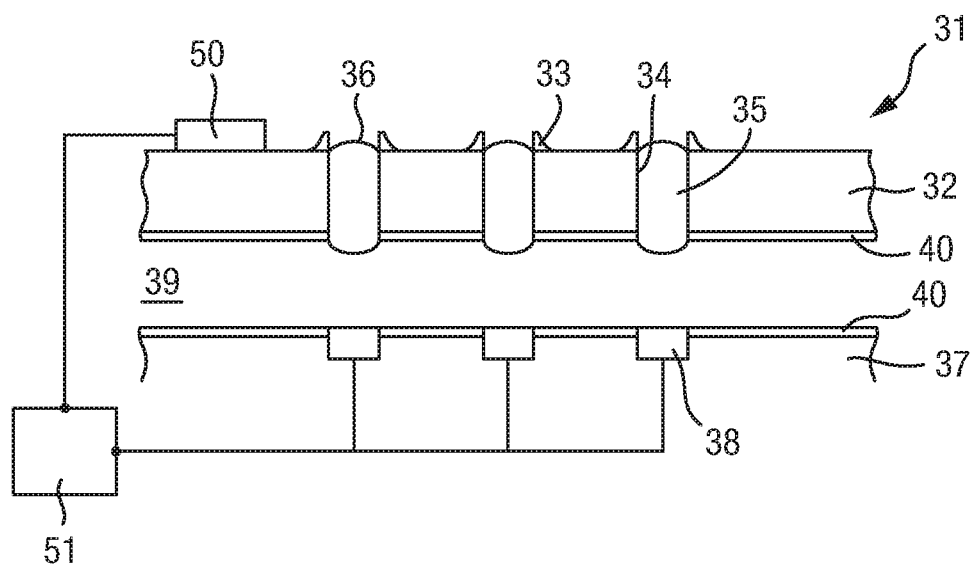
FIG. 3 is a cross sectional view of an electrical device, with two component bodies separated from each other.

FIG. 3 shows two bodies 32 and 37 which represent component parts of an electrical device 31 wherein the component parts may be connected to provide a plurality of electrical connections. The component parts can be provided as a kit, for connection to each other to provide a detachable electrical device.

A body 32 has two parallel surfaces. However, the body does not necessarily need to have parallel surfaces. The body 32 can be made of any suitable material. As discussed in detail below, such materials must be able to have capillaries 34 formed therein. It is also desirable for the material to have hydrophilic characteristics, to assist with filling the capillaries 34, as also discussed further below.

The body 32 and/or 37 may be prepared from a range of different materials having a high electrical resistance, including without limitation, ceramic, un-doped crystalline silicon (i.e. a silicon wafer), SU8, polycarbonate, and/or polyester, glass and including any combination of these or other materials. The body may be manufactured using conventional techniques for such materials, including, without limitation, deposition and removal techniques for example etching, laser processing, moulding or photolithographic techniques.

An array of capillaries 34 is formed in the body 32. The capillaries 34 extend from one surface of the body 32 to the other. The capillaries can have a diameter of around 100 µm, and a pitch of 200 µm or less, for example. Preferably the pitch can be 1 mm or less, more preferably 500 µm or less, further preferably 200 µm or less, further preferably from 100 to 150 µm and even further preferably from 50 to 100 µm. The length of the capillaries may be typically from 100 µm to 1 mm, preferably from 150 µm to 700 µm, and more preferably from 200 µm to 500 µm. However other dimensions may be contemplated. The capillaries can have a circular cross section, but other shapes can also be used. In FIG. 3, an array of capillaries 34 extends through the body 32.

The capillaries 34 are filled with an electrically conductive liquid. The liquid filled capillaries form electrical connectors 35. That is, an array of electrical connectors 35 is disposed in the array of capillaries 34. The liquid connectors extend from one side of the body 32, through the body 32, and to the opposite surface of the body 32. The volume of the electrical liquid in the capillary may be increased by increasing the length of the capillary. Increasing the volume is advantageous in that it enables a larger amount of the soluble redox couple to be provided in the liquid which increases the potential electrochemical lifetime of the apparatus.

FIG. 36 shows a partial circuit diagram representation of a device comprising electrodes 301 and 302 of the first and second components, wherein the electrodes are connected by an ionic solution or ionic liquid through a highly resistive nanopore provided in a resistive membrane. The partial circuit may be considered as an RC circuit where $R_p$ represents the pore resistance, $R_{mem}$ represents the membrane resistance, $R_e$ represents respectively the resistance of the electrode connector and of the fluid sample provided on either side of the membrane, and $R_f$ is the resistance between the fluid sample and the electrode connector. The value of $R_e$ may vary depending upon the ion concentration but will generally be minimal compared to the interface resistance or the pore resistance.

There is an additional contact resistance $R_e$ between the electrode connector and an electrode of the array, shown in an embodiment in series in FIG. 36. The pore resistance $R_p$ may vary depending upon the nature of the analyte that is translocating the pore and upon the extent to which the flow of ions through the pore is restricted. For example during translocation of DNA through an MspA nanopore, the pore resistance may increase by 2 or 3 fold. Each electrode as well as the nanopore membrane has an associated capacitive component. The interface resistance $R_i$ between the electrical connector and electrode of the array is a function of both $R_e$ and Rf. The contact resistance and therefore the associated capacitive component may vary due to the variation in contact between the electrode connector and an electrode of the array. This is in part due to the surface area of contact between the electrical connector and electrode of the array to be connected. Particularly in the case of gel electrical connectors, the extent of contact will depend upon the dimensions of the gel protrusion, for example its shape and depth. The extent of contact will also be determined by the extent of compression of the gel protrusions as the overall variation in height of the surfaces of the component parts to be contacted. It is also dependent upon the resistance at the electrode surface, which may vary due to surface oxidation or surface contaminants.

Although the interface resistance is relatively high and may vary, it is much lower than the pore resistance and as such has minimal effect. Consequently the capacitance at the electrical connector/electrode interface has minimal effect and can be effectively ignored. As such the RC time constant tau (τ) at the interface to be connected, where;

$$\tau = RC$$

is minimal.

By contrast, if the interface resistance is a significant component of the overall circuit resistance, then tau, which represents the time to charge the capacitor through the resistor, also becomes significant. A typical value for the nanopore membrane capacitance is 4 pF whereas the interface capacitance may be much larger, for example 20 pF for an electrode of 100 µm diameter. Thus when the interface capacitance is taken into account, the RC component becomes significant and measurement of the current signal becomes frequency dependent. This is an important factor when measuring current signals at high frequencies as high frequency components of the current signal may be lost. For example in the measurement of the translocation of DNA through a nanopore, the ability to resolve individual k-mers based on the measured current signal level may be reduced. The capacitance at the membrane may differ in value depending upon the type of membrane, for example whether it is solid state or an amphipathic layer. For a solid state membrane, the associated capacitance may be minimal. The RC component representing the contact resistance is shown in series in FIG. 36. It may also be represented in parallel depending upon the type of contact with the electrode surface, namely for example whether the gel contacts the electrode through a uniform resistive layer or whether the resistive layer is only partially present and it contacts the electrode surface directly as well as via a resistive layer. The electrically conductive liquid preferably comprises an ionic liquid or an ionic solution. Ionic liquids are particularly preferable for use as the liquid in the liquid connectors 35, due to their low vapour pressure. As such, they evaporate into a surrounding atmosphere only very slowly, and can therefore be used to provide long lasting connectors 35. Suitable examples of ionic liquids include 1-Ethyl-3-methylimidazolium bis(trifluoromethylsulfonyl)imide (EMIM TFSI), 1-Ethyl-3-methylimidazolium tetrafluoroborate (EMIMBF4), 1-Butyl-3-methylimidazolium tetrafluoroborate (BMIM BF4) and 1-Ethyl-3-methylimidazolium dicyanamide (EMIM DCA).

However, any suitable conductive liquid may be used. In particular, for application in nanopore systems, only very small currents need to be passed by the liquid connectors (which may be of the order of pA). As such, it is possible to have liquid connections of high resistance (i.e. and therefore of relatively poor conductivity), because there is even greater resistance in the rest of the electrical system, namely the resistance across the nanopore, which may be of the order of GΩ, possibly several GΩ.

Optionally, the liquid connectors 35 can be cross-linked, so as to form a gel. This improves the structural integrity of the connectors, thereby improving performance for multiple reconnections (as discussed in further detail below). Such cross linking can be achieved by well-known processes, such as UV cross-linking or chemical cross-linking.

As illustrated in FIG. 3, the liquid connector 35 may project beyond one or both of the surfaces of body 32. In particular, it is preferable for the liquid connector 35 to project from the surface facing the other component forming the electrical device 31 (i.e. the lower surface of the body 32 in FIG. 3), to assist with providing a good electrical connection.

The liquid electrical connectors 35, particularly when in the form of a gel, can project 100 μm or less, 50 μm or less, or further optionally 30 μm or less for a capillary of width 100 μm. As such, they protrude away from the body 32, allowing a good connection with electrodes 38 to be made when bodies 32 and 37 are brought into contact. In order to ensure that the connections between liquid connectors 35 and electrodes 38 in body 37 are one to one (i.e. that there is no spreading of a liquid connector 35 to contact more than one electrode 38), various strategies can be employed, if required. Essentially, these strategies amount to providing some form of flow barrier to substantially prevent the flow of the electrically conductive liquid from the liquid connector 35 and between the electrodes 38, when the electrical connections are formed.

One such method is to provide an electrically insulating fluid such as a silicone oil in the gap 39 between the two bodies 32 and 37 before they are brought into contact. The fluid medium can be provided on the surface of the second body 37 and may be displaced from the surface of the electrodes 38 of the array of electrodes by contact between the electrodes 38 and the electrically conductive liquid of the electrical connectors 35. The fluid therefore acts as an insulating layer, providing insulation between the individual connections after the two layers have been brought together. The fluid therefore provides a dual effect, it provides a physical barrier to help prevent the flow of the electrically conducting liquid, and it further provides an additional insulating effect between the individual connections after they have been made.

Another way of providing a flow barrier is to treat the surfaces of at least one of the bodies 32 and 37 (i.e. the lower surface of body 32 and the upper surface of body 37 in FIG. 3) that are brought together to make the electrical contact, to discourage the flow of the electrically conductive liquid. This can be done by treating the surfaces to be hydrophobic relative to the surface of the electrodes. As such, the electrically conductive liquid 35 is discouraged from spreading beyond the electrodes themselves.

In some cases, it may be possible to select the material of body 32 to encourage suitable behaviour of the liquid within the capillaries 34. For example, it may be desirable for the material of body 32 to be hydrophilic, to assist with filling the capillaries 34 (as discussed below). However, the body could be formed of multiple individual layers, such than an outer layer at the lower surface of body 32 is hydrophobic, to discourage spreading of the conductive liquid beyond the opening of the capillaries 34, whilst the main bulk of body 32 is made of a hydrophilic material which can assist with filling the capillaries 34 (e.g. from the upper surface).

As already mentioned, the liquid connectors 35 are intended to provide electrical connections to a corresponding array of electrodes 38, in a second body 37. The electrodes 38 are provided at the surface of the second body 37. As shown in FIG. 3, the arrangement of the electrodes 38 in body 37 mirrors the arrangement of capillaries 34 in body 32. That is, the electrodes 38 in body 37 are arranged on the same pitch as the capillaries in body 32. Also, the number of electrodes 38 is equal to the number of electrical connectors 35. The number of electrodes 38 in the array of electrodes, and the corresponding number of electrical connectors 35, can be greater than 100, optionally greater than 1000, further optionally greater than 10,000, and further optionally greater than 100,000.

Figure 4:
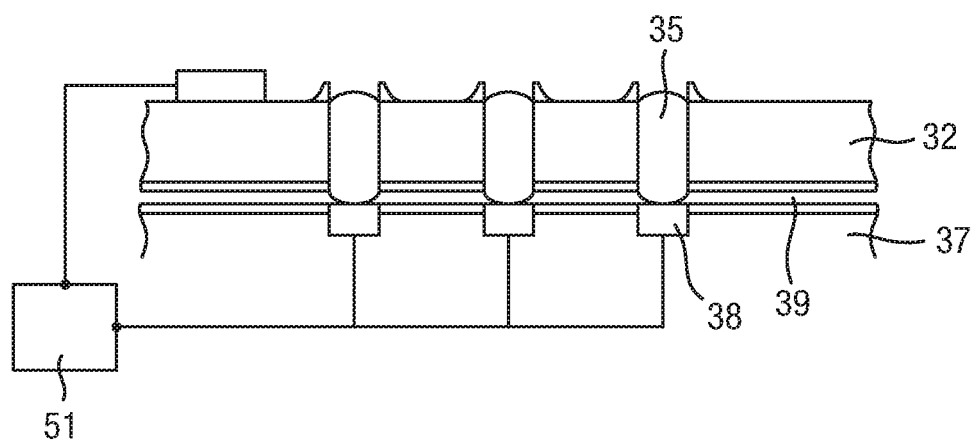
FIG. 4 is a cross sectional view of the electrical device of FIG. 3, with the two component bodies brought together to form an electrical connection.

The surface of body 32, from which the electrical connectors 35 project, can be brought into contact or near proximity with the upper surface of body 37, in which the electrodes 38 are provided, such that each liquid connector 35 individually contacts with one electrode 38 on body 37. To assist with reliably making all the connections across the arrays, the surface of first body 32, from which the electrical connectors 35 project, and the surface of second body 37, in which the electrodes 38 are provided, are preferably planar or have the same surface topography. The formation of the connections is shown in FIG. 4.

The body 37 may comprise an integrated circuit, for example, such as an ASIC (application specific integrated circuit) or an FPGA (field programmable gate array). The electrodes 38 of the body 37 may be connections to such an integrated circuit. That is, the electrodes 38 may be connected to the integrated circuit by connectors that extend from the electrodes into the second body 37. As such the cost of goods of the component part comprising the ASIC may be far more than the component part comprising the array of capillaries.

As such, body 37 may form part of an analysis or measurement device, or any device for characterising an analyte. The electrical device depicted in FIG. 3 is a measurement system, in particular a nanopore system for taking measurements from polymer molecules.

The polymer analyte to be determined may be added to the device so that it contacts the array of nanopores and is in electrical contact with the one or more electrodes of the first body. The polymer may be caused to pass through a nanopore under a potential established between the common electrode of the first body and the array of electrodes of the second body. The potential difference may be a value between 50 mV and 2V, more typically between 100 mV and 300 mV.

Figure 11:
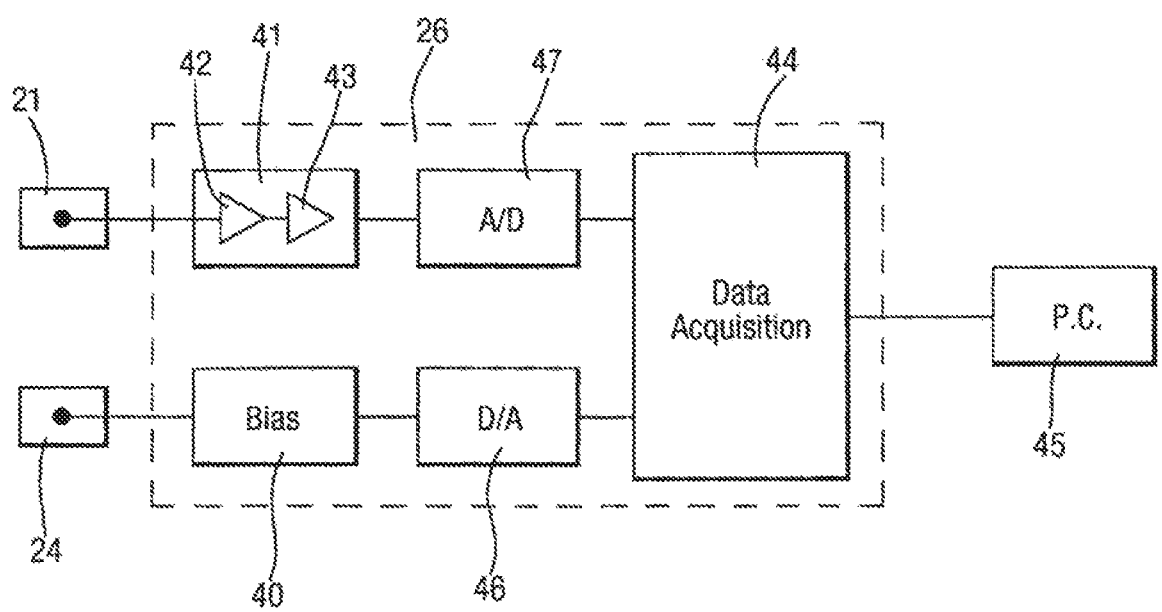
FIG. 11 shows an example design of an electrical circuit.

An example design of the electrical circuit 26 is shown in FIG. 11. The primary function of the electrical circuit 26 is to measure the electrical current signal developed between the common electrode first body and an electrode of the electrode array. This may be simply an output of the measured signal, but in principle could also involve further analysis of the signal. The electrical circuit 26 needs to be sufficiently sensitive to detect and analyse currents which are typically very low. By way of example, an open membrane protein might typically pass current of 100 pA to 200 pA with a 1 M salt solution.

In this implementation, the electrode 24 is used as the array electrode and the electrode 21 is used as the common electrode. Thus the electrical circuit 26 provides the electrode 24 with a bias voltage potential relative to the electrode 21 which is itself at virtual ground potential and supplies the current signal to the electrical circuit 26.

The electrical circuit 26 has a bias circuit 40 connected to the electrode 24 and arranged to apply a bias voltage which effectively appears across the two electrodes 21 and 24.

The electrical circuit 26 also has an amplifier circuit 41 connected to the electrode 21 for amplifying the electrical current signal appearing across the two electrodes 21 and 24. Typically, the amplifier circuit 41 consists of a two amplifier stages 42 and 43.

The input amplifier stage 42 connected to the electrode 21 converts the current signal into a voltage signal.

The input amplifier stage 42 may comprise a transimpedance amplifier, such as an electrometer operational amplifier configured as an inverting amplifier with a high impedance feedback resistor, of for example 500 MΩ, to provide the gain necessary to amplify the current signal which typically has a magnitude of the order of tens to hundreds of pA.

Alternatively, the input amplifier stage 42 may comprise a switched integrator amplifier. This is preferred for very small signals as the feedback element is a capacitor and virtually noiseless. In addition, a switched integrator amplifier has wider bandwidth capability. However, the integrator does have a dead time due to the necessity to reset the integrator before output saturation occurs. This dead time may be reduced to around a microsecond so is not of much consequence if the sampling rate required is much higher. A transimpedance amplifier is simpler if the bandwidth required is smaller. Generally, the switched integrator amplifier output is sampled at the end of each sampling period followed by a reset pulse. Additional techniques can be used to sample the start of integration eliminating small errors in the system.

The second amplifier stage 43 amplifies and filters the voltage signal output by the first amplifier stage 42. The second amplifier stage 43 provides sufficient gain to raise the signal to a sufficient level for processing in a data acquisition unit 44. For example with a 500 MΩ feedback resistance in the first amplifier stage 42, the input voltage to the second amplifier stage 43, given a typical current signal of the order of 100 pA, will be of the order of 50 mV, and in this case the second amplifier stage 43 must provide a gain of 50 to raise the 50 mV signal range to 2.5V.

The electrical circuit 26 includes a data acquisition unit 44 which may be a microprocessor running an appropriate program or may include dedicated hardware. In this case, the bias circuit 40 is simply formed by an inverting amplifier supplied with a signal from a digital-to-analog converter 46 which may be either a dedicated device or a part of the data acquisition unit 44 and which provides a voltage output dependent on the code loaded into the data acquisition unit 44 from software. Similarly, the signals from the amplifier circuit 41 are supplied to the data acquisition card 40 through an analog-to-digital converter 47.

The various components of the electrical circuit 26 may be formed by separate components or any of the components may be integrated into a common semiconductor chip. The components of the electrical circuit 26 may be formed by components arranged on a printed circuit board. In order to process multiple signals from the array of electrodes the electrical circuit 26 is modified essentially by replicating the amplifier circuit 41 and A/D converter 47 for each electrode 21 to allow acquisition of signals from each recess 5 in parallel. In the case that the input amplifier stage 42 comprises switched integrators then those would require a digital control system to handle the sample-and-hold signal and reset integrator signals. The digital control system is most conveniently configured on a field-programmable-gate-array device (FPGA). In addition the FPGA can incorporate processor-like functions and logic required to interface with standard communication protocols i.e. USB and Ethernet. Due to the fact that the electrode 21 is held at ground, it is practical to provide it as common to the array of electrodes.

In such a system, polymers such as polynucleotides or nucleic acids, polypeptides such as a protein, polysaccharides or any other polymers (natural or synthetic) may be passed through a suitably sized nanopore. In the case of a polynucleotide or nucleic acid, the polymer unit may be nucleotides. As such, molecules pass through a nanopore, whilst the electrical properties across the nanopore are monitored and a signal, characteristic of the particular polymer units passing through the nanopore, is obtained. The signal can thus be used to identify the sequence of polymer units in the polymer molecule or determine a sequence characteristic. The one or more characteristics are preferably selected from one or more of (i) the length of the polynucleotide, (ii) the identity of the polynucleotide, (iii) the sequence of the polynucleotide, (iv) the secondary structure of the polynucleotide and (v) whether or not the polynucleotide is modified.

The polymer may be a polynucleotide (or nucleic acid), a polypeptide such as a protein, a polysaccharide, or any other polymer. The polymer may be natural or synthetic. The polymer units may be nucleotides. The nucleotides may be of different types that include different nucleobases.

The polynucleotide may be deoxyribonucleic acid (DNA), ribonucleic acid (RNA), cDNA or a synthetic nucleic acid known in the art, such as peptide nucleic acid (PNA), glycerol nucleic acid (GNA), threose nucleic acid (TNA), locked nucleic acid (LNA), bridged nucleic acid (BNA) or other synthetic polymers with nucleotide side chains. The polynucleotide may be single-stranded, be double-stranded or comprise both single-stranded and double-stranded regions. Typically cDNA, RNA, GNA, TNA or LNA are single stranded.

The methods described herein may be used to identify any nucleotide. The nucleotide can be naturally occurring or artificial. A nucleotide typically contains a nucleobase (which may be shortened herein to "base"), a sugar and at least one phosphate group. The nucleobase is typically heterocyclic. Suitable nucleobases include purines and pyrimidines and more specifically adenine, guanine, thymine, uracil and cytosine. The sugar is typically a pentose sugar. Suitable sugars include, but are not limited to, ribose and deoxyribose. The nucleotide is typically a ribonucleotide or deoxyribonucleotide. The nucleotide typically contains a monophosphate, diphosphate or triphosphate.

The nucleotide can include a damaged or epigenetic base. The nucleotide can be labelled or modified to act as a marker with a distinct signal. This technique can be used to identify the absence of a base, for example, an abasic unit or spacer in the polynucleotide.

Of particular use when considering measurements of modified or damaged DNA (or similar systems) are the methods where complementary data are considered. The additional information provided allows distinction between a larger number of underlying states.

The polymer may also be a type of polymer other than a polynucleotide, some non-limitative examples of which are as follows.

The polymer may be a polypeptide, in which case the polymer units may be amino acids that are naturally occurring or synthetic.

The polymer may be a polysaccharide, in which case the polymer units may be monosaccharides.

Examples of polymer hydrogels that may be used in the invention include polyvinyl alcohol (PVA), gelatin, agarose, methylcellulose, hyaluronan, polyacrylamide, silicone hydrogels, polyethylene oxide, polyAMPS, polyvinylpyrrolidone, polysaccharides and poly(ethylene glycol) dimethacrylate. The hydrogel may be homopolymeric, copolymeric or a multipolymer interpenetrating polymeric network (IPN). The hydrogel may be UV curable. Crosslinking by UV polymerisation to form a gel is particularly advantageous as the cross-linking to form the gel may be carried out at room temperature without the need to heat the liquid or add a chemical reactant. In the case that the electrically conducting liquid is a gel, it may be conveniently added to the capillaries in the form of a liquid and subsequently solidified.

The electrodes of the array and/or the one of more electrodes of the first body are preferably formed of an inert material such as platinum, palladium, gold or carbon.

A redox couple may be provided in the ionic flow path which serves to maintain the potential difference between the one or more electrodes of the first body and the electrodes of array. The redox couple may be provided in the capillary flow path and/or the droplets on the surfaces of the electrode array. Alternatively the electrodes may themselves comprise a redox couple such as Ag/AgCl and Cu—CuSO4.

In a nanopore system, such a device can monitor the electrical activity across pores provided in a series of wells. In FIG. 3, the wells are provided as recesses 36 above the connector-filled capillaries 34. That is, the recesses 36 can be provided on the body 32, and each well recess 36 is connected to a capillary 34. In FIG. 3, body 32 acts as a support for a well wall 33. Well wall 33 may be provided as a separate layer on body 32 (e.g. constructed through lithographic techniques). In other arrangements, a separate well wall may not be present, with the well recess being formed directly in the body 32, perhaps as the top of a capillary (and, in that case, the liquid connectors 35 would not fill the entire capillary 34).

In nanopore systems, the nanopore is a pore, typically having a size of the order of nanometres. The nanopore may be a biological pore or a solid state pore. Examples of biological pores may be transmembrane protein pores. In the example of FIG. 3, biological nanopores are present in an amphiphilic layer formed across a well recess 36. In contrast, a solid state pore is typically an aperture in a solid state layer. In either case, the nanopore is provided in an insulating substrate provided across each capillary 34, and thus across ionic flowpath (mentioned below) when the system is in use. As such, current is passed through the nanopores.

As mentioned above, a signal between two electrodes either side of the nanopore is monitored. In FIG. 3, this arrangement is shown schematically by the provision of a common electrode 50, on the upper surface of body 32, and the sequence of individual electrodes 38 in body 37. In practice, the common electrode may connect through the bottom of body 32 (although it is shown on top of body 32 in FIG. 3 for clarity), to ease connection to the rest of the electrical circuit, which is formed at least partly in body 37. Alternatively, instead of a single common electrode 50, the first body 32 may comprise more than one electrode 50.

In use, a sample liquid comprising the analyte of interest to be determined would be provided over the upper surface of body 32, providing an electrical connection between each well and the common electrode 50. Further, an electrical path is formed through the liquid connector 35 and to electrode 38 on the other side of the nanopore supported in each well recess 36. That is, there is a plurality of capillary ionic flow paths between the one or more electrodes 50 and the electrodes 38 of the array of electrodes, when the electrical connections are formed. As such, current is passed between the electrically conductive liquid and the one or more electrodes 50 through the nanopores.

Figure 21:
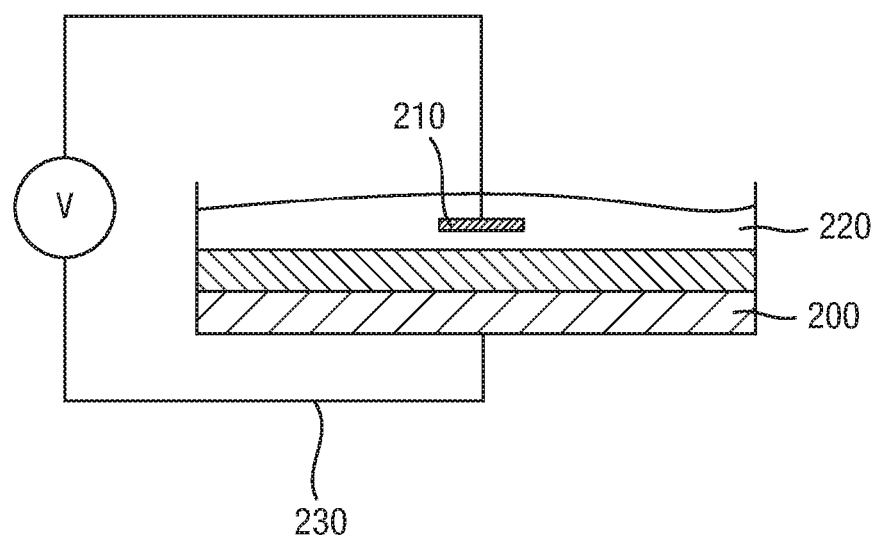
FIG. 21 is a schematic view of an analytical device.

This is shown schematically in FIG. 21 wherein a circuit 230 connects the electrodes of the array (not shown) of the connected device 200 with the common electrode 210. In use, liquid sample 220 is added to the device and as in electrical contact with the common electrode 210. The common electrode may be separated from the sample by a frit. This avoids any potential contamination of the sample with the common electrode, which may be for example a reference electrode such as Ag/AgCl.

As such, the current passed between the common electrode 50 and any individual electrode 38 is indicative of the electrical activity within the corresponding individual well recess formed on body 32. As such, a suitable analysis unit (depicted schematically by element 51 in FIG. 3) can interpret such data accordingly.

As mentioned above, the resistance in a nanopore circuit is typically very large. For example, the resistance between electrodes 50 and 38 can be greater than 1 kΩ, even greater than 1 MΩ, even greater than 100 MΩ, and even greater than 1 GΩ. As such, even a relatively large resistance in the electrical connectors 35 is relatively insignificant in the overall analysis system. As such, the use of liquid connectors in such systems does not pose a problem from the point of view of their high resistance, compared to e.g. solid state electrical connections. Indeed, the interface resistance between the liquid connectors 35 and electrodes 38 of body 37 can be 1% or less, sometimes 0.1% or less, even 0.01% or less or 0.001% or less than the resistance between the electrodes 50 and 38 in a nanopore system.

Electrical measurements may be made using standard single channel recording equipment as describe in Stoddart D et al., Proc Natl Acad Sci, 12;106(19):7702-7, Lieberman K R et al, J Am Chem Soc. 2010;132(50):17961-72, and WO-2000/28312.

In general, when the measurement is current measurement of ion current flow through the pore, the ion current may typically be the DC ion current, although in principle an alternative is to use the AC current flow (i.e. the magnitude of the AC current flowing under application of an AC voltage).

Optical measurements may be combined with electrical measurements (Soni G V et al., Rev Sci Instrum. 2010 Jan;81(1):014301).

The device may take simultaneous measurements of a different nature. The measurement may be of a different nature because they are measurements of different physical properties, which may be any of those described above. Alternatively, the measurements may be of different natures because they are measurements of the same physical properties but under different conditions, for example electrical measurements such as current measurements under different bias voltages.

The one or more electrodes of the first body is typically a common electrode held at ground and the potential difference may be varied by varying the potential at the array of electrodes. The circuit may allow for selective control of the potential at each electrode of the array such that the potential difference may be varied at each sensor nanopore of the array for example, to apply a reverse potential to a nanopore in order to eject a polymer from the pore.

Typically, each measurement taken by the biochemical analysis system is dependent on a k-mer, being k polymer units of the respective sequence of polymer units, where k is a positive integer. Although ideally the measurements would be dependent on a single polymer unit (i.e. where k is one), with many typical types of the biochemical analysis system 1, each measurement is dependent on a k-mer of plural polymer units (i.e. where k is a plural integer). That is, each measurement is dependent on the sequence of each of the polymer units in the k-mer where k is a plural integer.

In a series of measurements taken by the biochemical analysis system, successive groups of plural measurements are dependent on the same k-mer. The plural measurements in each group are of a constant value, subject to some variance discussed below, and therefore form a "level" in a series of raw measurements. Such a level may typically be formed by the measurements being dependent on the same k-mer (or successive k-mers of the same type) and hence correspond to a common state of the biochemical analysis system.

The signal moves between a set of levels, which may be a large set. Given the sampling rate of the instrumentation and the noise on the signal, the transitions between levels can be considered instantaneous, thus the signal can be approximated by an idealised step trace.

FIG. 37a shows a typical current signal over time during translocation of DNA through a nanopore under enzyme control. The signal may be analysed to identify step traces as illustrated by FIG. 37b, which represent individual k-mers within the nanopore.

The measurements corresponding to each state are constant over the time scale of the event, but for most types of the biochemical analysis system will be subject to variance over a short time scale. Variance can result from measurement noise, for example arising from the electrical circuits and signal processing, notably from the amplifier in the particular case of electrophysiology. Such measurement noise is inevitable due to the small magnitude of the properties being measured. Variance can also result from inherent variation or spread in the underlying physical or biological system of the biochemical analysis system. Most types of the biochemical analysis system will experience such inherent variation to greater or lesser extents. For any given types of the biochemical analysis system, both sources of variation may contribute or one of these noise sources may be dominant.

In addition, typically there is no a priori knowledge of number of measurements in the group, this varying unpredictably.

These two factors of variance and lack of knowledge of the number of measurements can make it hard to distinguish some of the groups, for example where the group is short and/or the levels of the measurements of two successive groups are close to one another.

The series of raw measurements may take this form as a result of the physical or biological processes occurring in the biochemical analysis system. Thus, in some contexts each group of measurements may be referred to as a "state".

For example, in some types of the biochemical analysis system, the event consisting of translocation of the polymer through the pore may occur in a ratcheted manner. During each step of the ratcheted movement, the ion current flowing through the nanopore at a given voltage across the pore is constant, subject to the variance discussed above. Thus, each group of measurements is associated with a step of the ratcheted movement. Each step corresponds to a state in which the polymer is in a respective position relative to the pore. Although there may be some variation in the precise position during the period of a state, there are large scale movements of the polymer between states. Depending on the nature of the biochemical analysis system, the states may occur as a result of a binding event in the nanopore.

The duration of individual states may be dependent upon a number of factors, such as the potential applied across the pore, the type of enzyme used to ratchet the polymer, whether the polymer is being pushed or pulled through the pore by the enzyme, pH, salt concentration and the type of nucleoside triphosphate present. The duration of a state may vary typically between 0.5 ms and 3 s, depending on the biochemical analysis system 1, and for any given nanopore system, having some random variation between states. The expected distribution of durations may be determined experimentally for any given biochemical analysis system.

The measurements taken of the polymer may be analysed by a method such as that disclosed in WO2013/041878 or WO2013/121224 in order to characterise the polymer. This analysis may be carried out remotely such as in the cloud or on a PC. Alternatively the device may comprise the data analysis means.

A typical translocation rate of DNA through a nanopore under enzyme control is around 30 bases/second although the rate of translocation may be as much as 1000 bases/second. Thus the measurement system needs to be able to record changes in the current signal over time. The ability to effectively measure the current signal will depend in part upon the ability of the electrodes to respond to changes in current. Thus it is desirable that the RC time component, namely the time taken to charge the double layer capacitor at the solution/electrode interface is low.

The amphiphilic layer may comprise a lipid, which may have a single component or a mixture of components, as is conventional when forming lipid bilayers.

Any lipids that form a lipid bilayer may be used. The lipids are chosen such that a lipid bilayer having the required properties, such as surface charge, ability to support membrane proteins, packing density or mechanical properties, is formed. The lipids can comprise one or more different lipids. The lipids can also be chemically-modified. However such naturally occurring lipids are prone to biological degradation for example by proteins or detergents and are not able to withstand high voltages. Preferably the amphipathic layer is non-naturally occurring. Amphipathic polymer membranes are preferred over lipid membranes due to their ability to withstand higher voltages.

In another example, the amphipathic molecules may comprise an amphipathic compound comprising a first outer hydrophilic group, a hydrophobic core group, and a second outer hydrophilic group, wherein each of the first and second outer hydrophilic groups is linked to the hydrophobic core group. The amphiphilic molecules may be diblock or triblock polymers such as poly(2-methyloxazoline)-block-poly(dimethylsiloxane)-block-poly(2-methyloxazoline) (PMOXA-PDMS-PMOXA). Examples of amphipathic membranes suitable for use in the invention are disclosed in WO2014064444A1.

The membrane may be a solid state layer. Solid state layers can be formed from both organic and inorganic materials including, but not limited to, microelectronic materials, insulating materials such as Si3N4, Al2O3, and SiO2, organic and inorganic polymers such as polyamide, plastics such as Teflon® or elastomers such as two-component addition-cure silicone rubber, and glasses. The solid state layer may be formed from graphene. Suitable graphene layers are disclosed in International Application No. PCT/US2008/010637 (published as WO 2009/035647).

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane pore may be used in the invention. The pore may be biological or artificial. Suitable pores include, but are not limited to, protein pores, polynucleotide pores and solid state pores. The pore may be a DNA origami pore (Langecker et al., Science, 2012; 338: 932-936).

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a triblock copolymer membrane, to the other. The transmembrane protein pore allows a polynucleotide, such as DNA or RNA, to be moved through the pore.

The transmembrane protein pore may be a monomer or an oligomer. The pore is preferably made up of several repeating subunits, such as at least 6, at least 7, at least 8 or at least 9 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as Mycobacterium smegmatis porin (Msp), for example MspA, MspB, MspC or MspD, outer membrane porin F (OmpF), outer membrane porin G (OmpG), outer membrane phospholipase A and Neisseria autotransporter lipoprotein (NalP) and other pores, such as lysenin. α-helix bundle pores comprise a barrel or channel that is formed from α-helices. Suitable α-helix bundle pores include, but are not limited to, inner membrane proteins and outer membrane proteins, such as WZA and ClyA toxin. The transmembrane pore may be derived from lysenin. Suitable pores derived from lysenin are disclosed in International Application No. PCT/GB2013/050667 (published as WO 2013/153359). The transmembrane pore may be derived from Msp or from α-hemolysin(α-HL). The resistance in a nanopore provided in an amphipathic layer separating two ionic media may be easily calculated from measurements of ion current flow under a potential difference applied across the pore. The resistance will vary depending upon the internal dimensions of the pore channel, the potential difference applied as well as the ion mobility. A typical value for α-hemolysin for a 1 M concentration of aq. KCl translocating the pore under a potential difference of 100 mV is approximately 1 GΩ. MspA nanopores have internal channels of larger dimensions and therefore a greater conductance. The resistance of the channel, depending upon the mutant type, under the same conditions is therefore less, typically of the order of 500 MΩ.

In order to allow measurements to be taken as the polymer translocates through the pore, the rate of translocation can be controlled by a polymer binding moiety. Typically the moiety can move the polymer through the pore with or against an applied field. The moiety can be a molecular motor using for example, in the case where the moiety is an enzyme, enzymatic activity, or as a molecular brake. Where the polymer is a polynucleotide there are a number of methods proposed for controlling the rate of translocation including use of polynucleotide binding enzymes. Suitable enzymes for controlling the rate of translocation of polynucleotides include, but are not limited to, polymerases, helicases, exonucleases, single stranded and double stranded binding proteins, and topoisomerases, such as gyrases. For other polymer types, moieties that interact with that polymer type can be used. The polymer interacting moiety may be any disclosed in WO-2010/086603, WO-2012/107778, and Lieberman K R et al, J Am Chem Soc. 2010;132(50):17961-72), and for voltage gated schemes (Luan B et al., Phys Rev Lett. 2010;104(23):238103).

A polymer binding moiety can be used in a number of ways to control the polymer motion. The moiety can move the polymer through the pore 32 with or against the applied field. The moiety can be used as a molecular motor using for example, in the case where the moiety is an enzyme, enzymatic activity, or as a molecular brake. The translocation of the polymer may be controlled by a molecular ratchet that controls the movement of the polymer through the pore. The molecular ratchet may be a polymer binding protein.

For polynucleotides, the polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the target polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme may be derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in WO-2010/086603.

Suitable strategies for single strand DNA sequencing are the translocation of the DNA through the pore 32, both cis to trans and trans to cis, either with or against an applied potential. The most advantageous mechanism for strand sequencing is the controlled translocation of single strand DNA through the pore 32 under an applied potential. Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential. Alternatively, the single strand DNA dependent polymerases can act as molecular brake slowing down the movement of a polynucleotide through the pore. By way of example, any moieties, techniques or enzymes described in WO-2012/107778, WO-2012/033524, WO-2012/033524, WO 2013/057495 or WO 2014/013260 could be used to control polymer motion.

The redox couple may be soluble or partially soluble in the electrically conducting liquid. Examples of such are ferri/ferrocyanide, ferrocene/ferrocinium, Ru(NH3)6C13 and Ru(LL)(2)(X)(2) where LL are 1,10-phenanthroline or 2,2'-bipyridine type ligands, and X is an acido ligand. Alternatively the redox couple may comprise a metal and its insoluble metal salt, such as an Ag/AgCl. The redox couple may be reference electrode. As a consequence of ion flow between the electrodes, a member of the redox couple is either oxidised or reduced at an electrode (depending upon its polarity) and thus becomes depleted over time, which can limit the lifetime of the device. The extent of depletion will depends upon the magnitude of the current flow. The electrochemical lifetime of the redox couple can be increased by increasing the concentration or amount of the redox couple present. Increasing the length of the capillary channels is a convenient way to increase the amount of the redox couple.

The redox couple can be added to the electrically conducting liquid prior to forming a gel. As an alternative, it can be diffused into the gel. In order to minimise depletion of the redox couple, a third electrode may be provided wherein current flow takes place between two electrodes and the potential difference is maintained between one of the electrodes and the third electrode. Such a system may be referred to as a three electrode system. Practically however, it is more convenient to provide a two electrode system as described herein.

Figure 5:
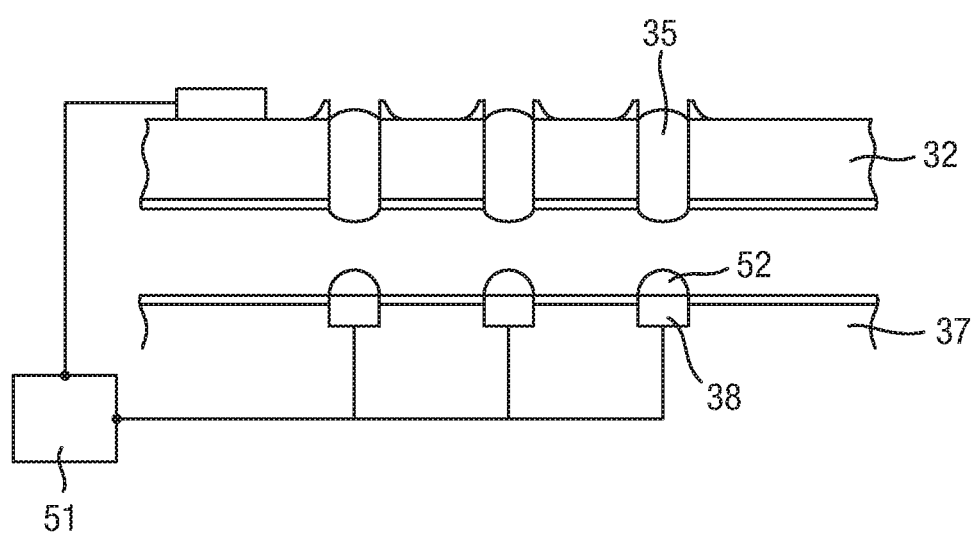
FIG. 5 is a cross sectional view of an alternative arrangement for a connection between component parts of a detachable electrical device.

Reverting to the figures, FIG. 5 shows an example of an alternative arrangement, in which the electrodes 38 of body 37 are also provided with a liquid connector 52. These liquid connectors 52 can be provided as individual droplets on the individual electrodes 38. That is, each droplet 52 is in contact with a single electrode, and does not contact more than one electrode. The droplets 52 may be of the same liquid as in connectors 35 or a different conductive liquid. Once again, the liquid may be gelled. The droplets can have a height of 20 μm or less above the electrodes 38, optionally 10 μm or less, further optionally 5 μm or less.

The droplets 52 can be provided, for example, by providing the electrodes 38 on a surface of body 37 that is suitably hydrophobic, with respect to the electrodes 38, such that when electrically conductive liquid is provided to the surface, droplets 52 naturally form on the electrodes as the most hydrophilic part of the surface.

The presence of the liquid droplets can form a projection beyond the surface of the body 37, and therefore assist in providing a good electrical connection with the connectors 35 of body 32 even, for example, if the surfaces of body 37 and 32 are not perfectly parallel. As such, a high percentage of the capillaries in body 32 can be successfully connected to electrodes 38 in body 37, even in the presence of imperfect surfaces.

Figure 6:
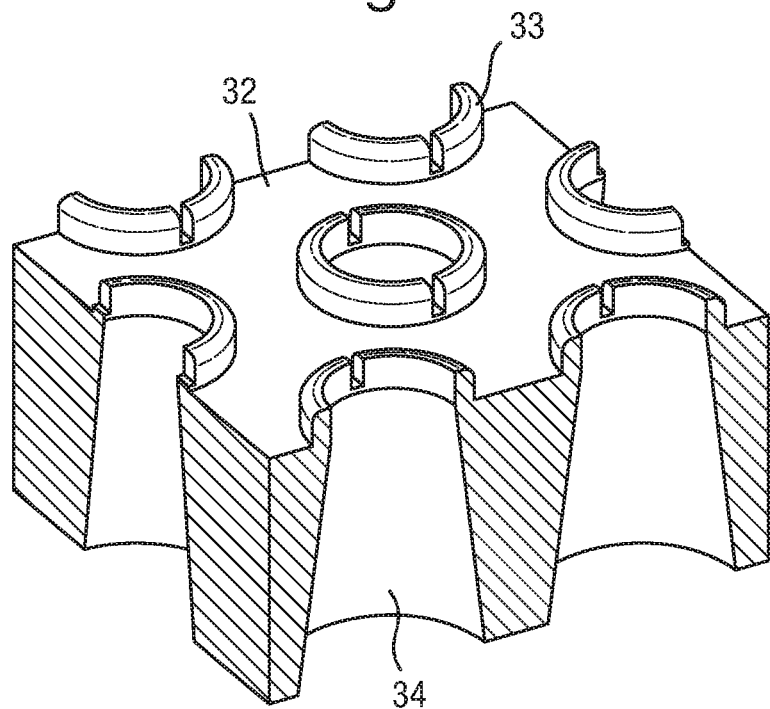
FIG. 6 is a perspective view of an example of capillaries formed within a substrate.
Figure 17:
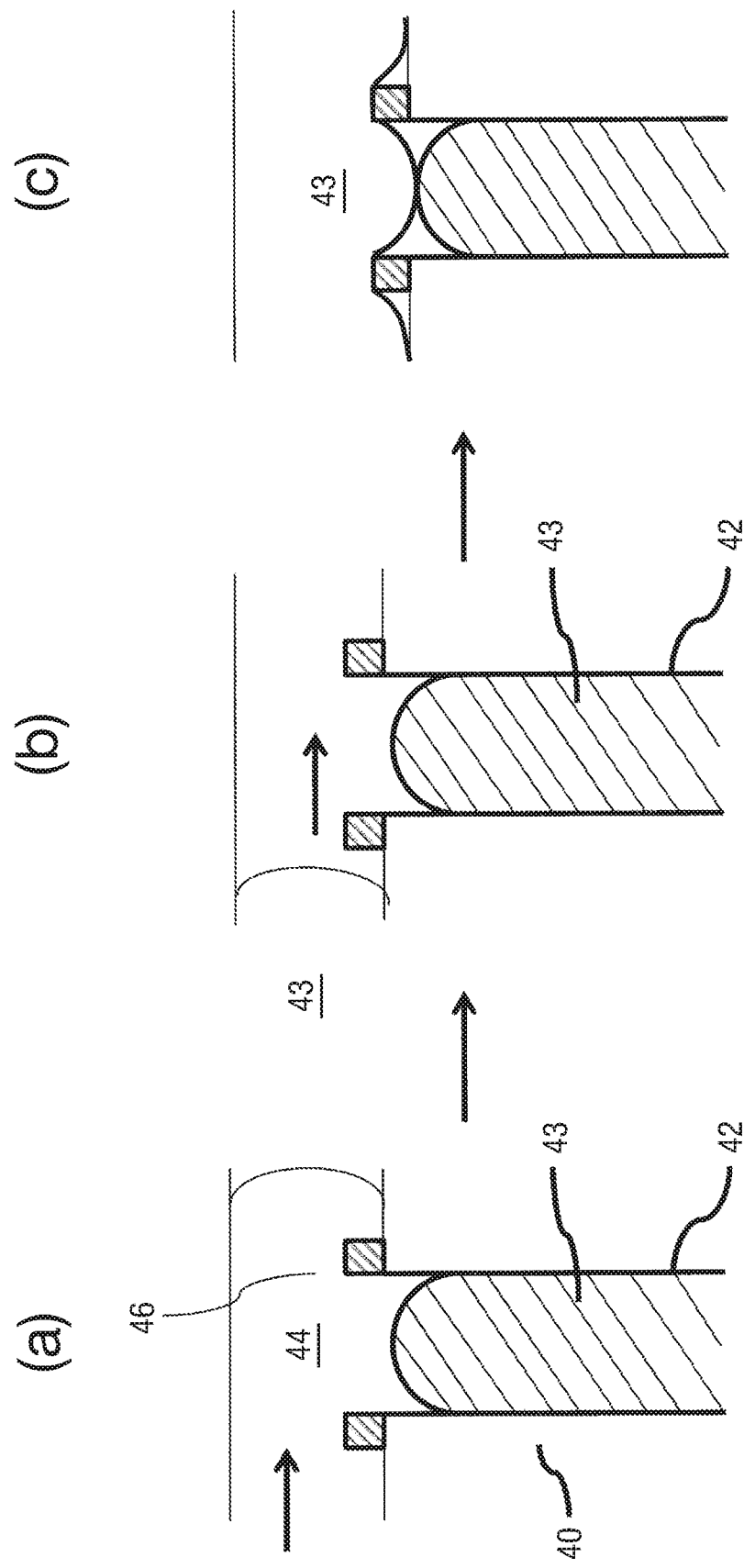
FIG. 17 is a set of schematic side views of the body 32 in successive steps of a method of providing the nanopores and amphiphilic membrane.

FIG. 6 shows a portion of a capillary substrate forming part of a body 32. The substrate may be formed by a standard lithographic process. The substrate may be formed from a variety of materials such as glass, silicon, a curable epoxy-based photolaminate, cyclic olefin copolymer (COC) or a cyclic olefin polymer (COP). The material may be coated, for example silane coated glass, to influence its surface properties in relation to the electrically conductive liquid and for example to control the clipping process discussed below. In this example, the capillary 34 tapers due to the fact that it is formed around a tool which was subsequently removed after curing of the substrate. The castellations shown in FIG. 6 are raised regions formed around the circumference of the entrance to the capillary channel from which the amphiphilic membranes may be suspended, as shown in FIG. 17 (c). Grooves are provided in the region such that it is bisected. The shape of the castellations are not limited however to that shown in FIG. 6 and other shapes may be contemplated.

Figure 7:
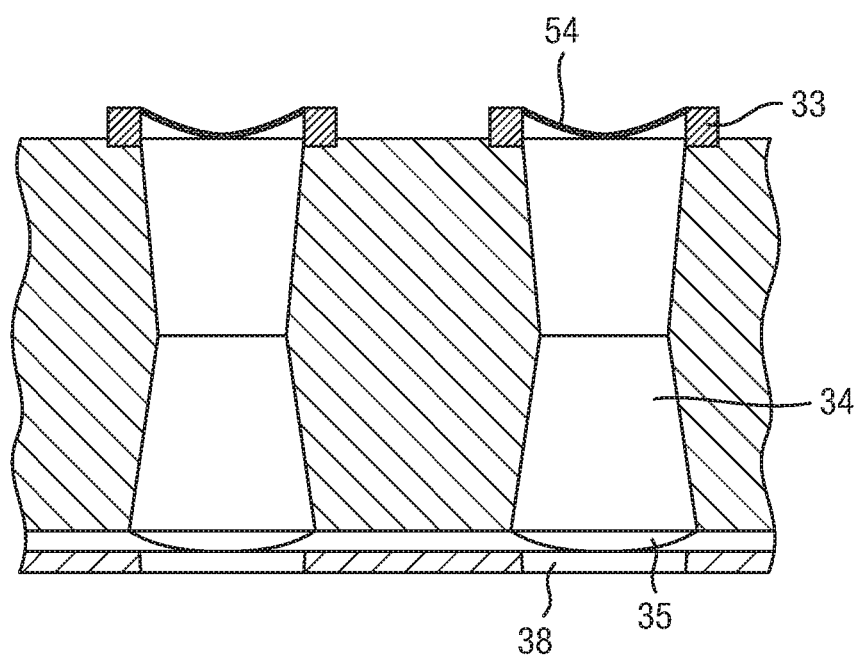
FIG. 7 is cross-section view of capillaries within a substrate.

To counteract the tapering, if desired, two substrates as shown in FIG. 6 can be placed 'back-to-back' to produce capillaries 34 which widen in the middle and narrow towards each surface. Alternatively, the opposite profile can be produced by joining the substrates the other way around: capillaries that thin in the middle and expand towards the surfaces. This is shown in FIG. 7. FIG. 7 also shows the electrical connections formed between the electrically conductive liquid 35 and the electrodes 38. In this example, the liquid has been cross-linked in order to create a gel which reduces any egress from the capillaries 34 and advantageously enables a convex fluid meniscus to extend from the ends of the capillaries. It is important to ensure that membrane 54 remains in electrical contact with the electrically conducting liquid provided within the capillary 34. The use of an ionic liquid over an aqueous based ionic solution is advantageous in that it is less likely to contract or expand due to evaporation of absorption of water. At the ends of the capillaries 34 (on the upper surface as depicted in FIG. 6) are provided castellations, which are one way of providing a well wall 33, on which membranes containing nanopores can be suspended. The capillaries 34 extend to the other end (lower surface) of the substrate so as to provide the electrical connections with the other body 37 (not shown in FIG. 6).

The nanopores and amphipathic membranes may be formed by flowing one or more liquids comprising nanopores and amphipathic molecules across the surface of the body 32 on which the castellations 33 are provided. Suitable methods of providing the nanopores and amphiphilic membranes in an array are disclosed in PCT/GB2013/052766 (published as WO2014064443).

In an example of a possible method as illustrated in FIG. 17, the capillary channel 42 is filled with the electrically conducting liquid 43. An apolar liquid 44 immiscible with the electrically conducting liquid and comprising the amphiphilic molecules is flowed over the surface of the body 40 as shown in (a). Flow over the surface of the body may take place in a flow cell. The liquid is subsequently displaced by flowing a polar medium 43 over the surface of the body which clips the liquid 44 such that a layer comprising the amphiphilic molecules is suspended from the castellations 46 which contacts the electrically conducting liquid. The polar medium may comprise a buffering agent. The apolar liquid may comprise a hydrocarbon or an oil or a mixture thereof. Suitable oils include silicone oil, AR20 or hexadecane. The castellations may comprise grooves as may be seen from FIG. 6, which enable the flow of polar and apolar liquid into and out of the amphiphilic membrane region, for example to allow excess liquid to flow from the amphiphilic membrane region. These grooves also assist with the clipping process and ensure that the amphiphilic membranes are suspended in the correct position.

As an alternative to flowing apolar medium across the top of the body, the apolar liquid may be directly deposited onto the surface of the body for example in the form of fine droplets applied by electrostatic spraying.

The polar medium may comprise nanopores which can insert into the amphiphilic membrane and provide an electrical path between the polar medium and the electrically conducting liquid though the amphiphilic membrane. The polar medium may thereafter be removed, for example by displacement with air. Instead of removing the polar medium, the polar liquid may be left behind. Alternatively, following removal of the polar medium, a further medium comprising nanopores may be added to the amphiphilic membranes. In order to minimise any diffusion across the nanopore the polar medium and the electrically conducting liquid may be osmotically matched. The extent to which the amphiphilic membrane may be clipped and formed successfully on the electrically conducting liquid is determined by a number of factors such as the contact angle between the electrically conducting liquid and the material of the body, the contact angle between the apolar liquid and the material of the body, as well as the width of the capillary channel and the height of the castellations.

Ideally, one nanopore is provided per membrane. The extent to which this occurs is determined in part upon the concentration of the nanopores in the medium applied to the membranes. The extent to which nanopores insert into the membrane may be controlled by voltage feedback control, such as disclosed by PCT/US2008/004467 (published as WO2008/124107).

In order to provide reliable electrical connections between the two surfaces of the respective bodies, it is preferable that they are both able to conform to each another to some degree. However, the surfaces may be substantially rigid (and e.g. planar) or flexible. FIG. 8 shows an example of the structure of one electrode 38 in the array of electrodes. A conductive layer 41, for example a metal layer such as a platinum layer, is provided on surface 42 of the body 37 in which the electrode 38 is provide. An SU8 seedlayer is applied to the surface 42 and optionally over part of conductive layer 41, to define an exposed electrode area 44 to which the electrical liquid may be contacted. The SU8 can be modified with a silane coating to provide a hydrophobic surface. That is, the array of electrodes 38 comprises an array of exposed electrode areas 44. The liquid electrical contacts 35 form electrical connections to the exposed electrode areas 44, in use. In this example, the conductive layer 41 is formed on an insulating substrate 46, which could be silicon, for example. Conducting interconnects 45, for example doped silicon oxide, are provided in the insulating layer to provide electrical connection between the exposed electrode area 44 and a printed circuit board (PCB) 47 by bump bonding of solder 48. In this example, the PCB 47 is then further connected to an ASIC 27. As such, the additional layers allow for the preparation of a surface 42 to be optimised for making the electrical contacts, without risking any adverse effects to delicate components such as ASIC 27.

FIG. 9 is a schematic diagram indicating one way in which the liquid connectors 35 can be produced in a body 32. In FIG. 9A, body 32 is provided with an array of capillaries 34 which are empty (i.e. filled with the surrounding atmospheric gas, or another liquid which is not the conductive liquid used to form the liquid connectors 35). The conductive liquid is flowed underneath the body 32 in a channel. As shown in FIG. 9B, the liquid flowing through the channel is forced by the pressure in the channel through the capillaries in the body 32. The channel can then be cleared, as shown in FIG. 9C, by flowing air (or another fluid) through the channel, but leaving behind the liquid trapped in the capillaries 35. Such a method can be used to obtain a capillary filled with a liquid having a convex projection from each end of the capillary. In this scenario, the operation of FIG. 8C, using the flow of the lower viscosity fluid to produce the desired convex shape is termed 'clipping'.

FIG. 9 is an example of filling the capillaries by using positive pressure, but other methods of filling are possible, such as by passive or capillary action, or using negative pressure (i.e. a vacuum) to draw liquid through the capillaries in body 32. For example, FIG. 10 is an example of dip filling.

In FIG. 10, the capillaries 34 are dip filled under vacuum. The capillary substrate 32 is drawn through the electrically conducting liquid in a reservoir 53, in the direction of the arrow, and filled under vacuum. Capillaries 34 filled by a method such as that in FIG. 10 can be subsequently subjected to a 'clipping' operation as discussed above with reference to FIG. 9c, in order to give the desirable convex shape to the free surfaces of electrical connectors 35. Such clipping can be performed using air as the 'clipping' fluid, and a conductive liquid having a wetting of between 80-110° to the material of body 32. Suitable systems include a photo-polymerised poly(ethylene glycol) dimethacrylate (PEGDMA) based hydrogel with an ionic liquid, or polyacrylamide with an ionic solution.

As it will be appreciated from the foregoing discussion, the very small pitch of the electrical connections and the potentially large numbers of electrodes of the array, particularly in nanopore applications, requires careful alignment between bodies 32 and 37 in order that the liquid connectors 35 align with the electrodes 38. However, it should be noted that there is typically an element of redundancy in nanopore system experiments, such that the same (or equivalent) measurements are being taken in multiple different wells.

Indeed, the number of electrical connections between body 32 and 37 (corresponding to the number of individual nanopore measurements being taken) may be many thousands. As such, it can be acceptable for the alignment of bodies 32 and 37 to be offset by a multiple of the pitch, such that electrical connections at the edge of the array are not formed, but connections at the centre of the array are formed. As such, this can give some leeway in correctly aligning the bodies 32 and 37. That is, even if the alignment is not perfect, if it is at least only out of register by a multiple of the pitch size then viable connections can be made. Put another way, the alignment means can permit contact of the array of electrical connectors 35 and the array of electrodes 38 such that they are offset from each other when contacted and wherein the number of resultant electrical connections between the arrays is less than the number of electrical connectors 35 or electrodes 38 of each respective array.

In any case, it is desirable to provide some form or alignment means, as part of the first and second bodies 32 and 37, so as to substantially prevent lateral movement between the two surfaces (the opposed surfaces of the first and second bodies 32, 37) when the electrical connections are formed. The alignment means can, for example, be provided on the surfaces of each respective body 32 and 37.

Figure 12:
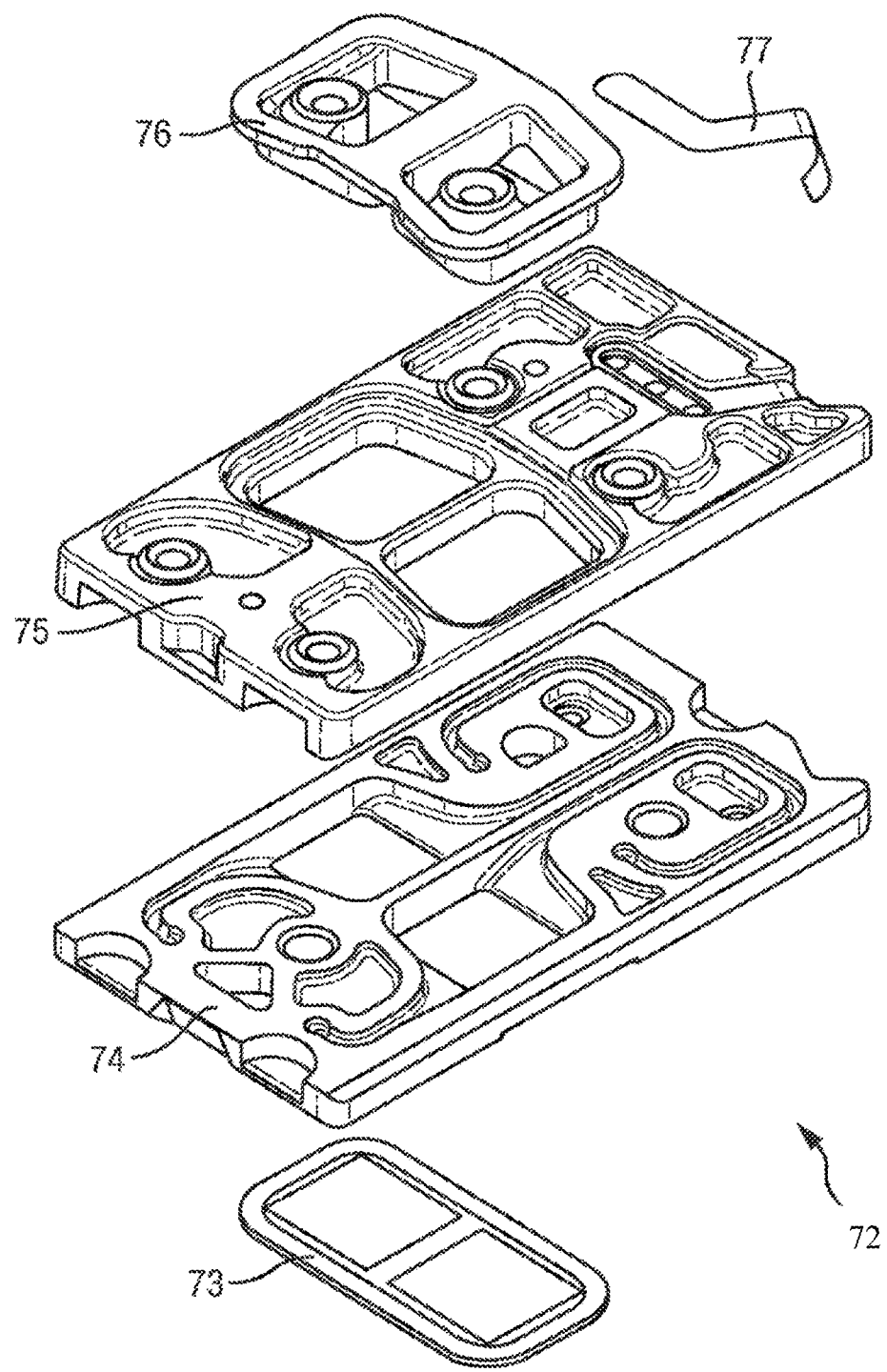
FIG. 12 is a perspective view of subcomponents forming a component of an electrical device.
Figure 13:
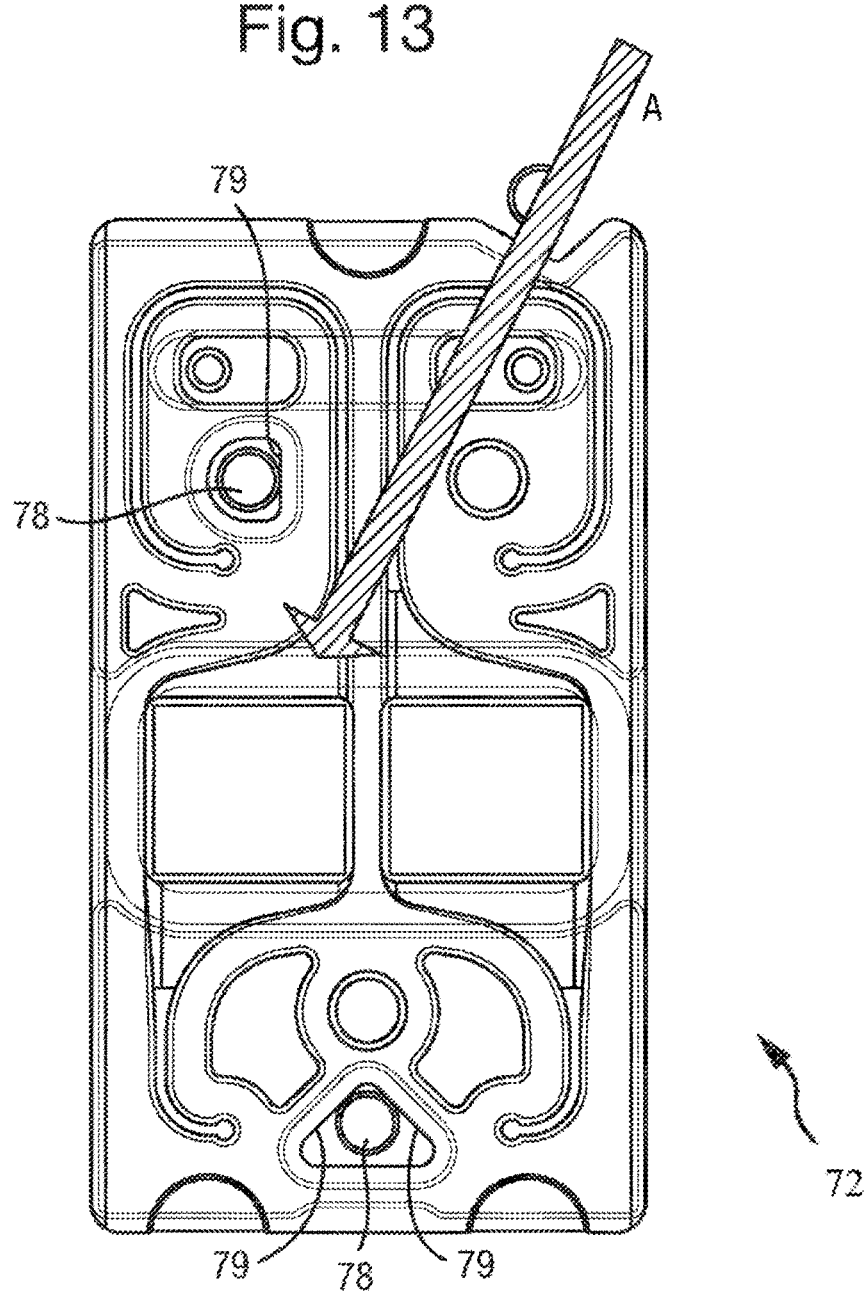
FIG. 13 is a plan view of some of the assembled subcomponents of FIG. 8, illustrating the alignment features.

One approach to providing suitable alignment is shown in FIGS. 12 and 13. In any alignment system, there are 6 degrees of freedom to constrain (X, Y, Z, pitch, yaw, roll). In this system Z, pitch and roll are constrained by pushing component 72 comprising the capillary array onto the surface of component 71 comprising the electrode array (not shown in FIG. 12 but shown as part of modular component 130 in FIG. 19). The component 72 in the example of FIGS. 12 and 13 is made from five main sub-components, although other arrangements in other embodiments are possible. The well- and liquid connector-containing sub-component 73 is lowermost in FIG. 12, and also contains structures required to contain buffer and form membranes across the wells. That sub-component 73 can be aligned and bonded to a larger lower flowcell sup-component 74, which contains alignment features and fluidic channels. As such, the small sub-component 73 can be more easily aligned by the alignment of the larger sub-component 74. A further sub-component 75 can be an upper flowcell component, which can provide fill ports for processing and sample addition, frit containment and mediator reservoir, and electrode/spring attachment (discussed further below).

A separate infill sub-component 76 fits into the window of sub-component 75, allowing closure of the flowcell parts after e.g. formation of membranes in a factory process, and also contains additional top-loader ports. A bent spring 77, preferably stainless and platinum plated, is provided to electrode contact, and to also provides biasing force as part of the alignment.

In this example, alignment can be achieved by biasing contact points in the lower flowcell subcomponent 74 against alignment pins 78 (present in component 71). In FIG. 13, two contact points 79 are shown against the lower alignment pin 78, whilst a single contact point is present for the upper alignment pin 78. Although not shown, spring 77 (when the component 71 is assembled) provides a biasing force (indicated by arrow A) across the component that urges the contact points 79 towards the alignment pins 78, whilst also contacting the common electrode 50.

This method allows highly repeatable alignment, but accuracy can be low, dependent on component tolerances. To maintain the high overall accuracy required to align the components 71 and 72, and avoid expensive high tolerance requirements and a tolerance build up through the assembly, each subcomponent 73 can be individually aligned and bonded into the lower flowcell 74. For example, every lower flowcell component 74 could be mounted on a reference master containing the two pin reference points under an optical alignment system. This can allow imperfections in the lower flowcell subcomponent 74, e.g. due to the moulding process, to be reduced in impact with respect to the overall alignment of components 71 and 72.

Similarly, the alignment pins of component 72 can be individually aligned before being bonded in place. During manufacture, these pin features can be inserted into a reference master that duplicates the ideal flowcell 74, such that the pins can be aligned optically with respect to the ideal flowcell master and fixed into place. This can assist in lowering the negative impact on alignment due to tolerance build up and allow better overall alignment than e.g. general machining tolerance would allow.

The component 71 is aligned in the z axis by pushing it into component 72 by hand. It is maintained in position by the spring force pushing against the alignment pins 78. In addition, further positioning features such as a small lip on the lower flowcell subcomponent 74 can assist with holding the component 71 in place, although such features should exert a lower force than the electrode spring 77, such that they do not bias the system out of alignment.

Figure 14:
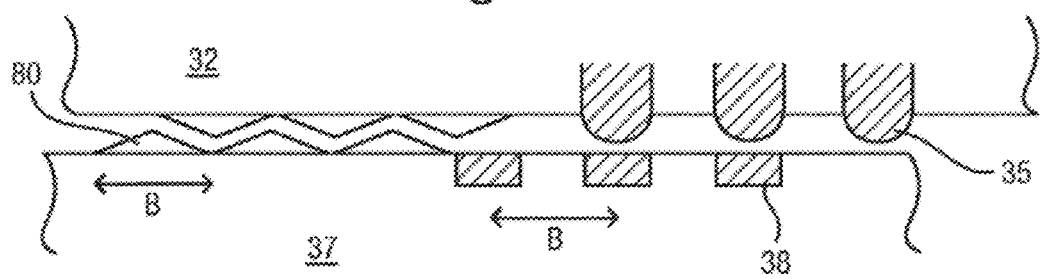
FIG. 14 is a schematic drawing illustrating an alternative set of alignment features.

An alternative method of alignment (FIG. 14) can be to make use of microfeatures 80 on the contacting surfaces of the bodies 32 and 37. Such microfeatures 80 could be machined or moulded into the surfaces by any appropriate method. In one example, as depicted, these features could be provided as complementary "saw-tooth" structures, where the amplitude ('B' in FIG. 14) of the repeating saw-tooth pattern corresponds to the pitch of the capillaries. However, any suitable shape (e.g. such as square 'crenulations') with same amplitude B could be used. Such patterns can be provided in directions parallel to both axes of the electrode/connector arrays, to provide alignment along each axis. As discussed above, such an arrangement could encourage accurate local alignment whilst allowing for outer connections to not be made owing to the overall alignment being out of register by an integer multiple of the array pitch.

Figure 15:
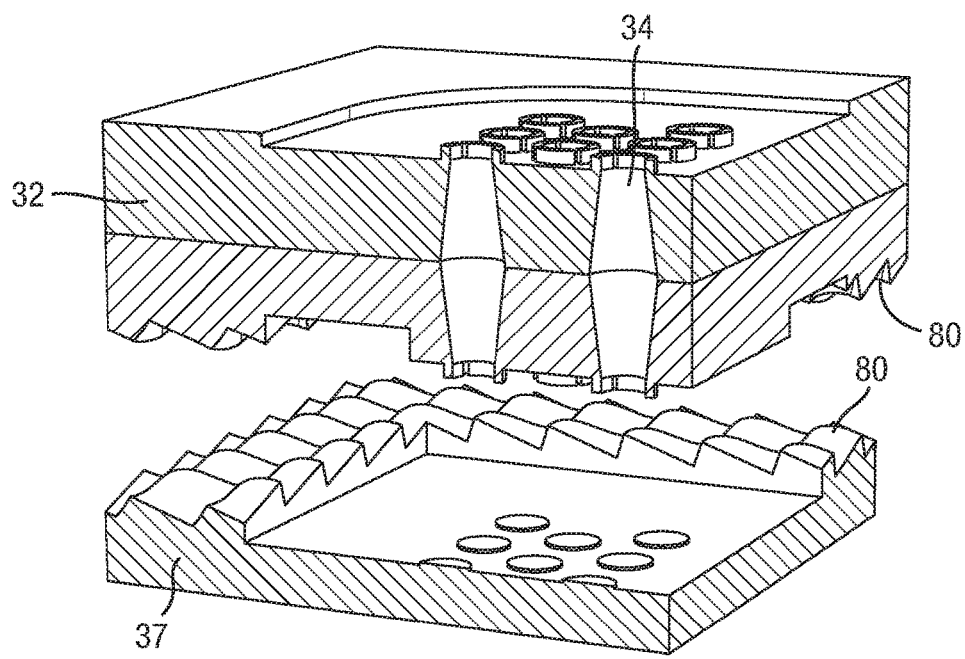
FIG. 15 is a schematic drawing illustrating another alternative set of alignment features.
Figure 16:
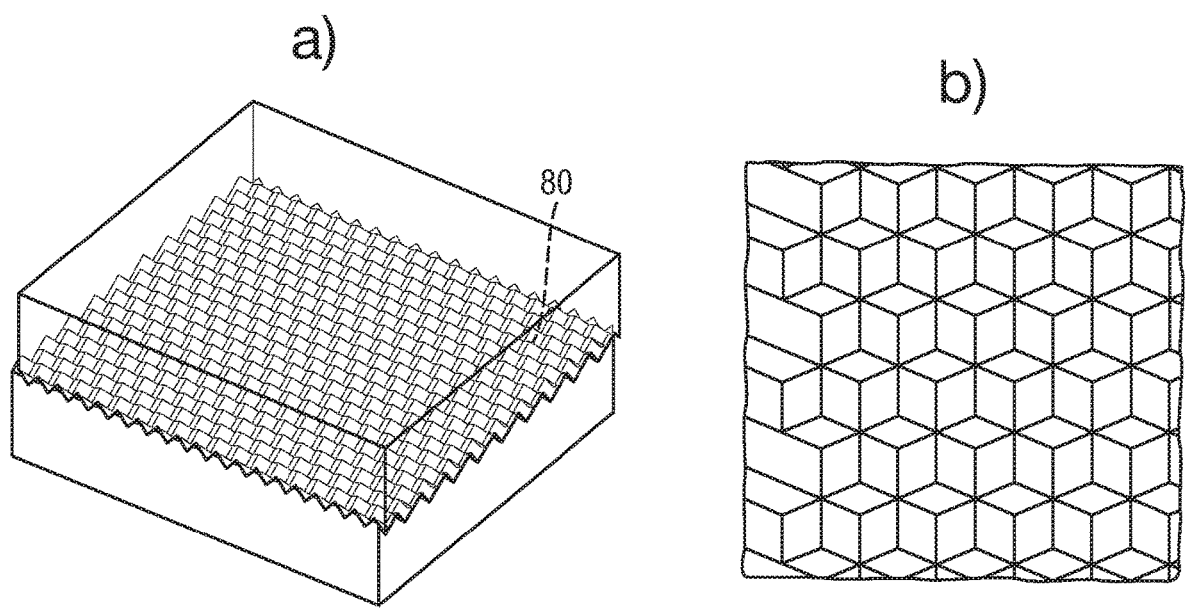
FIG. 16 is a schematic drawing illustrating another alternative set of alignment features.

Another example of such an arrangement is shown in FIG. 15. In this example, 'shark skin' microfeatures 80 are provided around the edges of bodies 32 and 37. Similarly, FIG. 16 shows another microfeature pattern 80. FIG. 16a shows an example of the pattern on a surface of body 32 or 37, whilst FIG. 16b shows an example of the pattern as seen from above. As can be seen from FIG. 16b, the pattern is effectively cubic in nature, resembling an isometric grid from above. This pattern could allow for sliding/alignment along three axes, which would be useful when considering hexagonal arrays of connectors 35 and electrodes 38.

Figure 18:
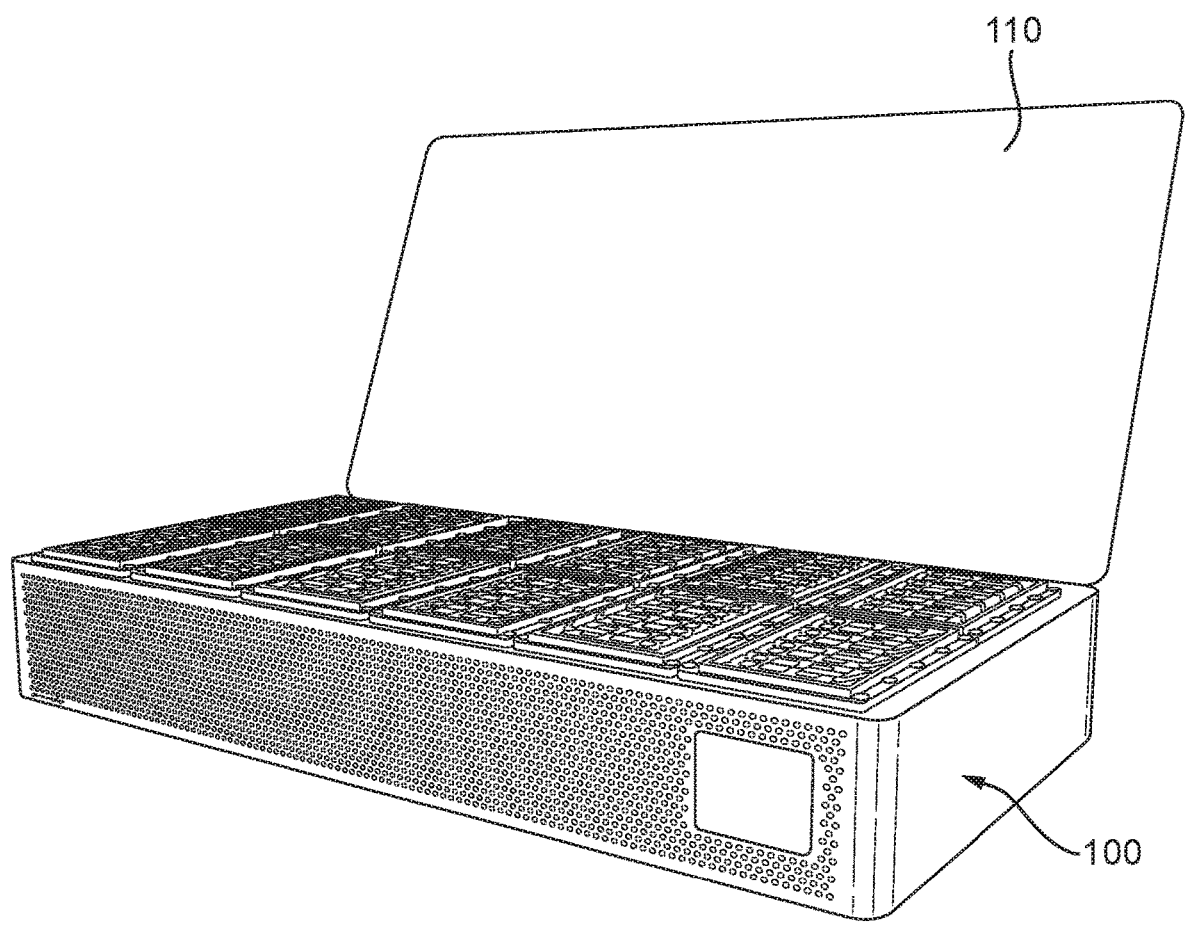
FIG. 18 shows an analysis instrument comprising a plurality of electrical device modules provided within a housing.

FIG. 18 shows an analysis instrument 100 comprising a plurality of subcomponent parts. The lid 110 may comprise a display. The parts may be provided in modular form allowing for the addition to or removal of arrays from the instrument. The instrument may comprise one of more such analytical devices.

Figure 19:
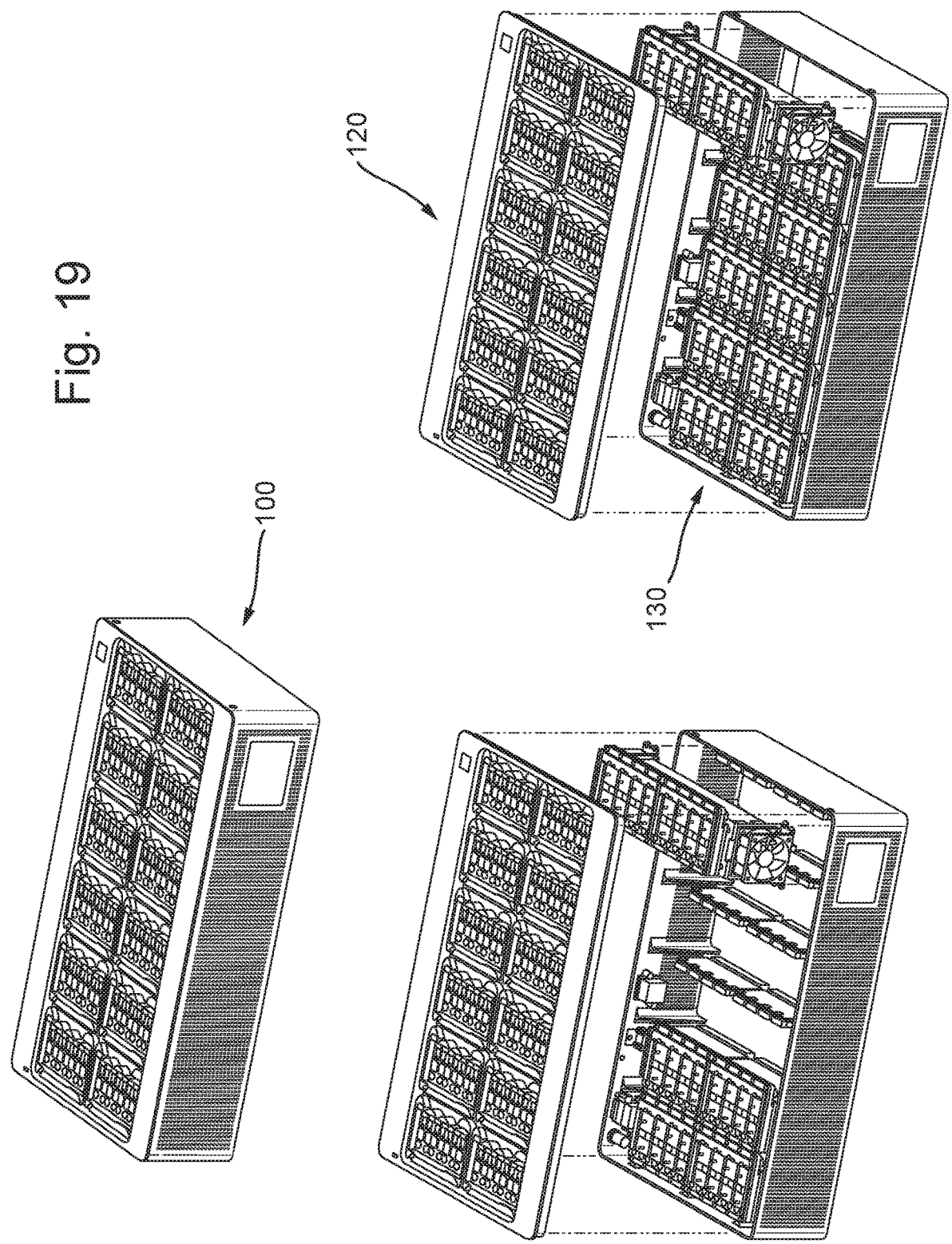
FIG. 19 shows an expanded view of the analysis instrument.

FIG. 19 shows expanded views of the analysis instrument 100 with six modules 120, each module comprising a plurality of first bodies as shown in FIG. 12, and an equivalent number of modules 130, each comprising a plurality of second bodies comprising the array of electrodes. The modules may be individually removed or added to the instrument depending upon the number of devices that are required. The plurality of modules 120 are contained in a compartment which may be lowered onto the plurality of modules 130 to connect the individual devices.

Figure 20:
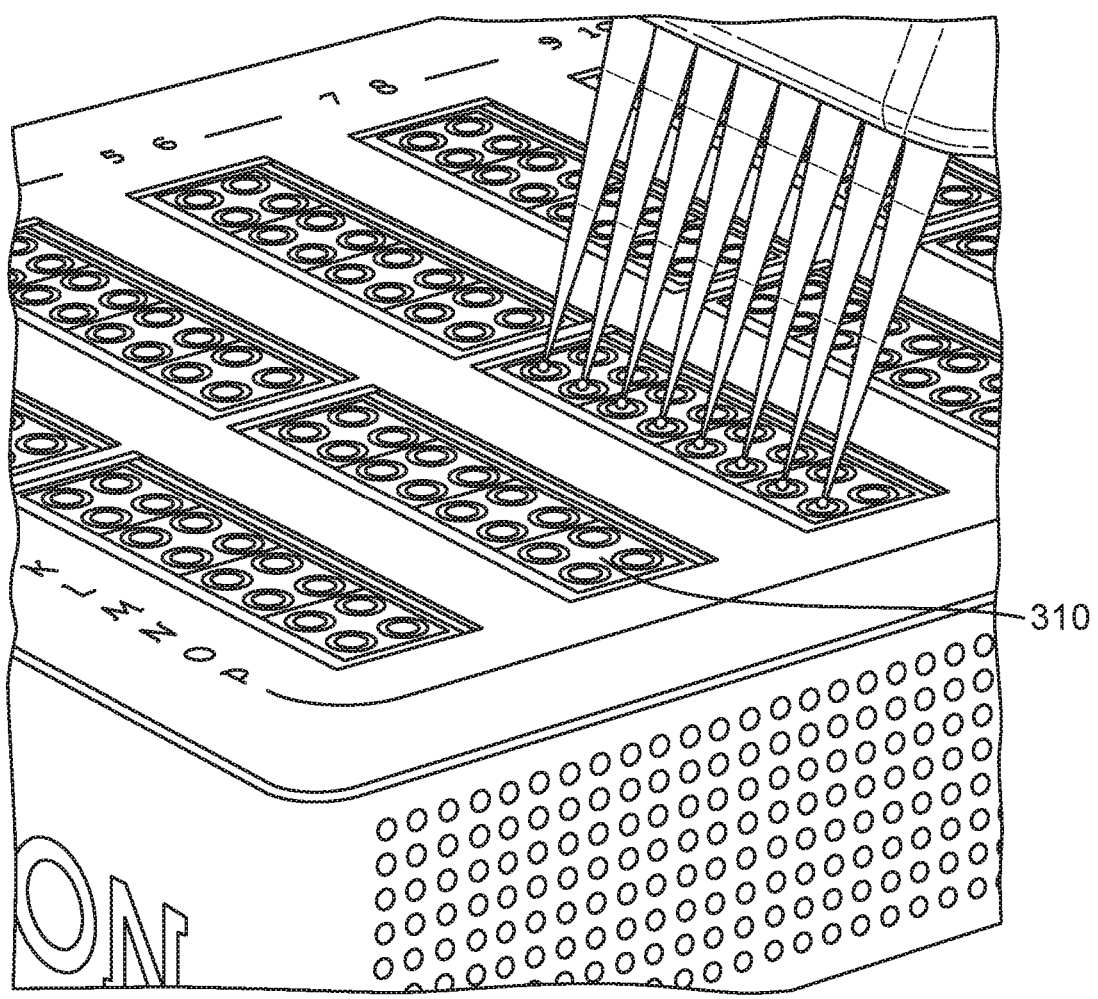
FIG. 20 shows a top view of the analysis instrument with the sample loading ports.

FIG. 20 shows a view of the instrument with sample loading ports 310 for loading sample onto the plurality of electrical devices provided within the instrument. Sample may be loaded for example by means of a multi-pipette, as shown in the Figure.

Figure 22:
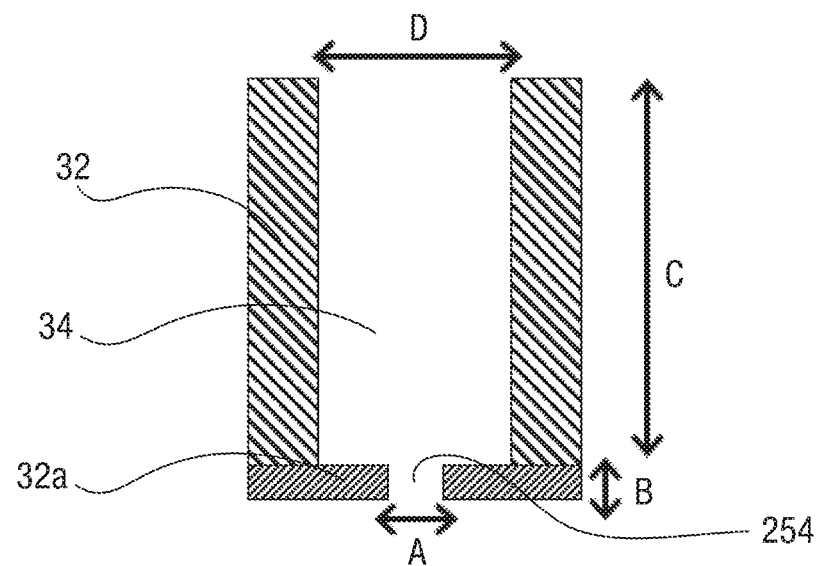
FIG. 22 is a schematic representation of an alternative capillary channel design.

FIG. 22 shows an alternative design of the well arrays. One potential drawback with the method of forming the connectors 35 as shown in FIG. 9 is that the length of the gel protrusions might vary over the array area if the formation conditions are not adequately controlled. This can result in the force transmitted through the connectors, in use, varying from connector to connector because some connectors are 'squashed' harder than others. This in turn leads to the risk of the most squashed connectors 35 being pushed up within the wells, which could cause damage to the nanopore membranes and the distal end of the channels.

FIG. 22 shows schematically (and without the pillars 33 at the top of each well) an arrangement that limits the potential for the connector 35 to move within the well after it is formed. The well is formed with an overhang 32*a* compared with the main body 32. As a result there is an aperture 254 introduced to (in this example) the bottom of the well which is smaller than the diameter of the main well.

As a guide, the dimensions in FIG. 22 could be as follows. Aperture diameter A could be around 50 µm, but that can vary depending on whether a single or multiple apertures are used or the type of pattern (see below). The body 32 with aperture 32*a* may be constructed from a laminate type UV photoresist such as TMMF S2000 (Tokyo Ohka Kogyo Ltd) ('TOK'). The body may be constructed by laminating one or more layers of photoresist material and exposing selectively to UV radiation in order to provide the desired shape and structure, with the laminate parts not exposed to UV being removed, for example by washing. The thickness of the aperture B could be around 30 µm, which corresponds to a single layer of laminate. The height of the well C may be for example around 210 µm, which corresponds to seven layers of TOK laminate, but which can be varied to alter depth of the well. Finally, the width of the well D can be around 100-120 µm.

As mentioned above, the TOK material has the advantage (from a fabrication perspective) that it does not let much light pass through it, and a sufficiently thick layer will let no light through it at all. As such, the main body 32 is too thick to allow light to pass through, but the overhang 32*a* is thin enough to allow to allow some UV light (wavelength of 265-365 nm) to pass through it. This wavelength of light is used during the gel curing process step (discussed in more detail below).

Figure 23:
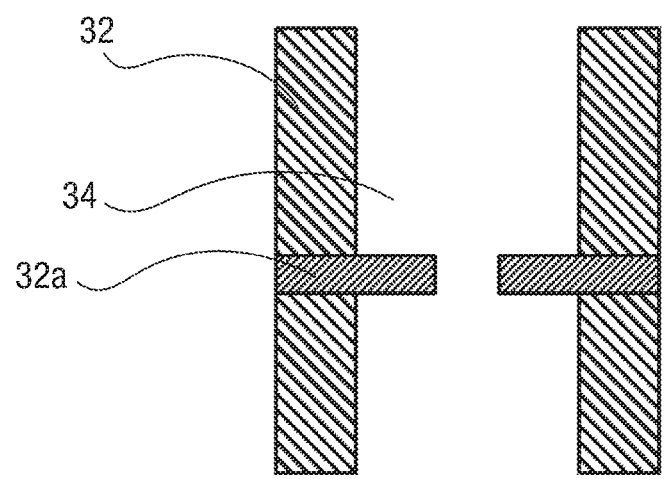
FIG. 23 is another alternative capillary channel design.

FIG. 23 illustrates the point that the overhang 32*a* does not necessarily have to be positioned at the bottom of the well to obtain the benefits discussed. It could, for example be positioned within the well. In FIG. 23 it is positioned mid-way through the well. However, in practice, it is simpler to manufacture the device with the apertures at the bottom of the well.

Figure 24:
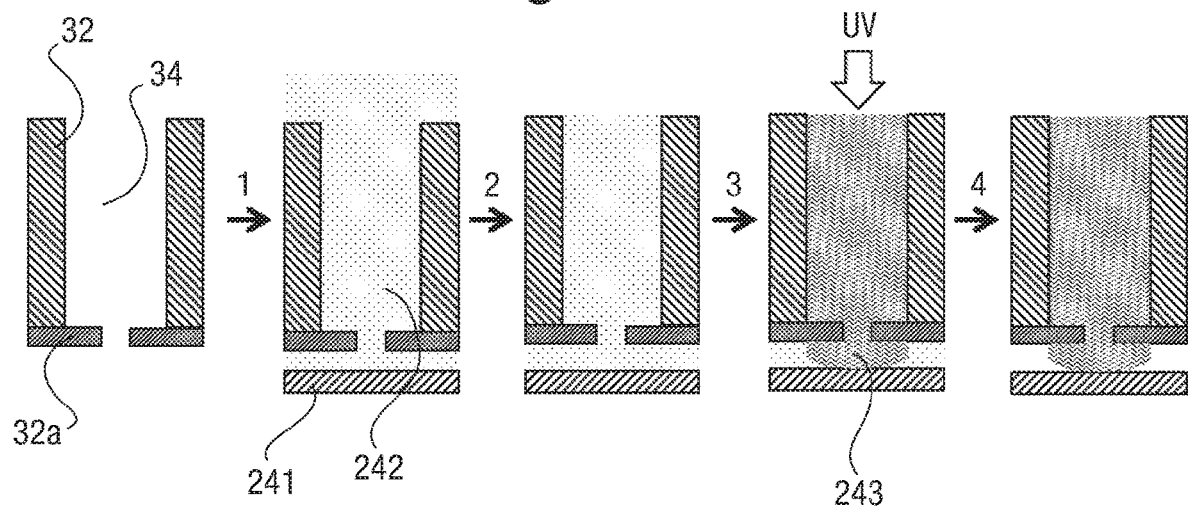
FIG. 24 illustrates an alternative process for forming connectors.

A further benefit, in terms of consistency of the gel protrusion is achieved by an alternative production process, illustrated in FIG. 24. The device as illustrated in FIG. 22 can be positioned at a predetermined distance from a fluid stop 241. As the fluid stop 241 is provided below the overhang 32*a* it serves to define the length of the protrusions. The length of the protrusions may be optimised by selecting an appropriate distance between the fluid stop and the overhangs. As a result, any variation in the height of the channels over the array (e.g. due to the array not being perfectly flat) may also be compensated for by providing a very flat structure for the fluid stop 241. That is, if the fluid stop 241 is flat, all the gel protrusions will extend to that same flat surface. Even if this results in some variation in the gel protrusions themselves, the overall device will fit more consistently with other connectors due to the evenness of termination of the gel protrusions. Put another way, the overall height of the connectors 35 (the gel pillars plus the protrusions) will be constant, enabling a flatter structure to be connected to the electrodes. Further, as mentioned above, the overhang 32*a* serves to resist any upwards force of the protrusions and to secure the gel. It thus reduces any upwards movement and subsequent damage to the membranes.

As shown in step 1 of FIG. 24, the body 32 containing the capillary array is positioned with respect to the fluid stop 241 and the system is filled with a suitable fluid 242. That is, one side of the capillary array is aligned with respect to the fluid stop 241 to create an 'end-space' between the capillary array and the fluid stop that will dictate the size of the gel protrusion to be formed. A suitable electrically conductive filling fluid is, for example, a solution of polyacrylamide, a photo initiator (2-Hydroxy-4'-(2-hydroxyethoxy)-2-methyl-propiophenone) and water.

In step 2, the excess solution is then flowed out of the system before, in step 3, the UV irradiation occurs. The UV light (265-365 nm can pass through the overhang 32*a*, as discussed above, but not through the walls of the main body 32. As such, the irradiation results in cross-linking over the area of the main well, even below the overhang 32*a* (as illustrated).

That is, the liquid within the capillaries and the liquid in the end-space within the projected area of the capillaries (i.e. the area directly underneath the capillary holes, in plan view) becomes a cross-linked gel 243. The liquid in the end-space not in the projected area of the capillaries (i.e. in the projected area of the walls of the body 32) does not become crosslinked. As an alternative UV light can be directed towards the liquid through the fluid stop 241, which can be made from a material that allows for transmission of UV light through it.

In step 4, the excess liquid which has not been cross-linked is flushed away leaving a protrusion which can make contact with the electrode array in a similar way to the fluid stop 241 against which it was formed.

As previously discussed, the protrusions can be compressed in order to make contact with the electrodes 38 below. This give in the system allows contact in all wells with the very flat electrode array. The manufacturing process just discussed allows for this contact to be achieved without requiring the upper part of the system to also be made as flat as the bottom part of the system to which it is connecting (as long as the liquid stop 241 is flat). In order to make as many electrical connections as possible between the arrays, it is advantageous that the two surfaces of the array that are brought into contact are flat. Any variation in surface height that is greater than the depth of the projections will result in some connections not being made. One or both of the array bodies may advantageously comprise or consist of a very rigid material such as glass or ceramic. The rigid material may be provided on the surface of an array body to be brought into contact with the other. Alternatively the core of an array body may comprise a rigid material which is overlaid with a surface layer of more flexible material such as TOK. A typical tolerance of variation in height across an electrode array of dimensions 1.3 cm by 0.5 cm having a glass or ceramic surface is 5 μm. A typical tolerance in variation in height observed across the surface of the second body (without any protrusions) is 20 μm across an array of similar dimensions. The height profiles along the respective arrays do not necessarily match as the components may be manufactured under different conditions and from different materials, thus the overall variation in height from the connected components may be even higher. A certain amount of compression of the gel liquid connects may be tolerated to compensate for any variation in surface height across the arrays. Gel protrusions can be compressed by up to 50%, more typically by 20%. However the use of a rigid body whilst preferable is not essential as materials such as TOK having a degree of flexibility can be used, for example in the first body, in circumstances where the two component parts arrays are brought together under a compression force. If it is desirable to have the connectors 35 contain UV sensitive components, such as a redox active material like potassium ferri/ferrocyanide, then such components can be added, e.g. by diffusion, to the connectors 35 after the UV cross-linking has occurred.

As already mentioned, there can be some variation in the aperture 254 design. In fact, there is no particular need to provide just a single aperture, and a number of different designs have been tested and shown to work. Indeed, if the single aperture is made too large the advantage of the overhang 32a/aperture arrangement can be diminished. That is, the gel can be compressed and pushed back into the fluid part of the system and disrupt the membrane formed above. However, it has been determined that a 75 μm hole in a 100 μm well, for example, is still sufficient to prevent the gel from being pushed back into the system in conditions in which having no overhang at all resulted in the gel being pushed back into the fluid part of the system.

Figure 25:
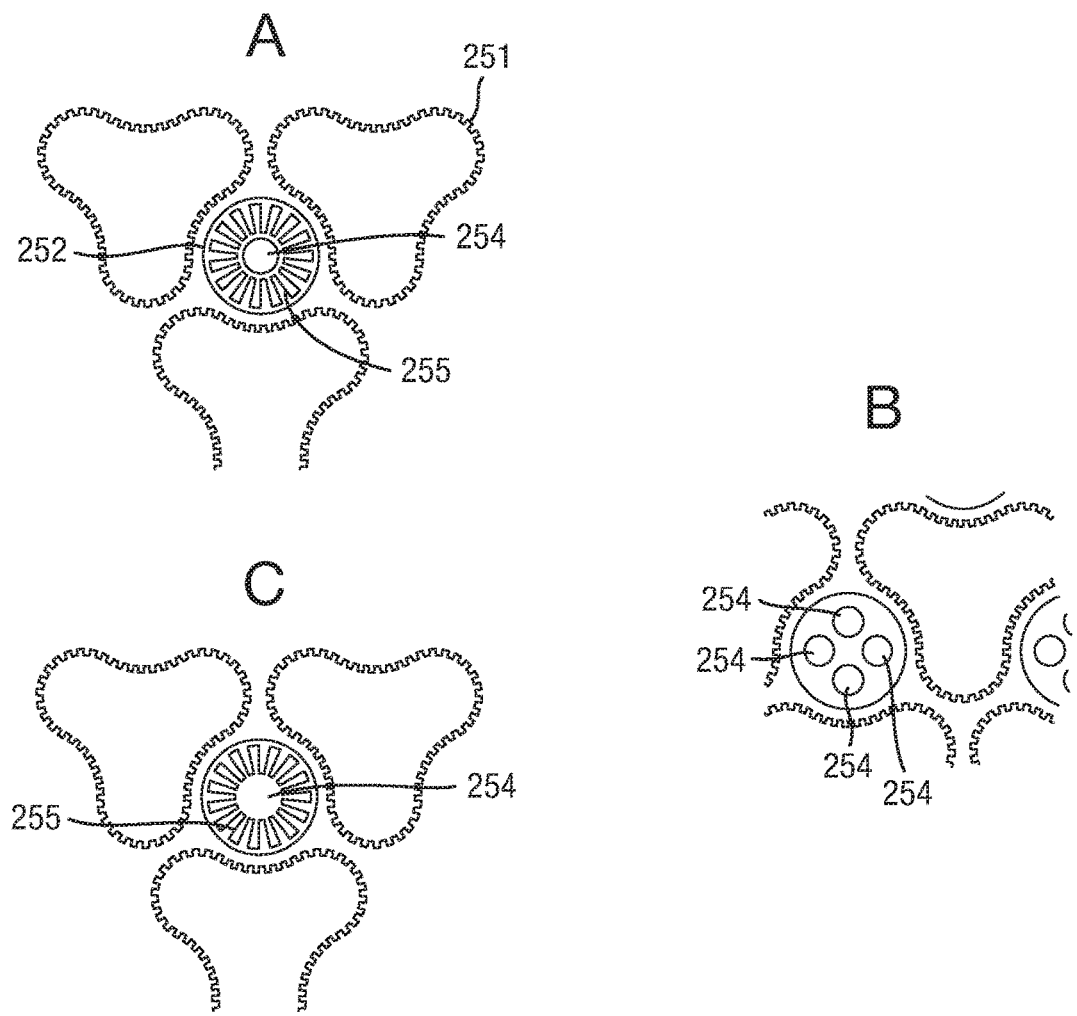
FIG. 25 illustrates alternative designs for apertures in the body overhang shown in FIGS. 22 and 23.

FIGS. 25A-C show schematics of alternative aperture designs in plan view from the top of the wells. As such, the drawings show the well 252 surrounded by supporting pillars 251. In FIG. 25A, the overhang 32a is formed as a main aperture 254 with a separately formed 'fan' of fins 255 around the aperture 254 too. In FIG. 25B, there are a plurality of circular apertures 254 formed within a single well. In FIG. 25C, there is a single aperture 254 from which a 'fan' of finds 255 projects (i.e. in contrast to FIG. 25A, the fins 255 are part of the same opening in layer 32A as the main aperture 254).

As an alternative to the production process shown in FIG. 24, FIG. 26 shows the result of a process in which the gel 243 is provided only partway up the channel 34. The process is similar to that shown in FIG. 24, but the channels 34 are only partly filled with uncrosslinked liquid. After the liquid has been crosslinked (and the excess liquid removed), the channel 34 is left partly filled with gel 243. Thereafter, as shown in the FIG. 26, the 'empty' space in the channel 34 can be filled as WO2014064443, which is hereby incorporated by reference herein in its entirety. For example, the channel 34 is filled with buffer/triblock 261 which clips to the side of the well/pillars (shown on top of the well in FIG. 26), before membrane formation occurs. This has the advantage that any variation in the height at the top of the gel connectors 35 may be compensated for.

FIG. 27 shows some schematic diagrams in connection with the alignment aspect previously discussed. If the alignment is achieved using alignment pins or bearings (such as discussed with reference to FIGS. 12 and 13), various degrees of freedom are potentially available to each bearing.

The use of a three bearing system can be desirable for ease of alignment, such as in a kinematic alignment system. The ball bearings may be provided on a resilient flexure mounting in order to provide a degree of tolerance that allows the component parts to be optimally attached in order to make the electrical connections. By providing tetrahedral, 'vee' shaped and flat locating points for the bearings, the necessary alignment can be achieved. The location of one spherical bearing in a tetrahedral locating point, constrains the bearing in three translational degrees of freedom. The 'vee' groove adds two contact points to provide y and z axis rotation constraint for another bearing, whilst a flat locator constrains rotation about the x-axis.

FIG. 28 shows an example of a device 280 comprising an alignment jig 281 for aligning an array of connectors to an array of electrodes.

FIGS. 29A-C show side elevations and perspective views of a more detailed example of a device comprising housing 290, and a detachable component 293 comprising an array of connectors housed within a carrier.

FIGS. 29D-F shows an expanded view of the detachable component 293 in greater detail.

Due to the accuracy required in aligning the component array of electrical connectors to the electrode array, especially in view of arrays having a large number of electrical connections and in view of the small pitch between the electrodes of the array, it is preferable to provide a device and kit which is capable of aligning the component arrays to each as opposed to relying upon connection of the component arrays by hand.

In an embodiment, the device may comprise a housing in which the component parts are located, wherein the housing is actuatable to connect and disconnect the component parts so as to create and break, respectively, said plurality of electrical connections. The housing may comprise a main body in which a first of the component parts is located and an arm in which the second of the component parts is located; wherein said main body and said arm are rotatably connected about a pivot, so as to allow connection and disconnection of the component parts by rotation of the arm relative to the main body. The device may comprise actuation means other than the provision of an arm and pivot about which the arm is rotatable to connect and disconnect the component parts. For example, the housing may comprise a first component part having pins, and the second component part may comprise corresponding holes that fit over the pins such that the second component part may be lowered and guided onto the first component part in order to make the electrical connections.

The component parts may be held together under a compressive force when connected, for example when connected in the manner as described above. This serves to compress the gels and/or deform the first body to account for any variation in surface height across the respective surfaces of one or both of the component parts. This can increase the total number of electrical connections that are made between the component parts.

FIGS. 29 A-C show housing 290, in which the component parts are located. The housing 290 comprises a main body with an arm 291 which is rotatable about a pivot 299 in order to connect and disconnect the detachable component 293 to and from the electrode array 294 provided on the surface of a silicon chip comprising the ASIC. As such, the housing is actuatable to connect and disconnect the component parts. Component 293 is held in place in the closed position by latches 292 and may be released by operating switch 291 in order to deflect the latches and rotate the arm. In order to assemble the device, the arm is first rotated to an open position as shown in FIG. 29B and held in an open configuration by spring 298. Component 293 may then be attached to connector 295 which also serves to provide an electrical connection to a common electrode housed within the detachable component. Also shown is a heat sink 297 in order to dissipate any heat formed by operation of the device and the alignment means 296 to accurately align the detachable component to the electrode array. Following attachment of component 293 to connector 295, the device may then be closed to attach the component to the underlying electrode array. Following use of the component, the housing may be reopened in order to remove component 293 which may be subsequently disposed of. A new component may be subsequently attached to the housing. The detachable component 293 of the device as shown in FIG. 29A may be a modular component of an analysis instrument, the instrument comprising one or more such devices which may be conveniently installed and removed from the instrument. The device may comprise a plurality of detachable components, for example arranged in series, connectable to a corresponding plurality of electrode arrays.

FIG. 29D shows an expanded view of detachable component part 293. Shown are four arrays of electrical connectors provided within TOK component 302. Component 302 is provided in a rigid frame 303 which serves to provide respective upper fluid chambers each for containing a test sample to be analysed. Frame 303 is attached to the flowcell 305 via gasket 304. The assembled flowcell and TOK laminate component 307 is provided in carrier 306. Component 307 is advantageously provided as being free floating within carrier 306 so as to enable accurate alignment of part 307 with the alignment means 296.

FIGS. 29E and F show an expanded view 308 of the flow cell showing microfluidic channels 309 for supplying test fluid to the respective arrays of electrical connectors. Test liquid may be introduced into the device via entry ports 311 which are accessible via holes 310 in the carrier.

FIGS. 29G and H show respective side and expanded views of the detachable component 293 showing alignment of the detachable component with the electrode array. Spring 320 provides a downward biasing force against the free floating component housed within the carrier 306. Electrical connection is provided via connector 321. The carrier may be made of metal or comprise a metallised coating in order to minimise any external electrostatic and electromagnetic influences and act as a Faraday cage.

The flowcell comprises a common electrode provided in chamber 322 separated from the upper fluid chamber by a frit 323.

FIG. 29I shows the device in its 'closed' configuration with the fluidic pathways and sample entry ports visible.

FIG. 30A shows an analysis instrument comprising a plurality of devices as shown in FIG. 29A. FIG. 30B shows an expanded view of a portion of FIG. 30A with the detachable component modules 293. Also shown is the underlying array of electrical connectors (electrodes) 294.

FIG. 31A shows body 400 for containing the liquid connectors, wherein the liquid connectors comprise a gelled aqueous component and a non-gelled aqueous component as exemplified in FIG. 26. The capillary channels each comprise a constriction 401 that extends longitudinally from the lower surface of the body, as depicted in in FIG. 31A, along a length of each channel.

The constriction comprises fins 421 that extend radially into the channel to define an aperture 404. Gaps 420 are provided between the fins which serve to draw up and hold liquid within the gaps and aperture. The liquid may be applied to the underside of the body in a method exemplified in FIG. 24 and crosslinked to form a gel. An aqueous liquid may thereafter be added to the channel region 405 by flowing an aqueous liquid across the surface of the pillar array 402 in a manner disclosed by WO2014064443 and as shown in FIGS. 35A-D to provide a liquid connection comprising a lower gelled portion contained within constriction 401 and liquid portion contained with channel region 405. The constrictions also serve to substantially reduce or prevent retraction of the gel protrusions into the capillaries when they are compressed. Movement of the protrusions into the capillaries can create pressure on the amphipathic membrane where present resulting in rupture. Partial retraction of the protrusions into the capillaries also reduces the amount of gel that is available to make the electrical connection with electrodes of the array. Due to the presence of the constrictions, the gel protrusions when compressed in their length direction, tend to increase in width. Thus it is important that the electrodes of the array are spaced sufficiently apart from each other such that compression of a gel protrusion does not result in short circuiting between neighbouring electrodes of the array.

Figure 35:
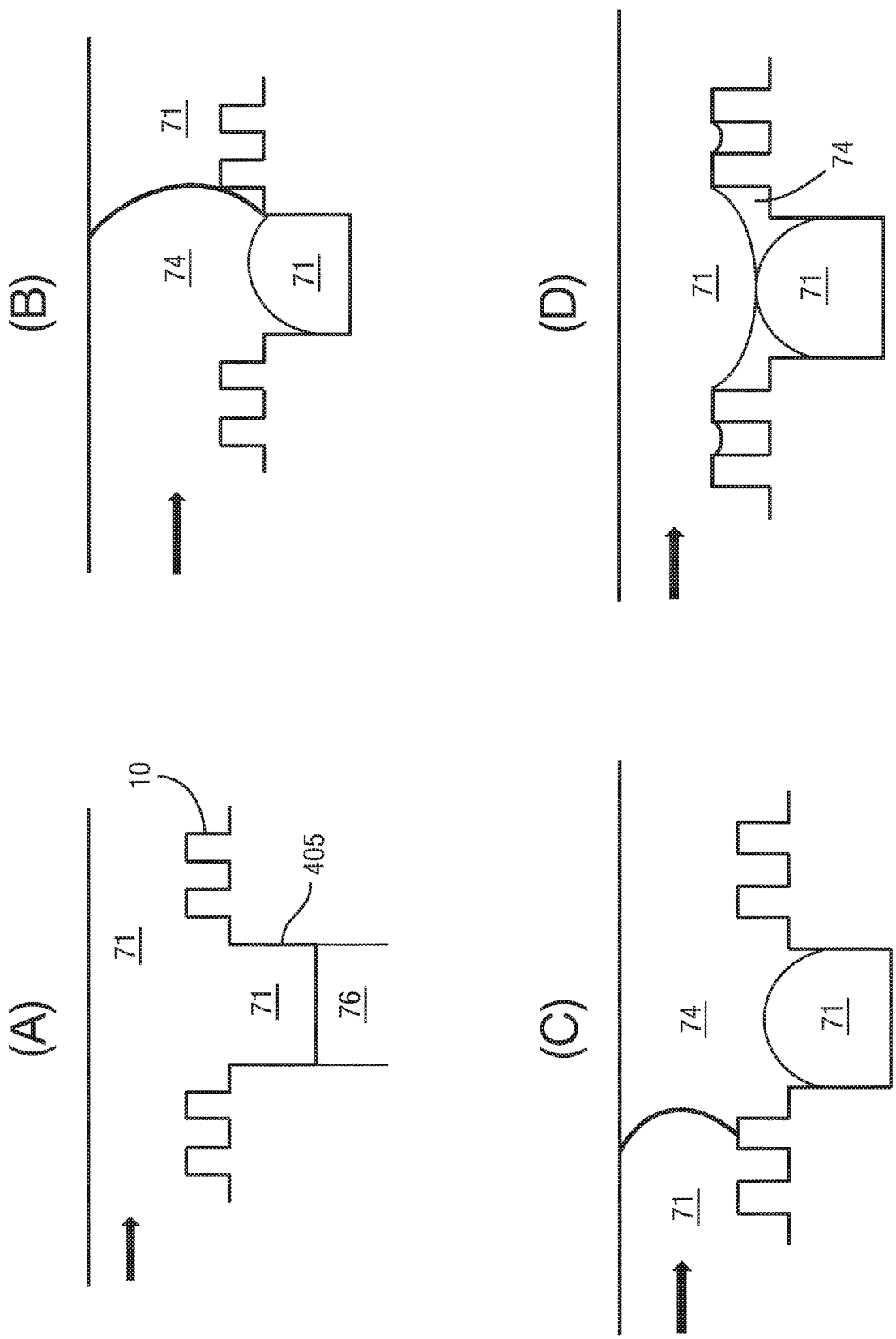

In order to provide the liquid portion of the liquid connector and a resulting amphiphilic membrane, a capillary channel may be filled according to a method as shown in FIGS. 35A-D. A polar medium 71, which may be an ionic liquid or ionic solution, such as an aqueous buffer solution, is flowed over the surface of the pillar array 10 in order to fill the remaining portion 405 of the capillary channel and contact the gelled portion 76 of the liquid connector, as shown in FIG. 35A. Thereafter an apolar liquid 74 comprising amphiphilic molecules is flowed over the surface of the pillar array to displace the excess polar medium 71, as shown in FIG. 35B. Polar medium may thereafter be flowed across the surface of the pillar array in order to displace apolar medium and form an amphiphilic layer separating the two volumes of polar medium, as shown in FIG. 35D. A further advantage of providing a liquid connector comprising a gelled portion and a non-gelled portion is that crosslinking of the gel does not take place at the pillar regions. Cross linking at these regions can lead to potential short circuiting between the respective channels of the array due to inability of the gel to be displaced from the pillar structures during formation of the amphiphilic membranes.

Other exemplary constrictions are shown in FIGS. 34A-F. As may be seen from these figures, the fins may extend partially into the channel such as shown in FIGS. 34 A, D and F or extend across the channel to define multiple apertures, as shown in FIGS. 34B, C and E.

FIG. 32 shows a side view of body 400 comprising the liquid portion of the liquid connector 406 and the gelled portion of the liquid connector 407 attached to electrode 408. The amphiphilic membrane 409 is provided across the distal end of the channel region 405.

FIG. 33A shows a portion of the connected device with the electrode vias 409 connecting the electrodes to the ASIC provided within body 410. FIG. 33B shows the device of FIG. 33A wherein the electrical connectors and electrodes of the array are disconnected.

The connectable array according to the invention has utility in other areas other than nanopore detection of analytes and may be used for the electrochemical detection or measurements of analytes at an electrode surface, for example in the indirect or direct measurement of analytes using an electron mediator and an enzyme such as the detection of glucose.

The forgoing discussion explains the invention by way of example only, and the skilled reader will appreciate that variations of the specific embodiments are possible within the scope of the attached claims.

The invention claimed is:

1. A kit comprising a pair of component parts adapted for connection to each other to provide a detachable electrical device, wherein the connected components of the device may be subsequently disconnected, comprising:
an array of electrical connectors, each electrical connector comprising an ionic liquid and/or an ionic solution as an electrically conductive liquid; and
an array of electrodes;
wherein the arrays can be brought into contact with each other so as to provide a plurality of electrical connections between the ionic liquid and/or ionic solution of the array of electrical connectors and the electrodes of the array of electrodes, and wherein the electrical connections may be subsequently broken by detaching the ionic liquid and/or ionic solution from the electrodes of the array;
wherein the array of electrical connectors and the array of electrodes are respectively provided in a first body and a second body; and
wherein the first body and the second body comprise alignment means so as to substantially prevent lateral movement between a surface of the first body and a surface of the second body when the electrical connections are formed.

2. A kit according to claim 1 wherein the interface resistance between the array of electrical connectors and the array of electrodes, when the electrical connections are formed, is 1% or less than the total resistance in the overall electric circuit.

3. A kit according to claim 1, wherein the electrically conducting liquid comprises a gel.

4. A kit according to claim 1, wherein the circuit resistance between each of the electrical connectors of the array and each of the respective electrodes of the array of electrodes, when the electrical connections are formed, is greater than 1 MΩ.

5. A kit according to claim 4, wherein the interface resistance between an electrical connector and an electrode of the array when connected is between 0.1 MΩ and 10 MΩ.

6. A kit according to claim 1, wherein the array of electrical connectors and the array of electrodes each have a pitch of 1 mm or less.

7. A kit according to claim 1, wherein the number of electrodes of the array is greater than 100.

8. A kit according to claim 1, wherein the electrodes are provided at a surface of the second body.

9. A kit according to claim 1, wherein the first body and/or the second body comprises a flow barrier to substantially prevent the flow of the electrically conducting liquid between the electrodes of the array of electrodes when the electrical connections are formed.

10. A kit according to claim 1, wherein the second body comprises an integrated circuit.

11. A kit according to claim 1, wherein the array of electrical connectors is disposed in an array of capillaries.

12. A kit according to claim 11 wherein each of the capillaries of the array comprises a constriction.

13. A kit according to claim 12, wherein the first body comprises one more electrodes so as to provide a plurality of capillary ionic flow paths through the electrically conducting liquid between the one or more electrodes and electrodes of the array of electrodes, when connected to provide an electrical circuit.

14. A kit according to claim 13, wherein the one or more electrodes is an electrode that is common to the plurality of flow paths.

15. A kit according to claim 12, wherein the first body comprises a plurality of nanopores, wherein each nanopore is provided in an insulating substrate provided across the ionic flow path such that current is passed between the electrically conducting liquid and the one of more electrodes through the nanopores.

16. A kit according to claim 15 wherein the insulating substrate is an amphiphilic membrane.

17. A detachable electrical device assembled from a kit according to claim 1.

18. A detachable electrical device according to claim 17 for characterizing an analyte.

19. A detachable device according to claim 17, further comprising:
a housing in which the component parts are located;
and wherein the housing is actuatable to connect and disconnect the component parts so as to create and break, respectively, said plurality of electrical connections.

20. A detachable device according to claim 19, wherein:
the housing further comprising an alignment means for aligning the component parts as they are connected so as to create said plurality of electrical connections.

21. An array of electrodes for use in the kit of claim 1, wherein a surface between electrodes is hydrophobic compared to the electrodes.

22. A method of connecting an electrical device, the method comprising:
providing an array of electrical connectors wherein each electrical connector comprises an ionic liquid and/or an ionic solution as an electrically conductive liquid;
providing an array of electrodes;
bringing the first and second arrays into contact to form a plurality of electrical connections between respective electrodes of the array and the ionic liquid and/or ionic solution; and
separating the electrically conducting liquid from the electrodes of the array of electrodes in order to break the electrical connections.

* * * * *